(12) United States Patent
Brown et al.

(10) Patent No.: US 6,790,639 B2
(45) Date of Patent: Sep. 14, 2004

(54) MAMMALIAN OSTEOREGULINS

(75) Inventors: Thomas A. Brown, Mystic, CT (US); Jeffrey R. De Wet, Pawcatuck, CT (US); Lori C. Gowen, New York, NY (US); Lynn M. Hames, Clinton, CT (US)

(73) Assignee: Pfizer Inc., New York, NY (US)

( * ) Notice: Subject to any disclaimer, the term of this patent is extended or adjusted under 35 U.S.C. 154(b) by 66 days.

(21) Appl. No.: 09/794,422

(22) Filed: Feb. 27, 2001

(65) Prior Publication Data

US 2003/0166239 A1 Sep. 4, 2003

Related U.S. Application Data

(60) Provisional application No. 60/185,617, filed on Feb. 29, 2000, and provisional application No. 60/234,500, filed on Sep. 22, 2000.

(51) Int. Cl.[7] .......................... C12N 15/00; C12N 5/00; C12N 15/63; C07H 21/04
(52) U.S. Cl. .................. 435/69.1; 435/320.1; 435/325; 536/23.5
(58) Field of Search .............................. 536/23.1, 23.5; 435/320.1, 325, 69.1

(56) References Cited

U.S. PATENT DOCUMENTS

2003/0064498 A1 * 4/2003 Rowe ........................ 435/196

OTHER PUBLICATIONS

N–Geneseq Accession No. AAZ36447, WO9960017, Nov. 25, 1999.*
Brown, T. A., et al., *Journal of Bone Mineral Research*, 15 (Suppl. 1): S170, 2000.
Brown, T. A., et al., *Journal of Bone Mineral Research*, 15 (Suppl. 1): S184, 2000.
GenBank Acc. No. AB046056, Aug. 9, 2000.
GenBank Acc. No. AB050259, Oct. 24, 2000.
Peterson, D. N., et al., *The Journal of Biological Chemistry*, 275 (46): 36172–36180, 2000.
Rowe, P. S., et al., *Genomics*, 67: 54–68, 2000.

* cited by examiner

*Primary Examiner*—Ram R. Shukla
(74) *Attorney, Agent, or Firm*—Peter C. Richardson; Gregg C. Benson; Gregory P. Raymer

(57) ABSTRACT

The invention features novel osteoregulin polypeptides, nucleic acid sequences which encode the polypeptides, vectors, antibodies, hosts which express heterologous osteoregulins, and animal cells and mammals with a targeted disruption of an osteoregulin gene. These osteoregulins play a role in regulating bone homeostasis, adiposity, and the calcification of atherosclerotic plaques. Accordingly, the invention also features screening assays to identify modulators of osteoregulin activity as well as methods of treating mammals for diseases or disorders associated with osteoregulin activity.

6 Claims, 28 Drawing Sheets

FIG. 1A (SEQ ID NO: 1)
```
   1 tgctaaaccc gaagaagcca agcttccctg aaggtgaacg acaccagaga gccgtgtgac
  61 gatgcaggct gtgtctgttg gactgttcct cttcagtatg acctggccgg caccaaagct
 121 gaatgaagat ggcagcagcg gcgtaacca agcaacatc cacttagcat ctgtgaagcc
 181 tgagcccatg gtgggtaaag gaacagaggg tgggcgagat gctccccttc acctgcttga
 241 ccagaacagg cagggtgcca ccctcctcag aaatatcact cagcctgtaa agagtctggt
 301 gacggggact gaagtacaga gcgacagaaa caaagagaag aaacctcaga gtgttctaag
 361 cgtaattcca acagatgtcc acaatactaa cgactactca gaagatacag agaaccaaca
 421 gagggatcta ctactccaga acagcccagg acaaagcaaa cacacccctc gggcccgacg
 481 aagcacgcac tacctaacac atctccccca aatcagaaag atttctcagtg acttcgagga
 541 cagtgcttcc ccagaccttc tagtgagggg ggataatgat gtccctcctt tcagtggaga
 601 tggacaacat tttatgcaca ctcccgacag aggaggtgct gttggatctg atcctgaaag
 661 ctcagctggt caccctgtgt caggctccag caatgtcgag attgttgacc cacacacgaa
 721 tggactgggc tctaatgaga tcccagggag agaaggtcac ataggcggtg cctatgcaac
 781 cagaggaaaa actgcgcagg gggcaggttc cgcggatgtg agccttgtgg aggcagcaa
 841 tgaaatcacg ggcagtacca aatttaggga gctccctgga aaagaaggaa acagagtcga
 901 tgccagcagc caaaatgctc atcaaggaaa agtagaattt cactacccac aagcgccctc
 961 aaaagagaag gtaaaagggg gcagcaggga gcacacaggg aaagccggtt acaatgaaat
1021 ccccaagagc agcaaggggcg gcgctagcaa ggatgcggaa gaatctaaag ggaaccaagt
1081 aacctttgact gaaagccaaa ggttcccagg caaaggcact ggccagtctt ctcacagtct
1141 tggtaatgag gttaaaagtg aagagactc ttctaatagt ctcagtagag agggattgc
1201 aatagcacac aggagaacaa gccaccctac acggaatagg gggatgtcac agcggagagg
1261 ctcctgggcc tcgagaagac cccatcccca cggcgcgta agcacccgcc aaagagacag
1321 tagtgagtca tcatccagtg ggagttctag cgagagcagt ggtgactaga cccgggggtt
1381 gaaccagttc ccagctctgg tcctgagaa agagaggacg cagcaggggac tgagcaaggt
1441 accagacttg gtcacctcca ggacactgtg ctgttttagt ggttgtaata agaatcccta
1501 ctcaaagttc taatgctttc tgaataaaaa ctttcgtaag aatttatata atggtaata
1561 tttgactagg cggcccatta aaatagtctg tggatgtcac aggtgccttg atatgtgatt
1621 tgctcttcag acatgaaaat aaagaggctt tctct
```

FIG. 1B (SEQ ID NO: 2)

MQAVSVGLFLFSMTWAAPKLNEDGSSGGNQGNIHLASVKPEPMVGKGTEGGRDAPLHLLDQNRQG
ATLLRNITQPVKSLVTGTEVQSDRNKEKKPQSVLSVIPTDVHNTNDYSEDTENQQRDLLQNSPG
QSKHTPRARRSTHYLTHLPQIRKILSDFEDSASPDLLVRGDNDVPPFSGDGQHFMHTPDRGGAVG
SDPESSAGHPVSGSSNVEIVDPHTNGLGSNEIPGREGHIGGAYATRGKTAQGAGSADVSLVEGSN
EITGSTKFRELPGKEGNRVDASSQNAHQGKVEFHYPQAPSKEKVKGGSREHTGKAGYNEIPKSSK
GGASKDAEESKGNQVTLTESQRFPGKGKGQSSHSLGNEVKSEEDSSNSLSREGIAIAHRRTSHPT
RNRGMSQRRGSWASRRPHPHRRVSTRQRDSSESSSSGSSSSESSGD

FIG. 2A (SEQ ID NO: 3)

```
   1 caaactttaa atttcagcaa atgcccagag actaagcccg aagaagccaa gctttcctga
  61 aggtgaatga cgccagaggg cctcatgaag atgcaggctg tgtctgttgg actgctcctc
 121 ttcagtatga cctgggcggc accaatgccg aatgaagaca ggagcagctg cggcaatcaa
 181 gacagcattc acaaggactt ggcagcatct gtgtatcctg atcccacggt ggatgaaggc
 241 acagaggatg ggcaagtgc tctccttcac ccgcctggcc agacaggta tggtgctgcc
 301 ctcctcagaa atatcacgca gcctgtaaag agtctagtga ctggggccga actacggagg
 361 gaaggaaacc aggagaagag acctcagagt gttctaagcg taattccagc agatgtcaat
 421 gatgctaaag tctccttaaa agacataaag aatcaagaga gttatctgct aacccagagc
 481 agcccggtca aagcaaaaca accgcccaga cccgacggag cactcactac
 541 ctgacacatc tcccacagat caagaagact cccagtgacc ttgaaggcag tggctccccca
 601 gatcttctag tgggggaga taatgatgtc cccccttttca gtggagatgg gcaacatttt
 661 atgcacattc ctggcaaagg agtgctggg tctggtcctg aaagctcaac tagtcgcccc
 721 ctctcaggct ccagcaaagc tgaagttatt gacccacata tgagtggact aggctctaat
 781 gagatcccgg ggagagaagg acatgtggc agtgcctatg caaccagaga caaagctgca
 841 caggggcag gctctctgcag tgggagcctt gtggggggca gcaatgaaat cacaggcagc
 901 accaatttca gggaactccc cggaaaagaa ggaaacagaa ttaatgccgg cagccaaaat
 961 gctcatcaag ggaaagtaga atttcactat ccacaagtgg cctgtctgtg aaaggtaaag
1021 ggggcgtgg agcatgcagg gagagctggt tacaacgaaa tcccaagag cagcaaaggt
1081 agctctagca aagatgcaga agagtccaaa gggaaccaat taaccttgac tgcaagccaa
1141 agatttccag gtaaaggcaa aagccagggc cctgctctgc cctctcacag tcttagtaat
1201 gaggttaaaa gtgaagaaaa ccattatgtg ttccatgaac aaatatctct acaccgaat
1261 aaagggatgt cacagcggag aggctcctgg ccttcgagaa ccttcaattc ccaagcgc
1321 gctagcaccc gccaaagaga cagcaggcga tcgtcatcca gtgggagttc tagtgagagt
1381 catggtgact agtccctggg attgaaccag tcccctgctc tagtcctgga ggaagagagg
1441 gcacagcagg aactgagcaa gccaacagac ctgctccct ccaggacatt gtgctatttt
1501 aatggtggtt ataagaattt ctactcaaag ttctcaatgct ttttcaata aaaacttca
1561 taagaattg tataataggt aatatttggt caggcgacac attaaaatag tctgtgaatg
1621 tcacaagtgc cttgatacgt catcatttgc tcttcagaca tgaaaataaa tatgcttgct
1681 ct
```

FIG. 2B

SEQ ID NO: 4)
MTPEGLMKMQAVSVGLLLFSMTWAAPMNEDRSSCGNQDSIHKD
LAASVYPDPTVDEGTEDGQGALLHPPGQDRYGAALLRNITQPVKSLVTGAELRREGNQ
EKRPQSVLSVIPADVNDAKVSLKDIKNQESYLLTQSSPVKSKHTKHTRQTRRSTHYLT
HLPQIKKTPSDLEGSGSPDLLVRGDNDVPPFSGDGQHFMHIPGKGGAGSGPESSTSRP
LSGSSKAEVIDPHMSGLGSNEIPGREGHGGSAYATRDKAAQGAGSAGGSLVGGSNEIT
GSTNFRELPGKEGNRINAGSQNAHQGKVEFHYPQVASREKVKGGVEHAGRAGYNEIPK
SSKGSSSSKDAEESKGNQLTLTASQRFPGKGKSQGPALPSHSLSNEVKSEENHYVFHGQ
NNLTPNKGMSQRRGSWPSRRPNSHRRASTRQRDSSESSSSGSSSESHGD

FIG. 3A (SEQ ID NO: 5)
CAAACTTTAAATTTCAGCAAAATGCCCAGAGACTTCTAATCCTGCAACAAGAAGCcaggtattctgaaggtgaaagatac
cagagattctcaaagatgcgagttttctgtgtgggactactccttttcagtgtgacctgggcagcaccaacattcaacc
acagactgagaaaactaagcaaagctgtgtggaagagcagagcaggaagaaaaacaaagacaatattggttttcacc
attgggcaagagagaataaatcaagagctatcatctaaagaaatattgtccaggaaagaaagaaagatttgtccctttct
gaagccagtgagaataaggaagtagtaacatgcctgagtaaatctcaaattatcctaagtcaactgggaataaaggtttgaggatg
cagtaacaaagagaatactcacaatgcctgaggatgtcaattatccataagcatcagaaataacatgcaacataatg
gagatgatgctatcagcaaactacatgacccaagaagaatatgcgcagctctcatcagaaatgttctaaacataatcccagc
gggccagtgactgctgattaaactcctgggggaagaataaaagaaacaaagaggcctaagagattcccaaagtccgtgat
aagtatgaattatgctaaagcacactcgtattcaacacaacattgactactccaaaacatctctcaaagtcaaaatcccagtgat
aaagcaaaagcaccatcgtattcaagagagaggggacaatgactagagaaggcaaagatattcaaacaggtttgcaggcccaa
tttgaaggcagcggttatacagatcttcaagagagaggggacaatgactagagaaggcaaagatattcaaacaggtttgcaggcccaa
taaggacattcctgtaaggagaagctactgtcctgacctagagtgttataatgagatcccagagaggcagagggcagcaacgatatcat
gtgaagctgagagtactcatctgacacaaaagaggcagagtgctgttgatgtcagcttgatgtcgcagccaaatgctcaccaagga
accatggaactaggagatgaaactgcgaaagaggcccctgaagagagaaacagagtggatgctgggcagcatgtcagctgaagtaccaac
gggtagtacaattttaaggagctccctgcacccctcaaaaatggcagtaccagagcagtctctaatagaaccaagcaaccttaaa
aggttgagtttcattacccctcctgcacccctcaaaaatggcagtaccagagcagtctctaatagaaccaagcaaccttaaa
tataatgaaattcctaaaaatggctagtaagggcaaaagtcaggcctgccattcttcctctcgtggtcttgataatgaaatcaaaa
tgaaaaacaaaggtttcctagtaagggcaaaagtcagagcctgccattcttcctctcgtggtcttgataatgaaatcaaaa
acgaaatggattctacacgaatagcaaggtatgccacaagggaaaggctcctggggtagacaaccccattccaacaggaggtt
caaataattctacacgaataaggtatgccacaagggaaaggctcctggggtagacaaccccattccaacaggaggtt
tagttcccgtagaagggatgacagtgtctgaagactgagtgagccaagaatcctggtctgagtgagagccatgggtgctgagctgacca
ggagttccagcggggtagtagtgagagaagaactgagtgagccaagaatcctggtctgagtgagagagccatggaatttgctatcttaatagt
ggtgaagagagagagtgacagtgtctgaagactgagtgagccaagaatcctggtctgagtgagagagccatggaatttgctatcttaatagt
cacagtataaaattctattaaaggctataatgttttaagcaaaaaatcattacagatctatgaatctatgaataggtaacatt
tgagtaggtgtcatttaaaatatagttggtgaatgtcacaaatgcctctatgttgctctgtagacatgacatgaaaataaa
caatatctctcgataa

FIG. 3B (SEQ ID NO: 6)
MRVFCVGLLLFSVTWAAPTFQPQTEKTKQSCVEEQRQEEKNKDNIGFHHLGKRINQELSSKENIVQERKKDLSLSEASEN
KGSSKSQNYFTNRQRLNKEYSISNKENTHNGLRMSIYPKSTGNKGFEDGDDAISKLHDQEEYGAALIRNNMQHIMGPVTA
IKLLGEENKENTPRNVLNIIPASMNYAKAHSKDKKKPQRDSQAQKSPVKSKSTHRIQHNIDYLKHLSKVVKKIPSDFEGSG
YTDLQERGDNDISPFSGDGQPFKDIPGKGEATGPDLEGKDIQTGFAGPSEAESTHLDTKKPGYNEIPEREENGGNTIGTR
DETAKEADAVDVSLVEGSNDIMGSTNFKELPGREGNRVDAGSQNAHQGKVEFHYPPAPSKEKRKEGSSDAAESTNYNEIP
KNGKGSTRKGVDHSNRNQATLNEKQRFPSKGKSQGLPIPSRGLDNEIKNEMDSFNGPSHENIITHGRKYHYVPHRQNNST
RNKGMPQGKGSWGRQPHSNRRFSSRRDDSSESSDSGSSESDGD

FIG. 4A (SEQ ID NO: 7)
```
CAAACTTTAAATTTCAGCAAAATGCCCAGAGACTTCTAATCCTGCAACAAGAAGCcaggtattctgaaggtgaaagatac
cagagattctcaaagatgcgagtttctgtgtggactactcctttcagtgtgacctgcagcagccaacatttcaacc
acagactgagaaaactaagcaagctgtgtggaagagcagaggATAACATACAAGGGTCACTATGAGAAACATGGCATT
ATGTTTTAAGTGTGTGTTTACATGTCACCTGAGAAGAAAAATCAAACTGATGTAAAGcaggaagaaaaacaaagacaat
attggttttcaccatttgggcaagagaataaatcaagagctatcatctaaagaaaatattgtccaggaaagaaaga
tttgtccctttctgaagccagtgtgagaataaggaagtagtaataaggcctgaccaatagacagagactgaata
aagaatatagtatcagtaacaaagagaatactcacaatggcctgaccaatatattatttcacaaattatccaagtcaactgggaataaa
gggtttgaggatggagatgtcagtgccagtatcagcaaactacatgaccaagaagaataatatggcgcagctctcatcagaaataacat
gcaacatataatgggccagtatgaattatgctgcgattaaactctaaagcacactaggaatgttctaa
acataatcccagccagtgatgtcagtgccagtatgaattatgctaaagcacacctaaaacatctctcaaaagtcaaaa
aaaagtccagtgatttgaaggcagcggttcctgagagtactggtcctgacctgatacagatcttcaagagcacacattgactacctaaaagtcatg
aatcccaaccttttaaggacattcctgagagtgaactctggacacaaaagccagttatacagatgagatcccagagagaaga
acggccaagcccaagtgaactaggagggacaactggtcctgacctgatgtctgtcagccttgtgatgtcagccttgtagagggca
tttgcaggcccaagtgaataccattggaactaggagggatgaactctttgacacaaaaagcagtagcaggcagatgatgtgttgatgtcagccttgtagagggca
aatggtgaaatacaccattggaactaggagggatgaactctttgacacaaaaagcagtagcaggcagatgatgtgttgatgtcagccttgtagagggca
gcaacgatatcatggtagtaacaagcgttgagtttcattacctccgtgaaaaatgccaaagccagtaatgtgtcaccagtcagagtcagtgatgtcagc
gctcaccaagggaaggttgagttcaaagttccaatccaaaatgcctgagtagcccctgaagtcatgagagcagtcaggcatttctaatggaacc
tgaaagtaccaactataatgaaaacaaagttcctagggcaaagtctcatgagaatcaggaatataataacactagaagcagtaggcaagaaataggaacc
agcaaccttaaatgaaaaacaaaatgaatcctagaagtctttaatgagaaaggacttcttacacgaatcaggccaagtagaacaaccccatt
aatgaaatcaaaaacagacaaaataattctccgtagaagggatgacagtagtgatctgacagtgagtgcccaagggtatgccacaagggcaaaa
tgtaccccacagagggtttagttcccgtagaagggatgacagtagtcatctgacctcactgcagtcaatggccaactctttaaggttgagagacggcaaat
ccaaccagggtttagttcccggggtccgcagcagtcccacggcagttccagaatcctcaccctctgaccctgagtgcagttcaaatatcctttggg
gactagtccaccaggagtcccacggcagttccagaatcctgaggacccaggctactcatccacagagccaactcctggtctccttggggaattttg
tgacagctgaccaggtgaccagtgaactgaaagtgaagaagctatatggaagctataaatgtctttaagcaaaaatcattacagatctatga
ctatcttaatagtcacagtatataaattctattaaggctatataatgtcttttaagcaaaaatgccttctatgttgcttgcttgtcctgtag
aataggtaacatttgatgtaggtgtcatttaaaaatagtggtgaatgtcacaaatgtggttgcacaagatagccttctatgttgtttgctctgtag
acatgaaaataaacaatatctctcgatgataa
```

FIG. 4B (SEQ ID NO: 8)
MRVFCVGLLLFSVTWAAPTFQPQTEKTKQSCVEEQRITYKGHYEKHGHYVFKCVYMSPEKKNQTDVKQEEKNKDNIGFHH
LGKRINQELSSKENIVQERKKDLSLSEASENKGSSKSQNYFTNRQRLNKEYSISNKENTHNGLRMSIYPKSTGNKGFEDG
DDAISKLHDQEEYGAALIRNNMQHIMGPVTAIKLLGEENKENTPRNVLNIIPASMNYAKAHSKDKKKPQRDSQAQKSPVK
SKSTHRIQHNIDYLKHLSKVKKIPSDFEGSGYTDLQERGDNDISPFSGDGQPFKDIPGKGEATGPDLEGKDIQTGFAGPS
EAESTHLDTKKPGYNEIPEREENGGNTIGTRDETAKEADAVDVSLVEGSNDIMGSTNFKELPGREGNRVDAGSQNAHQGK
VEFHYPPAPSKEKRKEGSSDAAESTNYNEIPKNGKGSTRKGVDHSNRNQATLNEKQRFPSKGKSQGLPIPSRGLDNEIKN
EMDSFNGPSHENIITHGRKYHYVPHRQNNSTRNKGMPQGKGSWGRQPHSNRRFSSRRDDSSESSDSGSSSESDGD

FIG. 5

Comparison of rat (rOR)/mouse (mOR)/human (hOR) osteoregulins

```
rOR   ------------MQAVSVGLFLFSMTWAAFKL---------------------------------       23
mOR   ------------MQAVSVGLILFSMTWAAFMP---------------------------------       31
hOR   ---------MRVFCVGLLLFSVTWAAFTFQPQTEKTKQSCVEEQRQEEKNKDNIGFHHLGK           52 rOR   -------------------------------GSSG------GNQGNIH-----------------       34
mOR   -------------------------------RSSC------GNQDSIHKDL--------------       45
hOR   RINQELSSKENIVQERKKDLSLSEASENKGSSKSQNYFTNRQRLNKEYSISNKENTENGL          112 rOR   LASVKFEPMVGKGTEGGRDAPLHLLDNRQGAILLRNITQPVKSIVTGTEVQSDRNKEKK            94
mOR   AASVYFDPTVDEGTEDQGALLHPPGQDRYGAALLRNITQPVKSIVIGAELRREGNQEKR          105
hOR   RMSIYEKSTGNKGFEDGDDAISKLHDQEEYGAALIRNNMQHIMGPVTAIKLLGEENKENT         172 rOR   PQSVLSVIPTDVHNTNDYSEDTENQQRDLLLQNSPGQS----KHTPRARRSTHYLTHLPQI        151
mOR   PQSVLSVIPADVNDAKVSLKDIKNQESYLLTQSSPVKSKHTKHTRQTRRSTHYLTHLPQI         165
hOR   PRNVLNIIPASMNYAKAHSKDKKKPQRDSQAQKSPVKS---KSITHRIQHNIDYLKHLSKV        229 rOR   RKILSDFEDSASPDILVRGDNDVPPFSGDGQHFMHTPDRGGAVSDPESS-AGHPVSGSS          210
mOR   KKTPSDLEGSGSPDILVRGDNDVPPFSGDGQHFMHIPGKGA-GSGPESS-TSRPLSGSS         223
hOR   KKIPSDFEGSGYTDLQERGDNDISPFSGDGQFFKDIPGKEATGPDLEGKDIQTGFAGPS         289 rOR   NVEIVDPHTNGLGSNEIPGREGHIGGAYATRGKTAQGAGSADVSLVEGSNEITGSTKFRE        270
mOR   KAEVIDPHMSGLGSNEIPGREGHGGSAYATRDKAAQGAGSAGGSLVGGSNEITGSTNFRE        283
hOR   EAESTHLDTKKPGYNEIPEREENGGNTIGTRDETAKEADAVDVSLVEGSNDIMGSTNEKE        349 rOR   LPGKEGNRVDASISQNAHQGKVEFHYPQAFSKEKVKCGSREHTGKAGYNEIPKSSKGASK        330
mOR   LPGKEGNRINAGSQNAHQGKVEFHYPQVASREKVKGG-VEHAGRAGYNEIPKSSKGSSSK       342
hOR   LPGREGNRVDAGSQNAHQGKVEFHYPPASKEKRKEGSSDAAESTNYNEIPKNGKGSTRK         409 rOR   DAEESKGNQVTLTESQRFPGKGKGQS----SHSIGNEVKSEEDSSN-----------SLSREG      378
mOR   DAEESKGNQLTLTASQRFPGKGKISQGPALPSHSISNEVKSEEN------------             385
hOR   GVDHSNRNQATLNEKQRFPSKGKISQGLPIPSRGLDNEIKNEMDSFNGPSHENIITHGRKY       469 rOR   IAIAHRRTSHPTRNRGMSQRRGSWASRRPHPHRRVSTRQRDSSESSSSGSSESSGD   435 (SEQ ID NO: 2)
mOR   HYVFHGQNNLTPNKGMSQRRGSWPSRRPNSHRRASTRQRDSSESSSSGSSESHGD   441 (SEQ ID NO: 4)
hOR   HYVFHRQNNS-TRNKGMPQGKGSWG-RQPHSNRRFSSRRDDSSESSDSGSSSESDGD 525 (SEQ ID NO: 6)
```

Kyte-Doolittle Hydrophobicity Plot

| Amino Acid(s) | Number count | % Frequency |
|---|---|---|
| Ala | 22 | 5.25 |
| Cys | 0 | 0.00 |
| Asp | 23 | 5.49 |
| Glu | 29 | 6.92 |
| Phe | 6 | 1.43 |
| Gly | 49 | 11.69 |
| His | 19 | 4.53 |
| Ile | 12 | 2.86 |
| Lys | 24 | 5.73 |
| Leu | 23 | 5.49 |
| Met | 3 | 0.72 |
| Asn | 22 | 5.25 |
| Pro | 26 | 6.21 |
| Gln | 21 | 5.01 |
| Arg | 30 | 7.16 |
| Ser | 59 | 14.08 |
| Thr | 23 | 5.49 |
| Val | 22 | 5.25 |
| Trp | 1 | 0.42 |
| Tyr | 5 | 1.82 |

FIG. 8

```
Osteoreg:  MQAVSVGLFLFSMTWAAP----KLNEDGSSGNQGNIHLASVKPEPMVGK----GTEGGR      52
           M+ V + FL+ ++ A P    +  E  SS  GN    LA  P PM        +E G
Dmp1:      MKTVILLTFLMWGLSCALPVARYQNTESESSEERTGN--LAQSPPPPMANSDHTDSSESGE     58

Osteoreg:  DAPLHLLDQNRQGATLLRNITQPVKSLV----TGTEVQSDRNKEKKPQSVLSVIPTDVHN    108
           +         Q R   L ++                +G  + D +     P+ + + +
Dmp1:      ELGSDR-SQYRPAGGLSKSAGMDADKEEDEDDSGDDTFGDEDNGPGPEERQWGGPSRLDS    117

Osteoreg:  TNDYSEDTENQQRDLLLQNSPGQSKHTPRARRSTHYLTHLPQIRKILSDFEDSASPDLLV    168
            D  S  DT   D    Q +     Q    TP   + H+          +DS S +  V
Dmp1:      DED-SADTTQSSEDSTSQENSAQD--TPSDSKD--HHSDEADSRPEAGDSTQDSESEEYRV    173

Osteoreg:  RGDNDVPPFSGDGQHFMHTPDRGGAVGSDP---ESSAGHPVSGSSNV---EIVDPH--TN    220
              G         GDG  F     D  G    DP     S  GH     S+++     E    H    T+
Dmp1:      GGGSEGESSHGDGSEF-----DDEGMQSDDPGSTRSDRGHTRMSSADISSEESKGDHEPTS    229

Osteoreg:  GLGSNEIPGREGHIGGAYATRGKTAQGAGSADVSLVEGSNEITGSTKFRELPGKEGNRVD    280
              S++        E    ++  R  ++        +      L  ++    T  S     +    KE +R  +
Dmp1:      TQDSDDSQDVEFSSRKSFR--RSRVSEEDDRGE--LADSNSRETQSVSTEDFRSKEESRSE    286

Osteoreg:  ASSQNAH-QGKVEFHYPQAPSKEKVK--GGSREHTGKAGYNEIPKSSKG------GA    328
            A  Q + +      QPS E  + G   + +         +           S+G    G
Dmp1:      TQEDTAETQSQEDSPEGQDPSSESEEAGEPSQESSSESQEGVASESRGDNPDNTSQTGD    346

Osteoreg:  SKDAEESKG---NQVTLTESQRFPGKGKGQSSHSLGNEVKSEEDSSN--SLSREGIAIAH    383
           +D+E S+      N + +ESQ     +G   +S+ SL       +S+E + +   S  S+EG+
Dmp1:      QRDSESSEEDRLNTFSSSESQSTEEQGDSESNESLSLSEESQESAQEDSSSQEGL----    402

Osteoreg:  RRTSHPTRNRGMSQRRGSWASRRPHPHRRVSTRQRDSSESSSSGSSSESSGD    435
              +++       S+     S  S+      R    R    DS  +SS  S     S S+G
Dmp1:      ------QSQSASRESRSQESQSEEDSRSEENRDSDSQDSSRKEESNSTGS    447
```

SEQ ID NO:2
SEQ ID NO:44

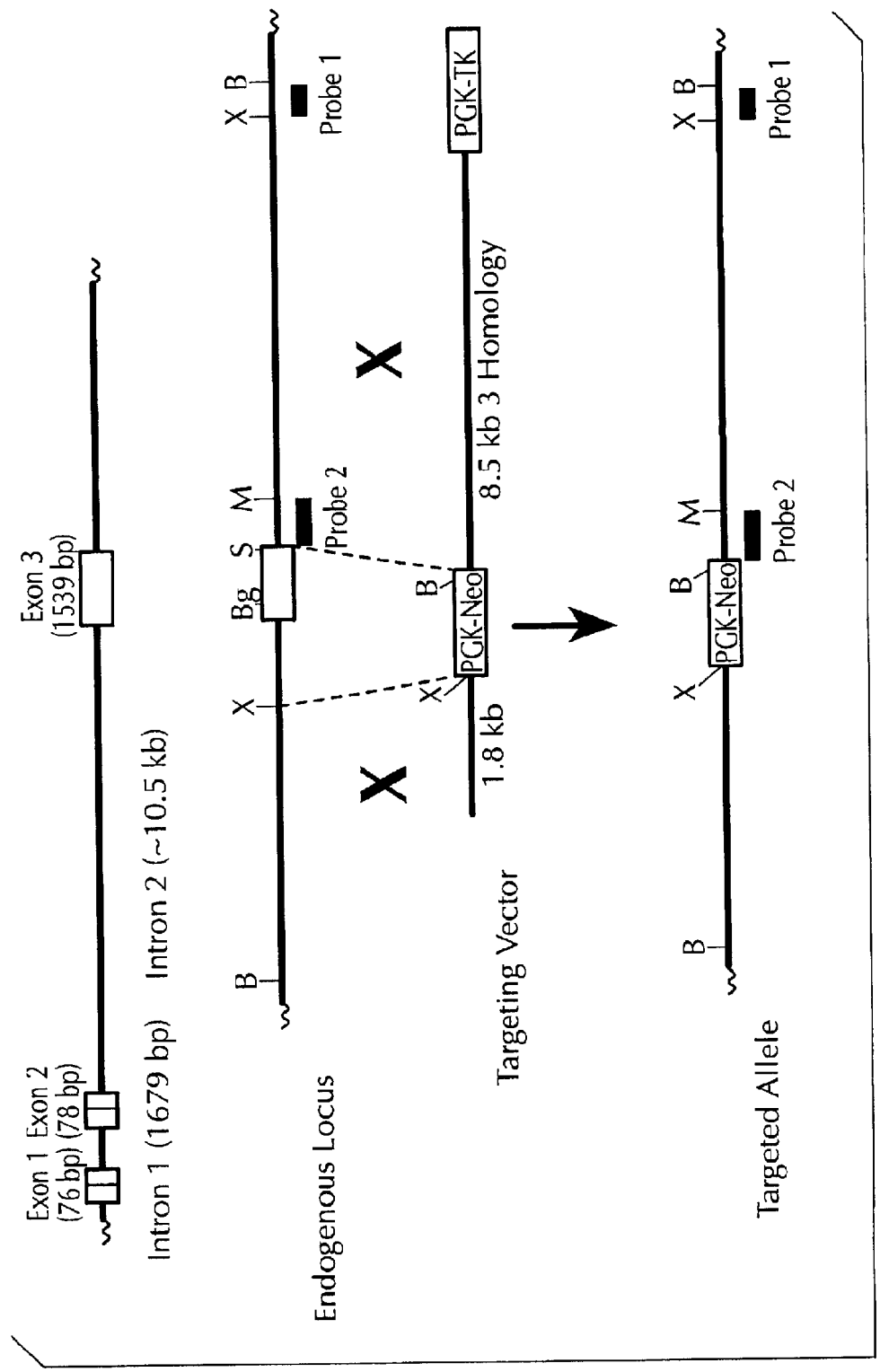

Trabecular Bone Volume-Males

Trabecular Bone Volume-Females

Trabecular Number-Males

Trabecular Number-Females

Trabecular Thickness-Females

Trabecular Thickness-Males

FIG. 21A (SEQ ID NO: 34)
APTFQPQTEKTKQSCVEEQRQEEKNKDNIGFHHLGKRINQELSSKENIVQERKKDLSLSEASENKGSSKSQNYFTNRQRLNKEYSISNKENTHNGLR
MSIYPKSTGNKGFEDGDDAISKLHDQEEYGAALIRNNMQHIMGPVTAIKLLGEENKENTPRNVLNIIPASMNYAKAHSKDKKKPQRDSQAQKSPVKS
KSTHRIQHNIDYLKHLSKVKKIPSDFEGSGYTDLQERGDNDISPFSGDGQPFKDIPGKGEATGPDLEGKDIQTGFAGPSEAESTHLDTKKPGYNEIP
EREENGGNTIGTRDETAKEADAVDVSLVEGSNDIMGSTNFKELPGREGNRVDAGSQNAHQGKVEFHYPPAPSKEKRKEGSSDAAESTNYNEIPKNGK
GSTRKGVDHSNRNQACLNEKQRFPSKGKSQGLPIPSRGLDNEIKNEMDSFNGPSHENIITHGRKYHYVPHRQNNSTRNKGMPQGKGSWGRQPHSNRR
FSSRRDDSSESSDSGSSESDGD

FIG. 21B (SEQ ID NO: 46)
APTFQPQTEKTKQSCVEEQRITYKGHYEKHGHYVFKCVYMSPEKKNQTDVKQEEKNKDNIGFHHLGKRINQELSSKENIVQERKKDLSLSEASENKG
SSKSQNYFTNRQRLNKEYSISNKENTHNGLRMSIYPKSTGNKGFEDGDDAISKLHDQEEYGAALIRNNMQHIMGPVTAIKLLGEENKENTPRNVLNI
IPASMNYAKAHSKDKKKPQRDSQAQKSPVKSKSTHRIQHNIDYLKHLSKVKKIPSDFEGSGYTDLQERGDNDISPFSGDGQPFKDIPGKGEATGPDL
EGKDIQTGFAGPSEAESTHLDTKKPGYNEIPEREENGGNTIGTRDETAKEADAVDVSLVEGSNDIMGSTNFKELPGREGNRVDAGSQNAHQGKVEFH
YPPAPSKEKRKEGSSDAAESTNYNEIPKNGKGSTRKGVDHSNRNQATLNEKQRFPSKGKSQGLPIPSRGLDNEIKNEMDSFNGPSHENIITHGRKYH
YVPHRQNNSTRNKGMPQGKGSWGRQPHSNRRFSSRRDDSSESSDSGSSSESDGD

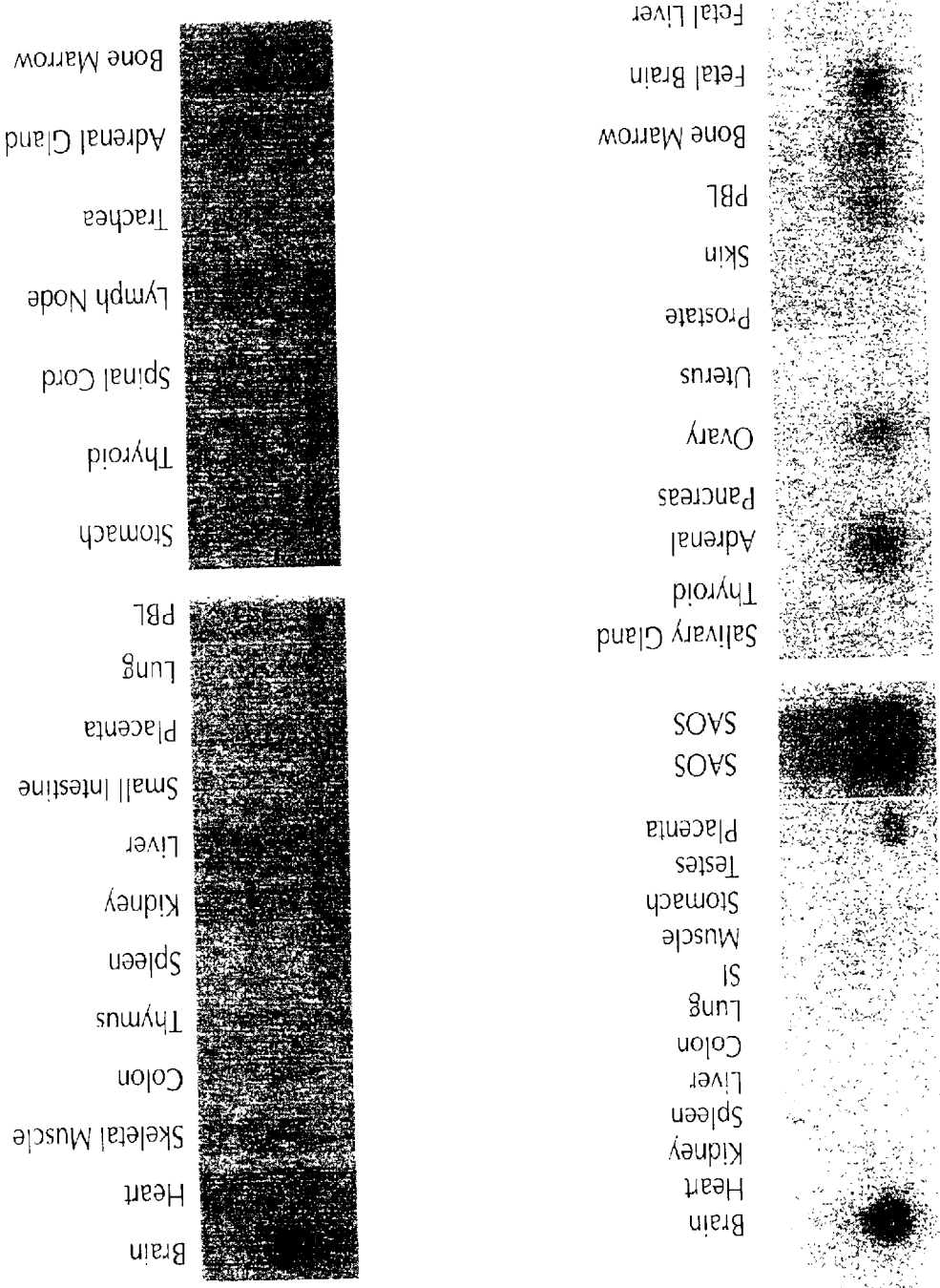

MAMMALIAN OSTEOREGULINS

This application claims priority, under 35 U.S.C. § 119(e), from U.S. provisional application No. 60/185,617, filed Feb. 29, 2000, and from U.S. provisional application No. 60/234,500, filed Sep. 22, 2000.

FIELD OF THE INVENTION

The invention is directed to novel osteoregulin polypeptides, which play a role in regulating bone homeostasis, adiposity, and the calcification of atherosclerotic plaques. The invention also features screening assays to identify modulators of osteoregulin activity as well as methods of treating mammals for diseases or disorders associated with osteoregulin activity.

BACKGROUND OF THE INVENTION

Bone is a highly dynamic tissue that undergoes continual processes of remodeling and modeling (Parfitt, J. Cellular Biochemistry 55: 273–86, 1994). In the growing skeleton, the amount of mineralized bone formed exceeds the amount lost through resorption, whereas in the mature adult, bone loss and bone formation are equivalent, thereby preserving the integrity of the skeleton. Under certain conditions such as aging, postmenopausal estrogen deficiency, or prolonged steroid treatment, the amount of bone formed is not sufficient to compensate for the quantity lost by resorption. Over time, this imbalance results in reduced bone mass and compromises the structural integrity of the skeleton.

Bone remodeling is a very complex process of tightly coordinated action by the bone resorbing osteoclasts and the bone forming osteoblasts. Osteoblasts are derived from a mesenchymal cell lineage and are responsible for the formation of new bone matrix in their differentiated state (Wlodarski, Clinical Orthopaedics & Related Research 276: 93, 1990). In addition, factors produced by osteoblasts regulate the formation of osteoclasts and osteoctastic bone resorbing activity in response to endocrine signals such as parathyroid hormone and vitamin D. It has been postulated that the bone loss associated with aging is a result of a defect in the osteoblast cell lineage (Rodriguez et al., J. of Cellular Biochemistry 75: 414–423, 1999; Erdmann et al., Mechanisms of Aging & Development 110: 73–85, 1999; Roholl et al., J. of Bone & Mineral Research 9: 355–66, 1994; Katzburg et al., Bone 25: 667–673, 1999). Either the mesenchymal precursor population is insufficient or has lost the capacity to proliferate and differentiate into sufficient numbers of functioning osteoblasts.

Osteoblasts progress through a 3 stage process of differentiation: proliferation, matrix maturation, and mineralization (Aubin, Journal of Cellular Biochemistry 72: 396–410, 1999; Stein and Lian, Endocrine Reviews 14: 424–42, 1993; Malaval et al., J. of Cellular Biochemistry 74: 616–27, 1999). During this differentiation process, a well characterized temporal and spatial expression pattern of extracellular bone matrix proteins and other genes occurs (Malaval et al., J. of Cellular Biochemistry 74: 616–27, 1999; Owen et al., J. of Cellular Physiology 143: 420–30, 1990; Ingram et al., J. of Bone & Mineral Research 8: 1019–29, 1993). The bone matrix is composed primarily of Type I collagen which forms the extracellular structural component for the deposition of mineral forming hydroxyapatite. Osteoblasts also secrete non-collagenous proteins into the extracellular matrix (Robey, Connective Tissue Research 35: 131–6, 1996; Boskey, Connective Tissue Research 35: 357–63, 1996). The non-collagenous proteins include proteoglycans, sulfated glycoproteins, highly phosphorylated RGD-motif proteins, and proteins modified to contain gla amino acid residues. Examples include biglycan, osteonectin, bone sialoprotein, osteopontin, and osteocalcin. The exact function of many of these proteins have not yet been delineated although most evidence supports their role in promoting mineralization events (Robey, Connective Tissue Research 35: 131–6, 1996). An exception is the gla-peptide, osteocalcin, which has been shown to be a negative regulator of bone formation by gene knockout technology (Ducy et al.; Nature 382: 448–52, 1996).

The progression of osteoblast differentiation has been modeled in cell culture using primary calvarial cells or bone marrow cells. Bone marrow contains pluripotent stem cells of the adipocytic, osteoblastic, fibroblastic, and hematopoetic cell lineage (Owen et al., J. of Cellular Physiology 143: 420–30, 1990; Beresford, J. of Cell Science 102: 341–51, 1992: Herbertson and Aubin, Bone 21: 491–500, 1997). Bone marrow from rats, mice, and humans has been shown to contain osteoprogenitor cells that proliferate and can be induced to differentiate into osteoblastic cells. Rat and human cultures require a differentiation agent such as dexamethasone whereas mouse-derived cells can differentiate in the absence of dexamethasone (Rickard et al., J. of Bone & Mineral Research 11: 312–24, 1996; Maniatopoulos et al., Cell & Tissue Research 254: 317–30, 1988; Chen et al., Endocrinology 112: 1739–45, 1983). In vitro differentiated osteoblasts display the capacity to secrete noncollagenous proteins into the extracellular matrix in a temporally regulated manner which may indicate a regulatory function for each of these proteins in the mineralization process (Yao et al., J. of Bone & Mineral Research 9: 231–40, 1994). Furthermore, differentiated bone marrow cultures have the capacity to facilitate the deposition of matrix and the formation of hydroxyapatite mineral when grown in the presence of a phosphate source such as $\beta$-glycerophosphate. These properties have made the differentiation of bone marrow cells a useful model to investigate the mechanisms of bone remodeling and osteoblast function.

Osteoporosis accounts for approximately 700,000 fractures per year in the United States alone, and osteoporotic fractures are linked to significant death and is morbidity in the aged population. Therefore, there is a clear need to further understand the process of bone remodeling, both in normal and pathological states, in order to develop therapeutic agents to prevent, reduce, or reverse bone loss associated with osteoporosis or other bone-related disorders.

SUMMARY OF THE INVENTION

We sequenced a novel cDNA transcript expressed specifically in rat osteoblasts and osteocytes that encodes a 45 kDa polypeptide; and we have also identified the mouse and human forms. Our characterization revealed the protein to be a secreted, RGD motif containing protein with a limited homology to dmp1, an extracellular matrix protein present in bone and teeth (Roholl et al., J. of Bone & Mineral Research 9: 355–66, 1994; Katzburg et al., Bone 25: 667–673, 1999). Thus, we have designated this mammalian protein "osteoregulin." Further studies of osteoregulin expression patterns and function (as further described in the detailed description) have confirmed that osteoregulin plays an important role in controlling bone homeostasis, adipose regulation, and the calcification of atherosclerotic plaques.

The invention features novel osteoregulin polypeptides, the nucleotide sequences that encode them, expression vectors containing these osteoregulin sequences, and transgenic hosts which have been genetically modified to express the osteoregulins of the invention.

Another feature of the invention is non-human mammals and animal cells that have been genetically-modified to disrupt one or both copies of an endogenous osteoregulin gene. Studies of genetically-modified mice that are homozygous or heterozygous for the osteoregulin gene disruption demonstrate that the absence or reduction of osteoregulin gene expression results in increased bone mass, increased bone mineralization, increased bone formation, and an increase in adiposity in females. These phenotypes indicate that osteoregulin functions as a negative regulator of bone mass/density and adiposity. This role in bone homeostasis is further supported by the significant expression of osteoregulin in bone tissue as well as osteoregulin's similarities to other proteins that play a role in regulating bone function.

Given the discovered function of osteoregulins as negative regulators of bone formation, bone density, bone mineralization, as well as its role in adiposity and plaque calcification, the present invention also features screening assays to identify agents that modulate osteoregulin activity or gene expression. Such agents are useful for administering to mammals, preferably humans, for the treatment of bone disorders, such as osteoporosis, to stimulate bone repair or regeneration, and to treat disorders related to adiposity or the calcification of atherosclerotic plaques.

In its first aspect, the invention features an isolated or purified polypeptide, or a heterologous polypeptide, wherein the polypeptide has osteoregulin activity and contains: the amino acid sequence of SEQ ID NO: 2, 4, 6, 8, 34, or 46; an amino acid sequence encoded by a polynucleotide which will hybridize under highly stringent conditions with a probe having the complement of the coding sequence shown in SEQ ID NO: 1, 3, 5, 7, 33; or 45; or an amino acid sequence having at least 90% identity, more preferably, 95% identity, to an amino acid sequence containing SEQ ID NO: 2, 4, 6, 8, 34, or 46. Preferably, the polypeptide is mammalian and/or naturally occurring.

In a second, related aspect, the invention features an isolated or purified polynucleotide containing: the coding sequence of SEQ ID NO: 1, 3, 5, 7, 33, or 45; a sequence encoding any of the polypeptides above, preferably SEQ ID NO: 2, 4, 6, 8, 34, or 46; or a sequence which hybridizes, under highly stringent conditions, to a probe, preferably to the full length of a probe, having the complement of any of the above-mentioned polynucleotides. Preferably, the sequence hybridizes to the complement of the coding sequence shown in SEQ ID NO: 1, 3, 5, 7, 33, or 45, or the sequence is present in a mammalian cDNA library.

The invention also features an antibody that selectively binds to a polypeptide of the invention, preferably SEQ ID NO: 2, 4, 6, 8, 34, or 46, a vector containing a polynucleotide of the invention, preferably SEQ ID NO: 1, 3, 5, 7, 33, or 45, and a transgenic host expressing a polynucleotide of the invention, preferably the coding sequence shown in SEQ ID NO: 1, 3, 5, 7, 33, or 45. The preferred host is a transfected mammalian host cell or a transgenic mammal (e.g., mouse, rat, pig, sheep, monkey).

Another aspect of the invention is a genetically-modified, non-human mammal, wherein the modification results in a functionally disrupted osteoregulin gene. The mammal may be heterozygous for the modification, or homozygous for the modification. Preferably, the mammal is a rodent, more preferably, a mouse. In a related aspect, the invention also provides a genetically-modified animal cell, wherein the modification comprises a functionally disrupted osteoregulin gene. The cell is heterozygous or homozygous for the modification. Preferably, the animal cell is an embryonic stem (ES) cell or an ES-like cell, the cell is human, or the cell is murine.

A method of screening for an agent that modulates osteoregulin activity (e.g., affecting the regulation of bone mass, bone density, adiposity, vascular flexibility, and/or atherosclerotic plaque calcification) is an additional feature of the invention, the method comprises contacting an agent with an osteoregulin polypeptide and measuring the activity of the osteoregulin, wherein a difference between the osteoregulin activity in the presence of the agent and in the absence of the agent is indicative that the agent modulates the activity.

Also featured is a method of screening for an agent that modulates any of the above-mentioned osteoregulin activities by regulating osteoregulin expression, the method comprises contacting an agent with a cell containing a nucleotide sequence containing an osteoregulin gene regulatory element (e.g., an osteoregulin promoter sequence) operably linked to a coding sequence, and measuring the expression of the coding sequence, wherein a difference between the expression in the presence of the agent and in the absence of the agent is indicative that the agent modulates osteoregulin expression.

The invention also provides a method of treating a mammal to regulate bone mass and/or density, adiposity, vascular flexibility, and/or atherosclerotic plaque calcification, the method comprises administering an osteoregulin modulator to the mammal. Preferably, the modulator is an osteoregulin antagonist and is administered to increase bone mass and/or bone density, the modulator is an osteoregulin agonist and is administered to reduce adiposity; the modulator is an osteoregulin antagonist and is administered to increase atherosclerotic plaque stability by increasing plaque calcification (e.g., to prevent stroke); or the modulator is an osteoregulin agonist wherein the agonist is administered to increase vascular flexibility by decreasing atherosclerotic plaque calcification.

An additional aspect of the invention features a method for producing a polypeptide of claim 3 or 4. The method comprises (a) culturing a cell under conditions suitable for expression of the polypeptide, wherein said cell comprises a heterologous polynucleotide that encodes said polypeptide and said polynucleotide is operably linked to a promoter sequence; and (b) recovering said polypeptide. Preferably, the polynucleotide comprises SEQ ID NO: 1, 3, 5, or 7, or, in the case where the cell is a bacterial cell, a preferred polynucleotide comprises SEQ ID NO: 33 or SEQ ID NO: 45, or rat or mouse nucleic acid sequence encoding an osteoregulin polypeptide lacking the N-terminal signal sequence.

Those skilled in the art will fully understand the terms used herein in the description and the appendant claims to describe the present invention. Nonetheless, unless otherwise provided herein, the following terms are as described immediately below.

"Osteoregulin activity" is the negative regulation of bone mineralization, bone density, and/or bone formation. Thus, an osteoregulin functions to decrease bone area, bone mineral content, bone mineral density, and/or bone density. "Osteoregulin activity" also includes the negative regulation of the calcification of atherosclerotic plaques and the stimulation of increased adiposity. A polypeptide with "osteoregulin activity" exhibits at least one of these activities.

An osteoregulin "agonist" refers to a molecule which intensifies or mimics the biological activity of an osteoregulin. Agonists may include proteins, nucleic acids, carbohydrates, small molecules, or any other compound or composition which increases the activity of an osteoregulin either by increasing the amount of osteoregulin present in a cell or by increasing the signaling of an osteoregulin polypeptide in its signal transduction pathway.

An "allelic variant" is an alternative form of the gene encoding an osteoregulin. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to naturally-occurring deletions, additions, or substitutions of nucleotide. Each of these types of changes may occur alone, or in combination with the others, one or more times in a given sequence.

"Altered" nucleic acid sequences encoding an osteoregulin include those sequences with deletions, insertions, or substitutions of different nucleotides, resulting in a polypeptide with at least one functional characteristic of an osteoregulin. Included within this definition are polymorphisms which may or may not be readily detectable using a particular oligonucleotide probe of the polynucleotide encoding an osteoregulin. The encoded protein may also be "altered," and may contain deletions, insertions, or substitutions of amino acid residues which produce a silent change and result in a functionally equivalent osteoregulin. Deliberate amino acid substitutions may be made on the basis of similarity in polarity, charge, solubility, hydrophobicity, hydrophilicity, and/or the amphipathic nature of the residues, as long as the biological or immunological activity of the osteoregulin is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

"Amplification" relates to the production of additional copies of a nucleic acid sequence. It is generally carried out using polymerase chain reaction (PCR) technologies well known in the art.

An osteoregulin "antagonist" refers to a molecule which inhibits or attenuates the biological activity of an osteoregulin. Antagonists may include proteins such as anti-osteoregulin antibodies, nucleic acids, carbohydrates, small molecules, or any other compound or composition which decreases the activity of an osteoregulin either by reducing the amount of osteoregulin present in a cell, or by decreasing the signaling of an osteoregulin polypeptide in its signal transduction pathway.

The term "antibody" refers to intact immunoglobulin molecules as well as to fragments thereof, such as Fab, F(ab')2, and Fv fragments, which are capable of binding an epitopic determinant. Antibodies that bind osteoregulin polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin. The coupled peptide is then used to immunize the animal.

The term "biologically active" refers to a protein having structural, regulatory, or biochemical functions of a naturally occurring molecule. Likewise, "immunologically active" refers to the capability of the natural, recombinant, or synthetic osteoregulin, or of any oligopeptide thereof, to induce a specific immune response in appropriate animals or cells and to bind with specific antibodies.

A "composition" comprising a given polynucleotide or amino acid sequence refers broadly to any composition containing the given polynucleotide or amino acid sequence. The composition may comprise a dry formulation or an aqueous solution.

"Conservative amino acid substitutions" are those substitutions that, when made, least interfere with the properties of the original protein, i.e., the structure and especially the function of the protein is conserved and not significantly changed by such substitutions. Table A below shows amino acids which may be substituted for an original amino acid and which are regarded as conservative amino acid substitutions.

TABLE A

Conservative Amino Acid Substitutions

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The term "derivative" refers to the chemical modification of a polypeptide sequence, or a polynucleotide sequence. Chemical modifications of a polynucleotide sequence can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "fragment" is a unique portion of an osteoregulin or the polynucleotide encoding an osteoregulin which is identical in sequence to but shorter in length than the parent sequence. A fragment used as a probe, primer, antigen, therapeutic molecule, or for other purposes, may be at least 5, 10, 15, 20, 25, 30, 40, 50, 60, 75, 100, 150, 250 or at least 500 contiguous nucleotides or amino acid residues in length. Fragments may be preferentially selected from, or lack, certain regions of a molecule. For example, an osteoregulin polypeptide fragment may be the N-terminal signal sequence of an osteoregulin, such as amino acids 1–16 of SEQ ID NO: 2, 4, 6, or 8, or a fragment may contain an RGD motif.

The term "identity" refers to a degree of complementarity. There may be partial similarity or complete identity. The word "similarity" may substitute for the word "identity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted. Rather, reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins and Sharp CABIOS 5:151–153, 1989 and in Higgins et al. CABIOS 8:189–19, 1992. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequence pairs. Alternatively, a suite of commonly used and freely available sequence comparison algorithms is provided by the National Center for Biotechnology Information (NCBI) Basic Local Alignment Search Tool (BLAST) (Altschul et al., J. Mol. Biol. 215:403–410, 1990), which is available from several sources, including the NCBI, Bethesda, MID, and at http://www.ncbi.nim.nih.lzov/13LAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at http://www.ncbi.nim. nih.lzov/gorf/b12.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.9 (May 7, 1999) set at default parameters. Such default parameters may be, for example Matrix: BLOSUM62 Rewardfor match: 1 Penaltyfor mismatch: -2 Open Gap: 5 and Extension Gap.-2 penalties Gap x drop-off.-50 Expect 10 Word Size: 1 Filter: on. Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length disclosed by the sequences shown herein may be used to describe a length over which percentage identity may be measured. Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences encompassed by the invention that all encode substantially the same osteoregulin protein.

The phrases "percent identity" and "% identity," as applied to polypeptide sequences, refer to the percentage of residue matches between at least two polypeptide sequences aligned using a standardized algorithm. Methods of polypeptide sequence alignment are well known. Some alignment methods take into account conservative amino acid substitutions. Such conservative substitutions, explained in more detail above, generally preserve the hydrophobicity and acidity at the site of substitution, thus preserving the structure and function of the polypeptide. Percent identity between polypeptide sequences may be determined using the default parameters of the CLUSTAL V algorithm as incorporated into the MegAlign® sequence alignment program (DNASTAR, Madison, Wis.). For pairwise alignments of polypeptide sequences using CLUSTAL V, the default parameters are set as follows: Ktuple=1, gap penalty-3, window-5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.9 (May 7, 1999) with blastp set at default parameters. Such default parameters may be, for example, Matrix: BLOSUM62 Open Gap: 11 and Extension Gap: 1 penalties Gap x drop-off: 50 Expect: 10 Word Size: 3 Filter: on. Percent identity may be measured over the length of an entire defined polypeptide sequence, for example, as defined by a particular SEQ ID number (e.g., 2, 4, 6, 8, or 10), or may be measured over a shorter length, for example, over the length of a fragment taken from a larger, defined polypeptide sequence, for instance, a fragment of at least 15, at least 20, at least 30, at least 40, at least 50, at least 70 or at least contiguous residues. Such lengths are exemplary only, and it is understood that any fragment length supported by the sequences shown herein, in the tables, figures or Sequence Listing, may be used to describe a length over which percentage identity may be measured.

By a "host" is meant a transgenic cell (e.g., mammalian, bacterial, insect) or an animal (e.g., non-human mammal) that is transfected with, and capable of expressing, a heterologous polynudeotide.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to an originally non-human antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of identity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 pg/ml denatured salmon sperm DNA.

Generally, stringency of hybridization is expressed, in part, with reference to the temperature under which the wash step is carried out. Generally, such wash temperatures are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. An equation for calculating Tm and conditions for nucleic acid hybridization are well known and can be found in Sambrook et al., 1989, Molecular Cloning: A Laboratory Manual, $2^{nd}$ ed., vol. 1–3, Cold Spring Harbor Press, Plainview, N.Y.; specifically see volume 2, chapter 9.

High stringency conditions for hybridization between polynucleotides of the present invention include wash conditions of about 55–68° C. in the presence of about 0.2–1.0× SSC and about 0.1% SDS, for 1 hour.

In general, hybridization reactions can be carried out at temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, denatured salmon sperm DNA at about 100–200 pg/ml. Organic solvent, such as formamide at a concentration of about 35–50% v/v, may also be used under particular circumstances, such as for RNA:DNA hybridizations. Useful variations on these wash conditions will be readily apparent to those of ordinary skill in the art. Hybridization, particularly under high stringency conditions, is suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed between sequences present in solution or formed between one nucleic acid sequence present in solution and another nucleic acid sequence immobilized on a solid support (e.g., paper, membranes, filters, chips, pins or glass slides).

By "isolated or purified" is meant changed from the natural state "by the hand of man." If a polynudeotide or polypeptide exists in nature, then it is "isolated or purified" if it is changed and/or removed from As original environment. For example, an "isolated or purified" polynucleotide is separated from other polynucleotide sequence with which it is associated in nature. For example, a cDNA sequence is removed from intronic sequence normally associated with the coding sequence contained in the cDNA. Such a sequence may be introduced into another cell for recombinant expression. However, polynucleotide sequences as found in cDNA libraries are excluded from what is meant by "isolated or purified." An "isolated or purified" polypeptide is separated from at least one cellular component with which it is associated in nature. Preferably, the polypeptide is at least 60% free, more preferably, at least 75% free, and, most preferably, at least 90% from from other components.

"Operably linked" refers to the situation in which a first nucleic acid sequence is placed in a functional relationship with the second nucleic acid sequence. For example, a promoter is operably linked to a coding sequence if the promoter functions to regulate transcription or expression of the coding sequence. Generally, operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Polynucleotide" generally refers to any RNA (e.g., mRNA), RNA-like, DNA (e.g., cDNA or genomic), or DNA like sequences, including, without limit, single-stranded, double-stranded, and triple-stranded sequence, senst or anti-sense strands, sequence generated using nucleotide analogs, hybrid molecules comprising RNA and DNA, and RNA or DNA containing modified bases. The polynucleotide can be naturally-occurring or synthesized.

The term "polypeptide" refers to an amino acid sequence, oligopeptide, peptide, polypeptide, or protein sequence, or a fragment of any of these, and to naturally occurring or synthetic molecules. It includes amino acid sequences modified either by natural processes, such as post-translational processing, or by chemical modifications well known in the art (see, e.g., *Proteins—Structure and Molecular Properties*, Ed. Creighton, W. H. Freeman and Co., New York, N.Y., $2^{nd}$ Ed, 1993; *Posttransiational covalent Modification of Proteins*, Ed. Johnson, Academic Press, New York, N.Y., 1983; Seifter et al., Meth. Enzymol., 182: 626–46, 1990; and Rattan et al., Ann. NY Acad. Sci. 663: 48–62, 1992).

"Probes" refer to nucleic acid sequences encoding osteoregulins, their complements, or fragments thereof, which are used to detect identical, allellic or related nucleic acid sequences. Probes are isolated oligonucleotides or polynucleotides attached to a detectable label or reporter molecule. Typical labels include radioactive isotopes, ligands, chemiluminescent agents, and enzymes.

"Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length disclosed by the specification, including the tables, figures, and Sequence Listing, may be used.

Methods for preparing and using probes and primers are described in the literature (e.g., Sambrook et al., *Molecular Cloning: A Laboratory Manual*, $2^{nd}$ ed., vol. 1–3, Cold Spring Harbor Press, Plainview, N.Y. 1989; Ausubel et al., *Current Protocols in Molecular Biology*, Greene Publ. Assoc. & Wiley-Intersciences, New York, N.Y. 1987; and Innis et al., *PCR Protocols—A Guide to Methods and Application*, Academic Press, San Diego, Calif. 1990). PCR primer pairs can be derived from a known sequence, for example, by using computer programs intended for that purpose (e.g., Primer, Version 0.5, 1991, Whitehead Institute for Biomedical Research, Cambridge, Mass.).

Oligonucleotides for use as primers are selected using software known in the art for such purpose. For example, OLIGO 4.06 software Is useful for the selection of PCR primer pairs and for the analysis of oligonucleotides and larger polynucleotides of up to nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "substitution" refers to the replacement of one or more amino acids or nucleotides by different amino acids or nucleotides, respectively.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9, set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPS) in which the polynucleotide sequence varies by one nucleotide base. The presence of SNPs may be indicative of, for example, a certain population, a disease state, or a propensity for a disease state.

"Transformation" or "transfection" describes a process of genetic modification by which heterologous (i.e., foreign or exogenous) DNA enters and renders a recipient cell capable of expressing the heterologous DNA. Transformation may occur according to various methods well known in the art, for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. The terms "transformed cells" or "transfected cells" include stably transformed cells in which the inserted DNA is capable of replication either as an autonomously replicating plasmid or as part of the host chromosome, as well as transiently transformed or transfected cells which express the inserted DNA or RNA for limited periods of time. All of such transformed or transfected cells are referred to as "transgenic."

A non-human mammal or an animal cell that is "genetically-modified" is heterozygous or homozygous for a modification that is introduced into the non-human mammal or animal cell, or into a progenitor non-human mammal or animal cell, by genetic engineering. The standard methods of genetic engineering that are available for introducing the modification include homologous recombination, viral vector gene trapping, irradiation, chemical mutagenesis, and the transgenic expression of a nucleotide sequence encoding antisense RNA alone or in combination with catalytic ribozymes. Preferred methods for genetic modification to disrupt a gene are those which modify an endogenous gene by inserting a "foreign nucleic acid sequence" into the gene locus, e.g., by homologous recombination or viral vector gene trapping. A "foreign nucleic acid sequence" is an exogenous sequence that is non-naturally occurring in the gene. This insertion of foreign DNA can occur within any region of the osteoregulin gene, e.g., in an enhancer, promoter, regulator region, noncoding region, coding region, intron, or exon. The most preferred method of genetic engineering for gene disruption is homologous recombination, in which the foreign nucleic acid sequence is inserted in a targeted manner either alone or in combination with a deletion of a portion of the endogenous gene sequence.

By an osteoregulin gene that is "functionally disrupted" is meant an osteoregulin gene that is genetically modified such that the cellular activity of the osteoregulin polypeptide encoded by the disrupted gene is decreased or eliminated in cells that normally express a wild type version of the osteoregulin gene. When the genetic modification effectively eliminates all wild type copies of the osteoregulin gene in a cell (e.g., the genetically-modified, non-human mammal or animal cell is homozygous for the osteoregulin gene disruption or the only wild type copy of osteoregulin gene originally present is now disrupted), then the genetic modification results in a reduction in osteoregulin polypeptide activity as compared to an appropriate control cell that expresses the wild type osteoregulin gene. This reduction in osteoregulin polypeptide activity results from either reduced osteoregulin gene expression (i.e., osteoregulin mRNA levels are effectively reduced and produce reduced levels of osteoregulin polypeptide) and/or because the disrupted osteoregulin gene encodes a mutated polypeptide with reduced function or stability as compared to a wild type osteoregulin polypeptide. Preferably, the activity of osteoregulin polypeptide in the genetically-modified, non-human mammal or animal cell is reduced to 50% or less of wild type levels, more preferably, to 25% or less, and, even more preferably, to 10% or less of wild type levels. Most preferably, the osteoregulin gene disruption results in non-detectable osteoregulin activity.

By a "genetically-modified, non-human mammal" containing a functionally disrupted osteoregulin gene is meant a non-human mammal that is originally produced, for example, by creating a blastocyst or embryo carrying the desired genetic modification and then implanting the blastocyst or embryo in a foster mother for in utero development. The genetically-modified blastocyst or embryo can be made, in the case of mice, by implanting a genetically-modified embryonic stem (ES) cell into a mouse blastocyst or by aggregating ES cells with tetraploid embryos. Alternatively, various species of genetically-modified embryos can be obtained by nuclear transfer. In the case of nuclear transfer, the donor cell is a somatic cell or a pluripotent stem cell, and it is engineered to contain the desired genetic modification that functionally disrupts the osteoregulin gene. The nucleus of this cell is then transferred into a fertilized or parthenogenetic oocyte that is enucleated, the embryo is reconstituted, and developed into a blastocyst. A genetically-modified blastocyst produced by either of the above methods is then implanted into a foster mother according to standard methods well known to those skilled in the art. A "genetically-modified, non-human mammal" includes all progeny of the mammals created by the methods described above, provided that the progeny inherit at least one copy of the genetic modification that functionally disrupts the osteoregulin gene. It is preferred that all somatic cells and germline cells of the genetically-modified mammal contain the modification. Preferred non-human animals that are genetically-modified to contain a disrupted osteoregulin gene include rodents, such as mice and rats, cats, dogs, rabbits, guinea pigs, hamsters, sheep, pigs, and ferrets.

By a "genetically-modified animal cell" containing a functionally disrupted osteoregulin gene is meant an animal cell, including a human cell, created by genetic engineering to contain a functionally disrupted osteoregulin gene, as well as daughter cells that inherit the disrupted osteoregulin gene. These cells may be genetically-modified in culture according to any standard method known in the art. As an alternative to genetically modifying the cells in culture, non-human mammalian cells may also be isolated from a genetically-modified, non-human mammal that contains an osteoregulin gene disruption. The animal cells of the invention may be obtained from primary cell or tissue preparations as well as culture-adapted, tumorigenic, or transformed cell lines. These cells and cell lines are derived, for example, from endothelial cells, epithelial cells, islets, neurons and other neural tissue-derived cells, mesothelial cells, osteocytes, lymphocytes, chondrocytes, hematopoietic cells, immune cells, cells of the major glands or organs (e.g., testicle, liver, lung, heart, stomach, pancreas, kidney, and skin), muscle cells (including cells from skeletal muscle, smooth muscle, and cardiac muscle), exocrine or endocrine cells, fibroblasts, and embryonic and other totipotent or pluripotent stem cells (e.g., ES cells, ES-like cells, and embryonic germline (EG) cells, and other stem cells, such as progenitor cells and tissue-derived stem cells). The preferred genetically-modified cells are ES cells, more preferably, mouse or rat ES cells, and, most preferably, human ES cells.

By an "ES cell" or an "ES-like cell" is meant a pluripotent stem cell derived from an embryo, from a primordial germ cell, or from a teratocarcinoma, that is capable of indefinite self renewal as well as differentiation into cell types that are representative of all three embryonic germ layers.

By "modulates" is meant increases or decreases (including a complete elimination).

Other features and advantages of the invention will be apparent from the following detailed description and from the claims. While the invention is described in connection with specific embodiments, it will be understood that other changes and modifications that may be practiced are also part of this invention and are also within the scope of the appendant claims. This application is intended to cover any equivalents, variations, uses, or adaptations of the invention that follow, in general, the principles of the invention, including departures from the present disclosure that come within known or customary practice within the art, and that are able to be ascertained without undue experimentation. Additional guidance with respect to making and using nucleic acids and polypeptides is found in standard textbooks of molecular biology, protein science, and immunology (see, e.g., Davis et al., Basic Methods in Molecular Biology, Elsevir Sciences Publishing, Inc., New York, N.Y., 1986; Hames et al., Nucleic Acid Hybridization, IL Press, 1985; Molecular Cloning, Sambrook et al., Current Protocols in Molecular Biology, Eds. Ausubel et al., John Wiley and Sons; Current Protocols in Human Genetics, Eds. Dracopoli et al., John Wiley and Sons; Current Protocols in Protein Science, Eds. John E. Coligan et al., John Wiley and Sons; and Current Protocols in Immunology, Eds. John E. Coligan et al., John Wiley and Sons). All publications mentioned herein are incorporated by reference in their entireties.

DESCRIPTION OF THE FIGURES

FIG. 1A shows the nucleotide sequence encoding rat osteoregulin (SEQ ID NO: 1). FIG. 1B shows the predicted amino acid sequence (SEQ ID NO: 2). A signal sequence is underlined.

FIG. 2A details the nucleotide sequence encoding mouse osteoregulin (SEQ ID NO: 3). FIG. 2B describes the predicted amino acid sequence (SEQ ID NO: 4).

FIG. 3A shows a nucleotide sequence encoding a human osteoregulin (SEQ ID NO: 5). FIG. 3B shows the predicted amino acid sequence (SEQ ID NO: 6).

FIG. 4A describes another nucleotide sequence encoding a human osteoregulin (SEQ ID NO: 7). FIG. 4B describes the predicted amino acid sequence (SEQ ID NO: 8).

FIG. 5 is a schematic showing the alignment between rat, mouse, and human osteoregulin polypeptides. A conserved RGD motif is underlined.

FIG. 8 shows the alignment between rat osteoregulin amino acid sequence and the dentin and bone matrix protein DMP1/AG1, showing weak homology. The rat osteoregulin primary amino acid sequence was aligned with the first 447 amino acids of rat DMP (SEQ ID NO: 43).

FIG. 9 depicts the highly specific bone tissue osteoregulin mRNA expression pattern in rat.

FIG. 14 shows the genomic organization and the strategy for targeted disruption of the murine osteoregulin gene. Exon sizes and intron/exon boundaries of the mouse osteoregulin gene are diagrammed. Recombination of the targeting vector with the osteoregulin locus results in the replacement of the third and largest exon with the neomycin selectable marker gene. Successful targeting was detected with both external (probe 1) and internal (probe 2) probes. X=Xba1, Bg=BgI II, Sp=SpeI, M=Msc I, B=Bam HI.

FIG. 21A shows the amino acid sequence for a human osteoregulin polypeptide which lacks an N-terminal signal sequence (SEQ ID NO: 34). The amino acid sequence is encoded by SEQ ID NO: 33. FIG. 21B shows the amino acid sequence for a second human osteoregulin polypeptide which lacks an N-terminal signal sequence (SEQ ID NO: 46). The amino acid sequence is encoded by SEQ ID NO: 45.

FIG. 22 is a Northern blot showing the tissue distribution of human osteoregulin expression. Other tissues not shown, but negative for expression, include prostate, testes, and ovary.

FIG. 23 shows osteoregulin tissue expression by Southern blot analysis of RT-PCR.

DETAILED DESCRIPTION

Figure 6:
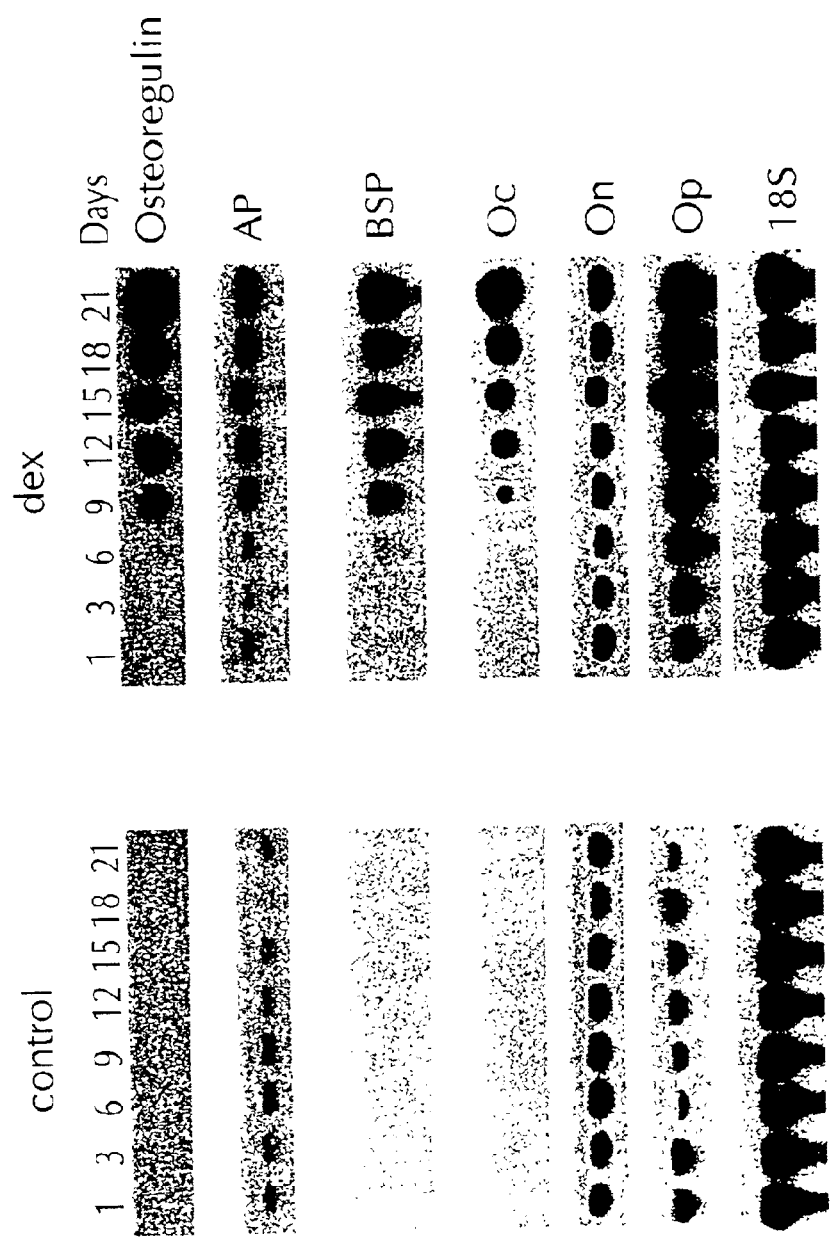
FIG. 6 is a Northern blot showing osteoregulin mRNA increase during differentiation of rat bone marrow cell cultures into osteoblastic cells by dexamethasone treatment. 20 µg of total RNA from either control or dexamethasone treated rat bone marrow cell cultures was subjected to Northern blot analysis at the indicated time points. Filters were probed sequentially for alkaline phosphatase (AP), bone sialoprotein (BSP), osteocalcin (Oc), osteonectin (On), osteopontin (Op) and the control 18S rRNA (18S).

The invention is directed to new mammalian proteins, designated osteoregulins, the polynucleotides encoding the osteoregulins, genetically-modified non-human mammals and animal cells containing a disrupted osteoregulin gene, and host cells transfected with, and expressing an exogenous osteoregulin protein.

We have discovered that osteoregulins play a role in regulating bone density, bone mineralization, and the level of adiposity. Accordingly, additional features of the invention provide, first, for screening assays that identify agents that modulate osteoregulin activity and/or expression, and, second, for the use of agents that regulate osteoregulin activity or expression to treat or prevent bone or adipose tissue related disorders.

Osteorequlin Amino Acid Sequences and Nucleotide Sequences

The invention encompasses osteoregulin polypeptide sequences, for example, rat osteoregulin (FIG. 1B, SEQ ID NO: 2), mouse osteoregulin (FIG. 2B, SEQ ID NO: 4), and human osteoregulin (FIGS. 3B, 4B, 21A and 21B, SEQ ID NOs: 6, 8, 34, and 46, respectively), and any variant, homologue, fragment, or derivative thereof.

All of the disclosed osteoregulin sequences are rich in serine, glycine, and charged amino acids, and include a charged amino terminal hydrophobic signal sequence that targets the polypeptides for secretion. An RGD sequence, an element involved in cell-matrix interactions via integrin binding and signaling is also conserved in all sequences. Comparison of these sequences revealed 67% identity between the rat and mouse osteoregulins and 45% identity between human osteoregulin and either rat or mouse osteogulin. As shown in FIG. 5, the identity between the sequences was distributed throughout the entire length of the sequences. Preferred variants, homologues, fragments, or derivatives of the above disclosed osteoregulin sequences have a conserved RGD sequence (FIG. 5, underlined).

These osteoregulins share structural features common to a class of extracellular matrix phosphoglycoproteins that includes osteopontin, dentin, sialophosphoprotein, dentin matrix protein 1, and bone sialoprotein II. All of the above-mentioned related phosphoglycoproteins are expressed in bone or dentin and play roles in regulating mineralization (D'Souza et al., J. Bone Min. Res. 12: 2040–49, 1997; Robey, Conn. Tiss. Res. 35: 131–36, 1996; and Boskey, Conn. Tiss. Res. 35: 357–63, 1996).

The invention is also directed to nucleic acid sequences encoding an osteoregulin polypeptide or encoding any variant, homologue, derivative, or fragment thereof. Examples include the coding sequences and the full length cDNA-derived sequences for rat osteoregulin (FIG. 1A and SEQ ID NO: 1), mouse osteoregulin (FIG. 2A, and SEQ ID NO: 3), and two splice variants for human osteoregulins (FIG. 3A and SEQ ID NO: 5; FIG. 4A and SEQ ID NO: 7). Also encompassed by the invention are polynucleotide sequences that are capable of hybridizing to the polynucleotide sequences of the invention under various conditions of moderate and high stringency (see e.g., Wahl and Berger, Methods Enzymol. 152: 399–407, 1987, and Kimmel, Methods Enzymol. 152: 507–11, 1987).

The nucleic acid sequences encoding osteoregulin may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G., PCR Methods Applic. 2: 318–322, 1993.) Another method, inverse PCR, uses primers that extend in divergent directions to amplify unknown sequence from a circularized template. The template is derived from restriction fragments comprising a known genomic locus and surrounding sequences (see, e.g., Triglia et al., Nucleic Acids Res. 16: 8186, 1988). A third method, capture PCR, involves PCR amplification of DNA fragments adjacent to known sequences in human and yeast artificial chromosome DNA (see, e.g., Lagerstrom et al., PCR Methods Applic. 1: 111–119, 1991). In this method, multiple restriction enzyme digestions and ligations may be used to insert an engineered double-stranded sequence into a region of unknown sequence before performing PCR.

In another embodiment of the invention, a polynucleotide of the invention may be cloned in recombinant DNA molecules that direct expression of osteoregulin, its homologues, variants, derivatives, or fragments thereof, in appropriate host cells. The nucleotide sequences of the present invention can be engineered using methods generally known in the art in order to alter osteoregulin-encoding sequences for a variety of purposes including, but not limited to, modification of the cloning, processing, and/or expression of the gene product.

DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth. In another embodiment, sequences encoding osteoregulin may be synthesized, in whole or in part, using chemical methods well known in the art (see, e.g., Caruthers et al., Nucleic Acids Symp. Ser. 7: 215–223, 1980; and Horn et al., Nucleic Acids Symp. Ser. 7: 225–232, 1980). Alternatively, osteoregulin itself or a fragment thereof may be synthesized using chemical methods. For example, peptide synthesis can be performed using various solid- phase techniques (see, e.g., Roberge et al., Science 269: 202–204, 1995). Automated synthesis may be achieved using the ABI 431A peptide synthesizer (Perkin-Elmer, Norwalk, Conn.). Additionally, the amino acid sequence of osteoregulin, or any part thereof, may be altered during direct synthesis and/or combined with sequences from other proteins, or any part thereof, to produce a variant polypeptide. The peptide may be substantially purified by preparative high performance liquid chromatography (see, e.g., Chiez and Regnier, Methods Enzymol. 182: 392–421, 1990). The composition of the synthetic peptides may be confirmed by amino acid analysis or by sequencing (see, e.g., Creighton, Proteins, Structures and Molecular Properties, W H Freeman, New York, N.Y. 1984).

Osteoregulin-Encoding Expression Vectors

In order to express a biologically active osteoregulin, the nucleotide sequences encoding osteoregulin or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions derived from the vector and/or from the polynucleotide sequences encoding osteoregulin. Such elements may vary in their strength and specificity. Specific initiation signals may also be used to achieve more efficient translation of sequences encoding osteoregulin. Such signals include the ATG initiation codon and adjacent sequences, e.g. the Kozak sequence. In cases where sequences encoding osteoregulin and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used (see, e.g., Scharf et al., Results Probl. Cell Differ. 20:125–162, 1994). Methods which are well known to those skilled in the art may be used to construct expression vectors containing sequences encoding osteoregulin and appropriate transcriptional and translational control elements. These methods include in vitro recombinant DNA techniques, synthetic techniques, and in vivo genetic recombination. (See, e.g., Sambrook et al., *Molecular Cloning, Laboratory Manual*, Cold Spring Harbor Press, Plainview N.Y., ch. 4, 8, and 16–17, 1989; Ausubel et al., *Current Protocols in Molecular Biology*, John Wiley & Sons, New York, N.Y., chs. 9, 13, and 16, 1995). A variety of expression vector/host systems may be utilized to contain and express sequences encoding osteoregulin. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus), plant cell systems transformed with viral expression vectors (e.g., cauliflower mosaic virus, CaNW, or tobacco mosaic virus, TMV), with bacterial expression vectors (e.g., Ti or pBR322 plasmids), or animal cell systems. The invention is not limited by the host cell employed.

In bacterial systems, a number of cloning and expression vectors may be selected depending upon the use intended for polynucleotide sequences encoding osteoregulin. For example, routine cloning, subcloning, and propagation of polynucleotide sequences encoding osteoregulin can be achieved using a multifunctional *E.coli* vector such as pBlueScript (Stratagene, La Jolla, Calif.) or pSport1 plasmid (Life Technologies, Gaithersburg, Md.). Ligation of sequences encoding osteoregulin into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence (see, e.g., Van Heeke and Schuster, J. Biol. Chem. 264: 5503–5509, 1989). When large quantities of osteoregulin are needed, e.g. for the production of antibodies, vectors which direct high level expression of osteoregulin may be used. For example, vectors containing the strong, inducible T5 or T7 bacteriophage promoter may be used.

Host Cells Transformed with Osteorequlin-Encoding Sequences

Yeast expression systems maybe used for production of osteoregulin. A number of vectors containing constitutive or inducible promoters, such as alpha factor, alcohol oxidase, or PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation (see, e.g., Ausubel, 1995; Bitter et al., Methods Enzymol. 153: 516–544, 1987; and Scorer et al., BioTechnology 12: 181–184, 1994). Plant systems may also be used for expression of osteoregulin. Transcription of sequences encoding osteoregulin may be driven by viral promoters, e.g., the 35S and 19S promoters of CaMV used alone or in combination with the omega leader sequence from TMV (Takamatsu, EMBO J. 6: 307–311, 1987). Alternatively, plant promoters such as the small subunit of RUBISCO or heat shock promoters may be used. (see, e.g., Coruzzi et al., EMBO J. 3: 1671–1680, 1984; Broglie et al., Science 224: 838–843,1984; and Winter et al., Results Probl. Cell Differ. 17: 85–105, 1991). These constructs can be introduced into plant cells by direct DNA transformation or pathogen-mediated transfection (see, e.g., The McGraw Hill Yearbook of Science and Technology, McGraw Hill, New York N.Y., pp.191–196,1992).

In mammalian cells, a number of viral-based expression systems may be utilized. In cases where an adenovirus is used as an expression vector, sequences encoding osteoregulin may be ligated into an adenovirus transcription/translation complex consisting of the late promoter and tripartite leader sequence. Insertion in a non-essential E1 or E3 region of the viral genome may be used to obtain infective virus that express osteoregulin in infected host cells (see, e.g., Logan and Shenk, Proc. Natl. Acad. Sci. USA 81: 3655–3659, 1984). In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes (see, e.g., Harrington et al., Nat. Genet. 15: 345–355, 1997). For long term production of recombinant proteins in mammalian systems, stable expression of osteoregulin in cell lines is preferred. For example, sequences encoding osteoregulin can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻, and apr⁻ cells, respectively (see, e.g., Wigler et al., Cell 11: 223–232, 1997; Lowy et al., Cell 22: 817–823, 1980). Also, antimetabolite, antibiotic, or herbicide resistance can be used as the basis for selection. For example, dhft confers resistance to methotrexate; neo confers resistance to the aminoglycosides neomycin and G-418; and als and pat confer resistance to chlorsulfuron and phosphinotricin acetyltransferase, respectively (see, e.g., Wigler et al., Proc. Natl. Acad. Sci. USA 77: 3567–3570, 1980; Colbere-Garapin et al., J. Mol. Biol. 150: 1–14, 1981). Additional selectable genes have been described, e.g., trpB and hisD, which alter cellular requirements for metabolites (see, e.g., Hartman and Mulligan, Proc. Natl. Acad. Sci. USA 85: 8047–8051, 1988). Visible markers, e.g., anthocyanins, green fluorescent proteins (GFP; Clontech, Palo Alto, Calif.), β glucuronidase and its substrate β-glucuronide, or luciferase and its substrate luciferin may be used. These markers can be used not only to identify transformants, but also to quantify the amount of transient or stable protein expression attributable to a specific vector system (see, e.g., Rhodes, Methods Mol. Biol. 55: 121–131, 1995). Although the presence/absence of marker gene expression suggests that the gene of interest is also present, the presence and expression of the gene may need to be confirmed. For example, if the sequence encoding osteoregulin is inserted within a marker gene sequence, transformed cells containing sequences encoding osteoregulin can be identified by the absence of marker gene function. Alternatively, a marker gene can be placed in tandem with a sequence encoding osteoregulin under the control of a single promoter. Expression of the marker gene in response to induction or selection usually indicates expression of the tandem gene as well.

In general, host cells that contain the nucleic acid sequence encoding osteoregulin and that express osteoregulin may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of osteoregulin using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on osteoregulin is preferred, but a competitive binding assay may be employed. These and other assays are well known in the art (see, e.g., Hampton, *Serological Methods, A Laboratory Manual*, APS Press, St. Paul, Minn., Sect. IV, 1990; Coligan et al., *Current Protocols in Immunology*, Greene Pub. Associates and Wiley-Interscience, New York N.Y., 1997; and Pound, Immunochemical Protocols, Humana Press, Totowa, N.J., 1998). A wide variety of labels and conjugation techniques are known by those skilled in the art and may be used in various nucleic acid and amino acid assays.

Means for producing labeled hybridization or PCR probes for detecting sequences related to polynucleotides encoding osteoregulin include oligolabeling, nick translation, end-labeling, or PCR amplification using a labeled nucleotide. Alternatively, the sequences encoding osteoregulin, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (e.g., Amersham Pharmacia Biotech, Piscataway, N.J., Promega, Madison, Wis., and US Biochemical, Cleveland Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding osteoregulin may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode osteoregulin may be designed to contain signal sequences which direct secretion of osteoregulin through a prokaryotic or eukaryotic cell membrane. In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity.

Different host cells which have specific cellular machinery and characteristic mechanisms for post-translational activities (e.g., CHO, HeLa, MDCK, HEK293, and W138) are available from the American Type Culture Collection (ATCC, Manassas, Va.) and may be chosen to ensure the correct modification and processing of the foreign protein. In another embodiment of the invention, natural, modified, or recombinant nucleic acid sequences encoding osteoregulin may be ligated to a heterologous sequence resulting in translation of a fusion protein in any of the aforementioned host systems. For example, a chimeric osteoregulin protein containing a heterologous moiety that can be recognized by a commercially available antibody may facilitate the screening of peptide libraries for inhibitors of osteoregulin activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the osteoregulin encoding sequence and the heterologous protein sequence, so that osteoregulin may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled osteoregulin may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

Fragments of osteoregulin may be produced not only by recombinant means, but also by direct peptide synthesis using solid-phase techniques (see, e.g., Creighton, supra, pp. 55–60). Protein synthesis may be performed by manual techniques or by automation. Automated synthesis may be achieved, for example, using the ABI® 431A peptide synthesizer (Perkin-Elmer). Various fragments of osteoregulin may be synthesized separately and then combined to produce the full length molecule.

Genetically-Modified Non-human Mammals and Animal Cells Containing a Disrupted Osteoregulin Gene 1. Genetically-Modified Non-human Mammals and Animal Cells The genetically-modified, non-human mammals and genetically-modified animal cells, including human cells, of the invention are heterozygous or homozygous for a modification that functionally disrupts the osteoregulin gene. The animal cells may be derived by genetically engineering cells in culture, or, in the case of non-human mammalian cells, the cells may be isolated from genetically-modified, non-human mammals.

The osteoregulin gene locus is functionally disrupted by one of the several techniques for genetic modification known in the art, including chemical mutagenesis (Rinchik, Trends in Genetics 7: 15–21, 1991, Russell, Environmental & Molecular Mutagenesis 23 (Suppl. 24) 23–29, 1994), irradiation (Russell, supra), transgenic expression of osteoregulin gene antisense RNA, either alone or in combination with a catalytic RNA ribozyme sequence (Luyckx et al., Proc. Natl. Acad. Sci. 96: 12174–79, 1999; Sokol et al., Transgenic Research 5: 363–71, 1996; Efrat et al., Proc. Natl. Acad. Sci. USA 91: 2051–55, 1994; Larsson et al., Nucleic Acids Research 22: 2242–48, 1994) and, as further discussed below, the disruption of the osteoregulin gene by the insertion of a foreign nucleic acid sequence into the osteoregulin gene locus. Preferably, the foreign sequence is inserted by homologous recombinaton or by the insertion of a viral vector. Most preferably, the method of osteoregulin gene disruption is homologous recombination and includes a deletion of a portion of the endogenous osteoregulin gene sequence.

The integration of the foreign sequence functionally disrupts the osteoregulin gene through one or more of the following mechanisms: by interfering with the osteoregulin gene transcription or translation process (e.g., by interfering with promoter recognition, or by introducing a transcription termination site or a translational stop codon into the osteoregulin gene); or by distorting the osteoregulin gene coding sequence such that it no longer encodes a osteoregulin polypeptide with normal function (e.g., by inserting a foreign coding sequence into the osteoregulin gene coding sequence, by introducing a frameshift mutation or amino acid(s) substitution, or, in the case of a double crossover event, by deleting a portion of the osteoregulin gene coding sequence that is required for expression of a functional Y protein).

To insert a foreign sequence into a osteoregulin gene locus in the genome of a cell, the foreign DNA sequence is introduced into the cell according to a standard method known in the art such as electroporation, calcium-phosphate precipitation, retroviral infection, microinjection, biolistics, liposome transfection, DEAE-dextran transfection, or transferrinfection (see, e.g., Neumann et al., EMBO J. 1: 841–845, 1982; Potter et al., Proc. Natl. Acad. Sci USA 81: 7161–65, 1984; Chu et al., Nucleic Acids Res. 15:1311–26, 1987; Thomas and Capecchi, Cell 51: 503–12, 1987; Baum et al., Biotechniques 17: 1058–62, 1994; Biewenga et al., J. Neuroscience Methods 71: 67–75, 1997; Zhang et al., Biotechniques 15: 868–72, 1993; Ray and Gage, Biotechniques 13: 598–603, 1992; Lo, Mol. Cell. Biol. 3:1803–14, 1983; Nickoloff et al., Mol. Biotech. 10: 93–101, 1998; Linney et al., Dev. Biol. (Orlando) 213: 207–16, 1999; Zimmer and Gruss, Nature 338: 150–153, 1989; and Robertson et al., Nature 323: 445–48, 1986). The preferred method for introducing foreign DNA into a cell is electroporation.

2. Homologous Recombination

The method of homologous recombination targets the osteoregulin gene for disruption by introducing a osteoregulin gene targeting vector into a cell containing a osteoregulin gene. The ability of the vector to target the osteoregulin gene for disruption stems from using a nucleotide sequence in the vector that is homologous to the osteoregulin gene. This homology region facilitates hybridization between the vector and the endogenous sequence of the osteoregulin gene. Upon hybridization, the probability of a crossover event between the targeting vector and genomic sequences greatly increases. This crossover event results in the integration of the vector sequence into the osteoregulin gene locus and the functional disruption of the osteoregulin gene.

General principles regarding the construction of vectors used for targeting are reviewed in Bradley et al. (Biotechnol. 10: 534, 1992). Two different types of vector can be used to insert DNA by homologous recombination: an insertion vector or a replacement vector. An insertion vector is circular DNA which contains a region of osteoregulin gene homology with a double stranded break. Following hybridization between the homology region and the endogenous osteoregulin gene, a single crossover event at the double stranded break results in the insertion of the entire vector sequence into the endogenous gene at the site of crossover.

The more preferred vector to use for homologous recombination is a replacement vector, which is colinear rather than circular. Replacement vector integration into the osteoregulin gene requires a double crossover event, i.e. crossing over at two sites of hybridization between the targeting vector and the osteoregulin gene. This double crossover event results in the integration of vector sequence that is sandwiched between the two sites of crossover into the osteoregulin gene and the deletion of the corresponding endogenous osteoregulin gene sequence that originally spanned between the two sites of crossover (see, e.g., Thomas and Capecchi et al., Cell 51: 503–12, 1987; Mansour et al., Nature 336: 348–52, 1988; Mansour et al., Proc. Natl. Acad. Sci. USA 87: 7688–7692, 1990; and Mansour, GATA 7: 219–227, 1990).

A region of homology in a targeting vector is generally at least 100 nucleotides in length. Most preferably, the homology region is at least 1–5 kilobases (kb) in length. Although there is no demonstrated minimum length or minimum degree of relatedness required for a homology region, targeting efficiency for homologous recombination generally corresponds with the length and the degree of relatedness between the targeting vector and the osteoregulin gene locus. In the case where a replacement vector is used, and a portion of the endogenous osteoregulin gene is deleted upon homologous recombination, an additional consideration is the size of the deleted portion of the endogenous osteoregulin gene. If this portion of the endogenous osteoregulin gene is greater than 1 kb in length, then a targeting cassette with regions of homology that are longer than 1 kb is recommended to enhance the efficiency of recombination. Further guidance regarding the selection and use of sequences effective for homologous recombination is described in the literature (see, e.g., Deng and Capecchi, Mol. Cell. Biol. 12: 3365–3371, 1992; Bollag et al., Annu. Rev. Genet. 23: 199–225, 1989; and Waldman and Liskay, Mol. Cell. Biol. 8: 5350–5357, 1988).

A wide variety of cloning vectors may be used as vector backbones in the construction of the osteoregulin gene targeting vectors of the present invention, including pBluescript-related plasmids (e.g., Bluescript KS+11), pQE70, pQE60, pQE-9, pBS, pD10, phagescript, phiX174, pBK Phagemid, pNH8A, pNH16a, pNH18Z, pNH46A, ptrc99a, pKK223-3, pKK233-3, pDR540, and pRIT5 PWLNEO, pSV2CAT, pXT1, pSG (Stratagene), pSVK3, PBPV, PMSG, and pSVL, pBR322 and pBR322-based vectors, pBM9, pBR325, pKH47, pBR328, pHC79, phage Charon 28, pKB11, pKSV-10, pK19 related plasmids, pUC plasmids, and the pGEM series of plasmids. These vectors are available from a variety of commercial sources (e.g., Boehringer Mannheim Biochemicals, Indianapolis, Ind.; Qiagen, Valencia, Calif.; Stratagene, La Jolla, Calif.; Promega, Madison, Wis.; and New England Biolabs, Beverly, Mass.). However, any other vectors, e.g. plasmids, viruses, or parts thereof, may be used as long as they are replicable and viable in the desired host. The vector may also comprise sequences which enable it to replicate in the host whose genome is to be modified. The use of such a vector can expand the interaction period during which recombination can occur, increasing the efficiency of targeting (see Molecular Biology, ed. Ausubel et al, Unit 9.16, FIG. 9.16.1).

The specific host employed for propagating the targeting vectors of the present invention is not critical. Examples include *E. coli* K12 RR1 (Bolivar et al., Gene 2: 95, 1977), *E. coli* K12 HB101 (ATCC No. 33694), *E. coli* MM21 (ATCC No. 336780), *E. coli* DH1 (ATCC No. 33849), *E. coli* strain DH5α, and *E. coli* STBL2. Alternatively, hosts such as *C. cerevisiae* or *B. subtilis* can be used. The above-mentioned hosts are available commercially (e.g., Stratagene, La Jolla, Calif.; and Life Technologies, Rockville, Md.).

To create the targeting vector, a osteoregulin gene targeting construct is added to an above-described vector backbone. The osteoregulin gene targeting constructs of the invention have at least one osteoregulin gene homology region. To make the osteoregulin gene homology regions, a osteoregulin genomic or cDNA sequence is used as a basis for producing polymerase chain reaction (PCR) primers. These primers are used to amplify the desired region of the osteoregulin sequence by high fidelity PCR amplification (Mattila et al., Nucleic Acids Res. 19: 4967, 1991; Eckert and Kunkel 1: 17, 1991; and U.S. Pat. No. 4,683, 202). The genomic sequence is obtained from a genomic clone library or from a preparation of genomic DNA, preferably from the animal species that is to be targeted for osteoregulin gene disruption.

Preferably, the targeting constructs of the invention also include an exogenous nucleotide sequence encoding a positive marker protein. The stable expression of a positive marker after vector integration confers an identifiable characteristic on the cell without compromising cell viability. Therefore, in the case of a replacement vector, the marker gene is positioned between two flanking homology regions so that it integrates into the osteoregulin gene following the double crossover event.

It is preferred that the positive marker protein is a selectable protein; the stable expression of such a protein in a cell confers a selectable phenotypic characteristic, i.e., the characteristic enhances the survival of the cell under otherwise lethal conditions. Thus, by imposing the selectable condition, one can isolate cells that stably express the positive selectable marker-encoding vector sequence from other cells that have not successfully integrated the vector sequence on the basis of viability. Examples of positive selectable marker proteins (and their agents of selection) include neo (G418 or kanomycin), hyg (hygromycin), hisD (histidinol), gpt (xanthine), ble (bleomycin), and hprt (hypoxanthine) (see, e.g., Capecchi and Thomas, U.S. Pat. No. 5,464,764, and Capecchi, Science 244: 1288–92, 1989). Other positive markers that may also be used as an alternative to a selectable marker include reporter proteins such as β-galactosidase, firefly luciferase, or GFP (see, e.g., *Current Protocols in Cytometry*, Unit 9.5, and *Current Protocols in Molecular Biology*, Unit 9.6, John Wiley & Sons, New York, N.Y., 2000).

The above-described positive selection step does not distinguish between cells that have integrated the vector by targeted homologous recombination at the osteoregulin gene locus versus random, non-homologous integration of vector sequence into any chromosomal position. Therefore, when using a replacement vector for homologous recombination, it is also preferred to include a nucleotide sequence encoding a negative selectable marker protein. Expression of a negative selectable marker causes a cell expressing the marker to lose viability when exposed to a certain agent (i.e., the marker protein becomes lethal to the cell under certain selectable conditions). Examples of negative selectable markers (and their agents of lethality) include herpes simplex virus thymidine kinase (gancyclovir or 1,2-deoxy-2-fluoro-α-d-arabinofuransyl-5-iodouracil), Hprt (6-thioguanine or 6-thioxanthine), and diphtheria toxin, ricin toxin, and cytosine deaminase (5-fluorocytosine).

The nucleotide sequence encoding the negative selectable marker is positioned outside of the two homology regions of the replacement vector. Given this positioning, cells will only integrate and stably express the negative selectable marker if integration occurs by random, non-homologous recombination; homologous recombination between the osteoregulin gene and the two regions of homology in the targeting construct excludes the sequence encoding the negative selectable marker from integration. Thus, by imposing the negative condition, cells that have integrated the targeting vector by random, non-homologous recombination lose viability.

The above-described combination of positive and negative selectable markers is preferred because a series of positive and negative selection steps can be designed to more efficiently select only those cells that have undergone vector integration by homologous recombination, and, therefore, have a potentially disrupted osteoregulin gene. Further examples of positive-negative selection schemes, selectable markers, and targeting constructs are described, for example, in U.S. Pat. No. 5,464,764, WO 94/06908, and Valancius and Smithies, Mol. Cell. Biol. 11: 1402, 1991.

In order for a marker protein to be stably expressed upon vector integration, the targeting vector may be designed so that the marker coding sequence is operably linked to the endogenous osteoregulin gene promoter upon vector integration. Expression of the marker is then driven by the osteoregulin gene promoter in cells that normally express osteoregulin gene. Alternatively, each marker in the targeting construct of the vector may contain its own promoter that drives expression independent of the osteoregulin gene promoter. This latter scheme has the advantage of allowing for expression of markers in cells that do not typically express the osteoregulin gene (Smith and Berg, Cold Spring Harbor Symp. Quant. Biol. 49: 171, 1984; Sedivy and Sharp, Proc. Natl. Acad. Sci. (USA) 86: 227, 1989; Thomas and Capecchi, Cell 51: 503, 1987).

Exogenous promoters that can be used to drive marker gene expression include cell-specific or stage-specific promoters, constitutive promoters, and inducible or regulatable promoters. Non-limiting examples of these promoters include the herpes simplex thymidine kinase promoter, cytomegalovirus (CMV) promoter/enhancer, SV40 promoters, PGK prormoter, PMC1-neo, metallothionein promoter, adenovirus late promoter, vaccinia virus 7.5K promoter, avian beta globin promoter, histone promoters (e.g., mouse histone H3-614), beta actin promoter, neuron-specific enolase, muscle actin promoter, and the cauliflower mosaic virus 35S promoter (see generally, Sambrook et al., *Molecular Cloning*, Vols. I–III, Cold Spring Harbor Laboratory Press, Cold Spring Harbor, N.Y., 1989, and *Current Protocols in Molecular Biology*, John Wiley & Sons, New York, N.Y., 2000; Stratagene, La Jolla, Calif.).

To confirm whether cells have integrated the vector sequence into the targeted osteoregulin gene locus, primers or genomic probes that are specific for the desired vector integration event can be used in combination with PCR or Southern blot analysis to identify the presence of the desired vector integration into the osteoregulin gene locus (Erlich et al., Science 252: 1643–51, 1991; Zimmer and Gruss, Nature 338: 150, 1989; Mouellic et al., Proc. Natl. Acad. Sci. (USA) 87: 4712, 1990; and Shesely et al., Proc. Natl. Acad. Sci. (USA) 88: 4294, 1991).

3. Gene Trapping

Another method available for inserting a foreign nucleic acid sequence into the osteoregulin gene locus to functionally disrupt the osteoregulin gene is gene trapping. This method takes advantage of the cellular machinery present in all mammalian cells that splices exons into mRNA to insert a gene trap vector coding sequence into a gene in a random fashion. Once inserted, the gene trap vector creates a mutation that may functionally disrupt the trapped osteoregulin gene. In contrast to homologous recombination, this system for mutagenesis creates largely random mutations. Thus, to obtain a genetically-modified cell that contains a functionally disrupted osteoregulin gene, cells containing this particular mutation must be identified and selected from a pool of cells that contain random mutations in a variety of genes.

Gene trapping systems and vectors have been described for use in genetically modifying murine cells and other cell types (see, e.g., Allen et al., Nature 333: 852–55, 1988; Bellen et al., Genes Dev. 3: 1288–1300, 1989; Bier et al., Genes Dev. 3: 1273–1287, 1989; Bonnerot et al., J. Virol. 66: 4982–91, 1992; Brenner et al., Proc. Nat. Acad. Sci. USA 86: 5517–21, 1989; Chang et al., Virology 193: 737–47, 1993; Friedrich and Soriano, Methods Enzymol. 225: 681–701, 1993; Friedrich and Soriano, Genes Dev. 5: 1513–23, 1991; Goff, Methods Enzymol. 152: 469–81, 1987; Gossler et al., Science 244: 463–45, 1989; Hope, Develop. 113: 399–408, 1991; Kerr et al., Cold Spring Harb. Symp. Quant. Biol. 2: 767–776, 1989; Reddy et al., J. Virol. 65: 1507–1515, 1991; Reddy et al., Proc. Natl. Acad. Sci. U.S.A. 89: 6721–25, 1992; Skarnes et al., Genes Dev. 6: 903–918, 1992; von Melchner and Ruley, J. Virol. 63: 3227–3233, 1989; and Yoshida et al., Transgen. Res. 4: 277–87,1995).

Promoter trap, or 5', vectors contain, in 5' to 3' order, a splice acceptor sequence followed by an exon, which is typically characterized by a translation initiation codon and open reading frame and/or an internal ribosome entry site. In general, these promoter trap vectors do not contain promoters or operably linked splice donor sequences. Consequently, after integration into the cellular genome of the host cell, the promoter trap vector sequence intercepts the normal splicing of the upstream gene and acts as a terminal exon. Expression of the vector coding sequence is dependent upon the vector integrating into an intron of the disrupted gene in the proper reading frame. In such a case, the cellular splicing machinery splices exons from the trapped gene upstream of the vector coding sequence (Zambrowicz et al., WO 99/50426).

An alternative method for producing an effect similar to the above-described promoter trap vector is a vector that incorporates a nested set of stop codons present in, or otherwise engineered into, the region between the splice acceptor of the promoter trap vector and the translation initiation codon or polyadenylation sequence. The coding sequence can also be engineered to contain an independent ribosome entry site (IRES) so that the coding sequence will be expressed in a manner largely independent of the site of integration within the host cell genome. Typically, but not necessarily, an IRES is used in conjunction with a nested set of stop codons.

Another type of gene trapping scheme uses a 3' gene trap vector. This type of vector contains, in operative combination, a promoter region, which mediates expression of an adjoining coding sequence, the coding sequence, and a splice donor sequence that defines the 3' end of the coding sequence exon. After integration into a host cell genome, the transcript expressed by the vector promoter is spliced to a splice acceptor sequence from the trapped gene that is located downstream of the integrated gene trap vector sequence. Thus, the integration of the vector results in the expression of a fusion transcript comprising the coding sequence of the 3' gene trap cassette and any downstream cellular exons, including the terminal exon and its polyadenylation signal. When such vectors integrate into a gene, the cellular splicing machinery splices the vector coding sequence upstream of the 3' exons of the trapped gene. One advantage of such vectors is that the expression of the 3' gene trap vectors is driven by a promoter within the gene trap cassette and does not require integration into a gene that is normally expressed in the host cell (Zambrowicz et al., WO 99/50426). Examples of transcriptional promoters and enhancers that may be incorporated into the 3' gene trap vector include those discussed above with respect to targeting vectors.

The viral vector backbone used as the structural component for the promoter or 3' gene trap vector may be selected from a wide range of vectors that can be inserted into the genome of a target cell. Suitable backbone vectors include, but are not limited to, herpes simplex virus vectors, adenovirus vectors, adeno-associated virus vectors, retroviral vectors, lentiviral vectors, pseudorabies virus, alpha-herpes virus vectors, and the like. A thorough review of viral vectors, in particular, viral vectors suitable for modifying nonreplicating cells and how to use such vectors in conjunction with the expression of an exogenous polynucleotide sequence, can be found in *Viral Vectors: Gene Therapy and Neuroscience Applications*, Eds. Caplitt and Loewy, Academic Press, San Diego, 1995.

Preferably, retroviral vectors are used for gene trapping. These vectors can be used in conjunction with retroviral packaging cell lines such as those described in U.S. Pat. No. 5,449,614. Where non-murine mammalian cells are used as target cells for genetic modification, amphotropic or pantropic packaging cell lines can be used to package suitable vectors (Ory et al., Proc. Natl. Acad. Sci., USA 93: 11400–11406, 1996). Representative retroviral vectors that can be adapted to create the presently described 3' gene trap vectors are described, for example, in U.S. Pat. No. 5,521,076.

The gene trapping vectors may contain one or more of the positive marker genes discussed above with respect to targeting vectors used for homologous recombination. Similar to their use in targeting vectors, these positive markers are used in gene trapping vectors to identify and select cells that have integrated the vector into the cell genome. The marker gene may be engineered to contain an independent ribosome entry site (IRES) so that the marker will be expressed in a manner largely independent of the location in which the vector has integrated into the target cell genome.

Given that gene trap vectors will integrate into the genome of infected host cells in a fairly random manner, a genetically-modified cell having a disrupted osteoregulin gene must be identified from a population of cells that have undergone random vector integration. Preferably, the genetic modifications in the population of cells are of sufficient randomness and frequency such that the population represents mutations in essentially every gene found in the cell's genome, making it likely that a cell with a disrupted osteoregulin gene will be identified from the population (see Zambrowicz et al., WO 99/50426; Sands et al., WO 98/14614).

Individual mutant cell lines containing a disrupted osteoregulin gene are identified in a population of mutated cells using, for example, reverse transcription and polymerase chain reaction (PCR) to identify a mutation in a osteoregulin gene sequence. This process can be streamlined by pooling clones. For example, to find an individual clone containing a disrupted osteoregulin gene, RT-PCR is performed using one primer anchored in the gene trap vector and the other primer located in the osteoregulin gene sequence. A positive RT-PCR result indicates that the vector sequence is encoded in the osteoregulin gene transcript, indicating that osteoregulin gene has been disrupted by a gene trap integration event (see, e.g., Sands et al., WO 98/14614).

4. Temporal, Spatial, and Inducible Osteoregulin Gene Disruptions

In certain embodiments of the present invention, a functional disruption of the endogenous osteoregulin gene occurs at specific developmental or cell cycle stages (temporal disruption) or in specific cell types (spatial disruption). In other embodiments, the osteoregulin gene disruption is inducible when certain conditions are present. A recombinase excision system, such as a Cre-Lox system, may be used to activate or inactivate the osteoregulin gene at a specific developmental stage, in a particular tissue or cell type, or under particular environmental conditions. Generally, methods utilizing Cre-Lox technology are carried out as described by Torres and Kuhn, *Laboratory Protocols for Conditional Gene Targeting*, Oxford University Press, 1997. Methodology similar to that described for the Cre-Lox system can also be employed utilizing the FLP-FRT system. Further guidance regarding the use of recombinase excision systems for conditionally disrupting genes by homologous recombination or viral insertion is provided, for example, in U.S. Pat. No. 5,626,159, U.S. Pat. No. 5,527,695, U.S. Pat. No. 5,434,066, WO 98/29533, Orban et al., Proc. Nat. Acad. Sci. USA 89: 6861–65, 1992; O'Gorman et al., Science 251: 1351–55, 1991; Sauer et al., Nucleic Acids Research 17: 147–61, 1989; Barinaga, Science 265: 26–28, 1994; and Akagi et al., Nucleic Acids Res. 25: 1766–73, 1997. More than one recombinase system can be used to genetically modify a non-human mammal or animal cell.

When using homologous recombination to disrupt the osteoregulin gene in a temporal, spatial, or inducible fashion, using a recombinase system such as the Cre-Lox system, a portion of the osteoregulin gene coding region is replaced by a targeting construct comprising the osteoregulin gene coding region flanked by loxP sites. Non-human mammals and animal cells carrying this genetic modification contain a functional, loxP-flanked osteoregulin gene. The temporal, spatial, or inducible aspect of the osteoregulin gene disruption is caused by the expression pattern of an additional transgene, a Cre recombinase transgene, that is expressed in the non-human mammal or animal cell under the control of the desired spatially-regulated, temporally-regulated, or inducible promoter, respectively. A Cre recombinase targets the loxP sites for recombination. Therefore, when Cre expression is activated, the LoxP sites undergo recombination to excise the sandwiched osteoregulin gene coding sequence, resulting in a functional disruption of the osteoregulin gene (Rajewski et al., J. Clin. Invest. 98: 600–03, 1996; St.-Onge et al., Nucleic Acids Res. 24: 3875–77, 1996; Agah et al., J. Clin. Invest. 100: 169–79, 1997; Brocard et al., Proc. Natl. Acad. Sci. USA 94: 14559–63, 1997; Feil et al., Proc. Natl. Acad. Sci. USA 93: 10887–90, 1996; and Kühn et al., Science 269: 1427–29, 1995).

A cell containing both a Cre recombinase transgene and loxP-flanked osteoregulin gene can be generated through standard transgenic techniques or, in the case of genetically-modified, non-human mammals, by crossing genetically-modified, non-human mammals wherein one parent contains a loxP flanked osteoregulin gene and the other contains a Cre recombinase transgene under the control of the desired promoter. Further guidance regarding the use of recombinase systems and specific promoters to temporally, spatially, or conditionally disrupt the osteoregulin gene is found, for example, in Sauer, Meth. Enz. 225: 890–900, 1993, Gu et al., Science 265: 103–06, 1994, Araki et al., J. Biochem. 122: 977–82, 1997, Dymecki, Proc. Natl. Acad. Sci. 93: 6191–96, 1996, and Meyers et al., Nature Genetics 18: 136–41, 1998.

An inducible disruption of the osteoregulin gene can also be achieved by using a tetracycline responsive binary system (Gossen and Bujard, Proc. Natl. Acad. Sci. USA 89: 5547–51, 1992). This system involves genetically modifying a cell to introduce a Tet promoter into the endogenous osteoregulin gene regulatory element and a transgene expressing a tetracycline-controllable repressor (TetR). In such a cell, the administration of tetracycline activates the TetR which, in turn, inhibits osteoregulin gene expression and, therefore, functionally disrupts the osteoregulin gene (St,-Onge et al., Nucleic Acids Res. 24: 3875–77, 1996, U.S. Patent No. 5,922,927).

The above-described systems for temporal, spatial, and inducible disruptions of the osteoregulin gene can also be adopted when using gene trapping as the method of genetic modification, for example, as described, in WO 98/29533.

5. Creating Genetically-Modified, Non-human Mammals and Animal Cells

The above-described methods for genetic modification can be used to functionally disrupt a osteoregulin gene in virtually any type of somatic or stem cell derived from an animal. Genetically-modified animal cells of the invention include, but are not limited to, mammalian cells, including human cells, and avian cells. These cells may be derived from genetically engineering any animal cell line, such as culture-adapted, tumorigenic, or transformed cell lines, or they may be isolated from a genetically-modified, non-human mammal carrying the desired osteoregulin genetic modification.

The cells may be heterozygous or homozygous for the disrupted osteoregulin gene. To obtain cells that are homozygous for the osteoregulin gene disruption (osteoregulin−/−), direct, sequential targeting of both alleles can be performed. This process can be facilitated by recycling a positive selectable marker. According to this scheme the nucleotide sequence encoding the positive selectable marker is removed following the disruption of one allele using the Cre-Lox P system. Thus, the same vector can be used in a subsequent round of targeting to disrupt the second osteoregulin gene allele (Abuin and Bradley, Mol. Cell. Biol. 16: 1851–56, 1996; Sedivy et al., T.I.G. 15: 88–90, 1999; Cruz et al., Proc. Natl. Acad. Sci. (USA) 88: 7170–74, 1991; Mortensen et al., Proc. Natl. Acad. Sci. (USA) 88: 7036–40, 1991; te Riele et al., Nature (London) 348: 649–651, 1990).

An alternative strategy for obtaining ES cells that are osteoregulin−/− is the homogenotization of cells from a population of cells that is heterozygous for the osteoregulin gene disruption (osteoregulin+/−). The method uses a scheme in which osteoregulin+/− targeted clones that express a selectable drug resistance marker are selected against a very high drug concentration; this selection favors cells that express two copies of the sequence encoding the drug resistance marker and are, therefore, homozygous for the osteoregulin gene disruption (Mortensen et al., Mol. Cell. Biol. 12: 2391–95, 1992). In addition, genetically-modified animal cells can be obtained from genetically-modified osteoregulin−/− non-human mammals that are created by mating non-human mammals that are osteoregulin+/− in germine cells, as further discussed below.

Following the genetic modification of the desired cell or cell line, the osteoregulin gene locus can be confirmed as the site of modification by PCR analysis according to standard PCR or Southern blotting methods known in the art (see, e.g., U.S. Pat. No. 4,683,202; and Erlich et al., Science 252: 1643, 1991). Further verification of the functional disruption of the osteoregulin gene may also be made if osteoregulin gene messenger RNA (mRNA) levels and/or osteoregulin polypeptide levels are reduced in cells that normally express the osteoregulin gene. Measures of osteoregulin gene mRNA levels may be obtained by using reverse transcriptase mediated polymerase chain reaction (RT-PCR), Northern blot analysis, or in situ hybridization. The quantification of osteoregulin polypeptide levels produced by the cells can be made, for example, by standard immunoassay methods known in the art. Such immunoassays include, but are not limited to, competitive and non-competitive assay systems using techniques such as RIAs (radioimmunoassays), ELISAs (enzyme-linked immunosorbent assays), "sandwich" immunoassays, immunoradiometric assays, gel diffusion precipitin reactions, immunodiffusion assays, in situ immunoassays (using, for example, colloidal gold, enzymatic, or radioisotope labels), Western blots, 2-dimensional gel analysis, precipitation reactions, immunofluorescence assays, protein A assays, and immunoelectrophoresis assays.

Preferred genetically-modified animal cells are embryonic stem (ES) cells and ES-like cells. These cells are derived from the preimplantation embryos and blastocysts of various species, such as mice (Evans et al., Nature 129:154–156,1981; Martin, Proc. Natl. Acad. Sci., USA, 78: 7634–7638, 1981), pigs and sheep (Notanianni et al., J. Reprod. Fert. Suppl., 43: 255–260, 1991; Campbell et al., Nature 380: 64–68, 1996) and primates, including humans (Thomson et al., U.S. Patent No. 5,843,780, Thomson et al., Science 282:1145–1147, 1995; and Thomson et al., Proc. Natl. Acad. Sci. USA 92: 7844–7848, 1995).

These types of cells are pluripotent. That is, under proper conditions, they differentiate into a wide variety of cell types derived from all three embryonic germ layers: ectoderm, mesoderm and endoderm. Depending upon the culture conditions, a sample of ES cells can be cultured indefinitely as stem cells, allowed to differentiate into a wide variety of different cell types within a single sample, or directed to differentiate into a specific cell type, such as macrophage-like cells, neuronal cells, cardiomyocytes. chondrocytes, adipocytes, smooth muscle cells, endothelial cells, skeletal muscle cells, keratinocytes, and hematopoietic cells, such as eosinophils, mast cells, erythroid progenitor cells, or megakaryocytes. Directed differentiation is accomplished by including specific growth factors or matrix components in the culture conditions, as further described, for example, in Keller et al., Curr. Opin. Cell Biol. 7: 862–69, 1995, Li et al., Curr. Biol. 8: 971, 1998, Klug et al., J. Clin. Invest. 98: 216–24, 1996, Lieschke et al., Exp. Hematol. 23: 328–34, 1995, Yamane et al., Blood 90: 3516–23, 1997, and Hirashima et al., Blood 93: 1253–63, 1999.

The particular embryonic stem cell line that is used for genetic modification is not critical; exemplary murine ES cell lines include AB-1 (McMahon and Bradley, Cell 62: 1073–85, 1990), E14 (Hooper et al., Nature 326: 292–95, 1987), D3 (Doetschman et al., J. Embryol. Exp. Morph. 87: 27–45, 1985), CCE (Robertson et al, Nature 323: 445–48, 1986), RW4 (Genome Systems, St. Louis, Mo.), and DBA/1lacJ (Roach et al., Exp. Cell Res. 221: 520–25, 1995). Genetically-modified murine ES cells may be used to generate genetically-modified mice, according to published procedures (Robertson, 1987, *Teratocarcinomas and Embryonic Stem Cells: A Practical Approach*, Ed. E. J. Robertson, Oxford: IRL Press, pp. 71–112, 1987; Zjilstra et al., Nature 342: 435–438, 1989; and Schwartzberg et al., Science 246: 799–803, 1989).

Following confirmation that the ES cells contain the desired functional disruption of the osteoregulin gene, these ES cells are then injected into suitable blastocyst hosts for generation of chimeric mice according to methods known in the art (Capecchi, Trends Genet. 5: 70, 1989). The particular mouse blastocysts employed in the present invention are not critical. Examples of such blastocysts include those derived from C57BL6 mice, C57BL6 Albino mice, Swiss outbred mice, CFLP mice, and MFI mice. Alternatively ES cells may be sandwiched between tetraploid embryos in aggregation wells (Nagy et al., Proc. Natl. Acad. Sci. USA 90: 8424–8428, 1993).

The blastocysts or embryos containing the genetically-modified ES cells are then implanted in pseudopregnant female mice and allowed to develop in utero (Hogan et al., *Manipulating the Mouse Embryo: A Laboratory Manual*, Cold Spring Harbor Laboratory press, Cold Spring Harbor, N.Y. 1988; and *Teratocarcinomas and Embryonic Stem Cells: A Practical Approach*, E. J. Robertson, ed., IRL Press, Washington, D.C., 1987). The offspring born to the foster mothers may be screened to identify those that are chimeric for the osteoregulin gene disruption. Generally, such offspring contain some cells that are derived from the genetically-modified donor ES cell as well as other cells from the original blastocyst. In such circumstances, offspring may be screened initially for mosaic coat color, where a coat color selection strategy has been employed, to distinguish cells derived from the donor ES cell from the other cells of the blastocyst. Alternatively, DNA from tail tissue of the offspring can be used to identify mice containing the genetically-modified cells.

The mating of chimeric mice that contain the osteoregulin gene disruption in germ line cells produces progeny that possess the osteoregulin gene disruption in all germ line cells and somatic cells. Mice that are heterozygous for the osteoregulin gene disruption can then be crossed to produce homozygotes (see, e.g., U.S. Pat. Nos. 5,557,032, and 5,532,158).

An alternative to the above-described ES cell technology for transferring a genetic modification from a cell to a whole animal is to use nuclear transfer. This method can be employed to make other genetically-modified, non-human mammals besides mice, for example, sheep (McCreath et al., Nature 29: 1066–69, 2000; Campbell et al., Nature 389: 64–66, 1996; and Schnieke et al., Science 278: 2130–33, 1997) and calves (Cibelli et al., Science 280: 1256–58, 1998). Briefly, somatic cells (e.g., fibroblasts) or pluripotent stem cells (e.g., ES-like cells) are selected as nuclear donors and are genetically-modified to contain a functional disruption of the osteoregulin gene. When inserting a DNA vector into a somatic cell to mutate the osteoregulin gene, it is preferred that a promoterless marker be used in the vector such that vector integration into the osteoregulin gene results in expression of the marker under the control of the osteoregulin gene promoter (Sedivy and Dutriaux, T.I.G. 15: 88–90, 1999; Mccreath et al., Nature 29: 1066–49, 2000). Nuclei from donor cells which have the appropriate osteoregulin gene disruption are then transferred to fertilized or parthenogenetic oocytes that are enucleated (Campbell et al., Nature 380: 64, 1996; Wilmut et al., Nature 385: 810, 1997). Embryos are reconstructed, cultured to develop into the morula/blastocyst stage, and transferred into foster mothers for full term in utero development.

The present invention also encompasses the progeny of the genetically-modified, non-human mammals and genetically-modified animal cells. While the progeny are heterozygous or homozygous for the genetic modification that functionally disrupts the osteoregulin gene, they may not be genetically identical to the parent non-human mammals and animal cells due to mutations or environmental influences that may occur in succeeding generations at other loci besides that of the original genetic disruption of the osteoregulin gene.

6 "Humanized" Non-human Mammals and Animal Cells

The genetically-modified non-human mammals and animal cells (non-human) of the invention containing a disrupted endogenous osteoregulin gene can be further modified to express the human osteoregulin sequence (referred to herein as "humanized"). A preferred method for humanizing cells involves replacing the endogenous osteoregulin sequence with nucleic acid sequence encoding the human osteoregulin sequence by homologous recombination. The vectors are similar to those traditionally used as targeting vectors with respect to the 5' and 3' homology arms and positive/negative selection schemes. However, the vectors also include sequence that, after recombination, either substitutes the human osteoregulin coding sequence for the endogenous sequence, or effects base pair changes, exon substitutions, or codon substitutions that modify the endogenous sequence to encode the human osteoregulin. Once homologous recombinants have been identified, it is possible to excise any selection-based sequences (e.g., neo) by using Cre or Flp-mediated site directed recombination (Dymecki, Proc. Natl. Acad. Sci. 93: 6191–96,1996).

When substituting the human osteoregulin sequence for the endogenous sequence, it is preferred that these changes are introduced directly downstream of the endogenous translation start site. This positioning preserves the endogenous temporal and spatial expression patterns of the osteoregulin gene. The human sequence can be the full length human cDNA sequence with a polyA tail attached at the 3' end for proper processing or the whole genomic sequence (Shiao et al., Transgenic Res. 8: 295–302, 1999). Further guidance regarding these methods of genetically modifying cells and non-human mammals to replace expression of an endogenous gene with its human counterpart is found, for example, in Sullivan et al., J. Biol. Chem. 272: 17972–80, 1997, Reaume et al., J. Biol. Chem. 271: 2338–88, 1996, and Scott et al., U.S. Pat. No. 5,777,194).

Another method for creating such "humanized" organisms is a two step process involving the disruption of the endogenous gene followed by the introduction of a transgene encoding the human sequence by pronuclear microinjection into the knock-out embryos.

Screening Methods

The invention provides methods (also referred to herein as "screening assays") for identifying modulators that stimulate or inhibit osteoregulin activity. Such modulators include, e.g., test compounds, agents, proteins, peptides, peptidomimetics, peptoids, small molecules, and other chemical entities. Therefore, agents thus identified can be used to regulate bone growth/formation, bone density, bone mineralization, and/or adiposity in a therapeutic protocol. Such therapy may be useful, for example, to treat or prevent osteoporosis or to stimulate bone repair or regeneration.

The test compounds used for screening may be selected individually or obtained from a compound library. Such libraries include biological libraries, peptoid libraries (libraries of molecules having the functions of peptides, but with novel, non-peptide backbones which are resistant to enzymatic degradation yet remain bioactive) (see, e.g., Zuckermann, J. Med. Chem. 37:2678–85, 1994), spatially addressable parallel solid phase or solution phase libraries, synthetic library methods requiring deconvolution, the "one-bead onecompound" library method, and synthetic library methods using affinity chromatography selection.

Examples of methods for the synthesis of molecular libraries can be found in the art, for example, in: DeWitt et al., Proc. Natl. Acad. Sci. (USA) 90:6909 (1993); Erd et al., Proc. Natl. Acad. Sci. (USA) 91: 11422, 1994; Zuckermann et al., J. Med. Chem., 37:2678, 1994; Cho et al., Science, 261:1303, 1995; Carrell et al., Angew. Chem. Int. Ed. Engl. 33:2061, 1994; and in Gallop et al., J. Med. Chem. 37:1233, 1994.

Libraries of compounds may be presented in solution (e.g., Houghten, Biotechniques, 13:412–421, 1992), or on beads (Lam, Nature 354:82–841, 1991), on chips (Fodor, Nature 364:555–556, 1993), bacteria and spores (Ladner U.S. Pat. No. 5,223,409), plasmids (Cull et al., Proc. Natl. Acad. Sci. USA. 89:1865–1869, 1992) or on phage (Scott et al., Science 249:386–390, 1990; Devlin, Sdence 249:404–406, 1990; Cwirla et al., Proc. Natl. Acad. Sci. (USA) 87:6378–6382, 1990; Felici, J. Mol. Biol. 222:301–310, 1991; Ladner, supra).

In a preferred embodiment, the effect of an agent in modulating the cellular activity of an osteoregulin polypeptide is measured in a cell type that plays a role in mediating calcium homeostasis and/or bone density, for example, cells derived from kidney, intestine, parathyroid, C cells, thyroid, hypothalamus, and bone. Preferred cells are osteoblast cell lines (available from the American Type Culture Collection, Manassas, VA), such as SaOS, UMR, ros, MC3T3L1, U2OS, MG-63, HOS5, and primary osteoblast cultures derived from marrow or calvarial preparations. Femur and tibia bone marrow cells are harvested by centrifugation, and plated at a density of $15 \times 10^6$ cells per 100 mM diameter plate in alpha-minimal essential medium with 10% fetal bovine serum and 50 µg/ml gentamycin (Gibco BRL, Gaithersburg, Md.). Calvarial preparations are prepared as described, for example, in Owen et al., J. Cell. Physiol. 143: 420–30, 1990.

The effects of osteoregulin may be studied in cultured cells or in vivo. Osteoregulin protein, obtained from a natural source or from recombinant expression in a bacterial or mammalian host cell, can be applied to the cells, or administered to a mammal, in the presence or absence of the test agent. Alternatively, the osteoregulin protein could be administered to the test cells or mammals by genetic modification, such that an exogenous osteoregulin coding sequence is expressed in the cultured cells or mammals using methodology based, for example, on transgenics, naked DNA delivery, or viral vector insertion.

An agent is identified as an inhibitor or enhancer of osteoregulin activity, for example, if the agent reduces or increases, respectively, osteoregulin-mediated changes in bone structure or bone mineralization. Such changes may be assessed, for example, by Von Kossa staining (Von Kossa, Bietr. Anat 29: 163, 1901), by histomorphometry (e.g., Simmons et al., J. Pharmacol. & Exp. Therap. 286: 341–44, 1998), by measuring bone cell proliferation, and/or by a quantifying marker of osteoblast activation, such as alkaline phosphatase, osteocalcin, or osteopontin. Histomorphometric values can be analyzed using computer-aided image analysis (Bioquant II, M Biometrics, Nashville, Tenn.).

In another embodiment, the invention provides an assay for identifying an agent that modulates the expression of an osteoregulin protein. The method uses cells capable of expressing an osteoregulin gene (e.g., an osteoblast cell line). The amount of endogenous osteoregulin gene expression can be measured or the amount of transgene expression can be measured in a cell transformed with a transgene containing a regulatory element(s) of an osteoregulin gene (e.g. an osteoregulin promoter) operably linked to a nucleic acid sequence encoding a polypeptide (e.g., a reporter protein), such that the osteoregulin gene regulatory element controls expression of the coding sequence.

For example, a genomic DNA fragment spanning from 13 bp upstream of the osteoregulin ATG start site to approximately 400–10000 base pairs upstream of the start site is cloned into a vector (e.g., pGL3, Promega, Madison, Wis.) such that the osteoregulin regulatory elements included in the genomic fragment control expression of a reporter gene such as luciferase. This vector is then transfected into cells that normally express an osteoregulin gene. Agents that increase or decrease osteoregulin expression are identified by an increased or decreased level, respectively, of luciferase in these transfected cells. In preferred embodiments, the osteoregulin gene promoter is human or mouse.

EXAMPLES

Unless otherwise stated, methods for identifying and characterizing mouse and human osteoregulin were as described for identifying and characterizing rat osteoregulin.

Rat Osteoregulin

1. Osteoregulin Isolation

The rat osteoregulin gene was isolated from a pool of genes with induced expression during osteoblast differentiation. Primary rat bone marrow cells (RBMC) were isolated and differentiated into osteoblastic cells in the presence of 10 nM dexamethasone (Rickard et al., Developmental Biology 161: 218–28, 1994; Leboy et al., J. of Cellular Physiology 146: 370–8, 1991). Consistent with earlier literature reports (Maniatopoulos et al., Cell & Tissue Research 254: 317–30, 1988; Rickard et al., Developmental Biology 161: 218–28, 1994; Leboy et al., J. of Cellular Physiology 146: 370–8, 1991), this culture system required dexamethasone treatment to potentiate differentiation into osteoblastic cells as evidenced by induction of osteoblast marker genes (FIG. 6) or the ability to detect mineralization by Von Kossa staining when a phosphate source such as β-glycerophosphate was included in the culture medium.

Primary rat bone marrow cells (RBMC) were isolated and differentiated into osteoblastic cells as previously described (Rickard et al., Developmental Biology 161: 218–28, 1994; Leboy et al., J. of Cellular Physiology 146: 370–8, 1991). Marrow was isolated from the tibia and femur of 3 month old Sprague Dawley female rats and placed into culture medium Minimum Essential Medium (MEM) supplemented with 15% fetal calf serum, 2 mM glutamine, 0.1 mg/ml gentamicin, 100 U/ml penicillin and 100 µg/ml streptomycin; Gibco/BRL, Gaithersburg, Md.). Isolated marrow cells were filtered through 100 µm mesh, washed 3 times with culture medium and plated into 10 cm tissue culture dishes at a density of $1 \times 10^6$ cells/cm$^2$. Cells were allowed to attach for 4 days undisturbed at 37° C. with 5% $CO_2$. Cells were grown until 90% confluent at which time they were treated with 50 µg/ml ascorbate and 10 nM dexamethasone in culture medium. Medium was changed 3 times per week after the initial attachment period. To assess the ability of these cell cultures to mineralize, cultures were maintained in 50 µg/ml ascorbate/10 nM dexamethasone/10 mM β-glycerophosphate and stained by Von Kossa staining.

Von Kossa staining visualizes the mineralization of calveria and bone marrow cultures by silver nitrate staining. The media was removed from cells and the plate rinsed once with phosphate buffered saline (PBS). Cells were fixed with cold methanol (−20° C.) for 10 minutes. Plates were then stained with 5% $AgNO_3$ in direct sunlight for 5 minutes. Plates were then rinsed with water and examined for mineralization.

A cDNA library enriched for genes induced during osteoblastic differentiation was constructed by subtractive hybridization of cDNA from dexamethasone treated RBMC versus cDNA from vehicle treated cultures (Wang and Brown, Proceedings of the National Academy of Sciences of the United States of America 88: 11505–9, 1991; Rivera-Gonzalez et al., J. of Steroid Biochemistry & Molecular Biology 64: 13–24, 1998). Briefly, 5 µg of poly A+ mRNA from untreated cultures and 5 µg from dexamethasone treated cultures were used to generate cDNA using Superscript II reverse transcriptase following conditions specified by the manufacturer (Gibco BRL, Gaithersburg, Md.). The PCR product after 5 rounds of subtractive hybridization was ligated to BamHI digested/alkaline phosphatase treated pBSSK+ (Stratagene, La Jolla, Calif.). Colonies were screened by hybridization to round 5 probe as previously described (Rivera-Gonzalez et al., J. of Steroid Biochemistry & Molecular Biology 64: 13–24, 1998).

After 5 rounds of subtractive hybridization, clones were analyzed by colony screening using round 5 subtracted cDNA as a probe. This step constituted hybridization of the library against itself. Under these conditions, approximately 70% of the clones yielded a positive hybridization signal. These results suggest that non-hybridizing clones represented rare messages within the population that were not efficiently subtracted. Only hybridizing colonies were chosen for further analysis. A total of 153 of the hybridizing clones were randomly selected and sequenced. The insert size ranged from 150–450 bp. The sequence data were assembled and compared to known genes in GenBank with the BLAST algorithm (Altschul et al., J. of Molecular Biology 215: 403–10, 1990). Regulation was determined by Northern blot analysis of 20 µg total RNA from vehicle or dexamethasone treated RBMC cultures. A summary of the analysis of these 153 clones is shown in Table 1.

TABLE 1

Summary of identities, frequencies and regulation of clones isolated from dexamethasone treated subtractive library

| Fragment identity | Frequency | Regulation |
|---|---|---|
| Osteopontin | 32 | + |
| Osteoregulin | 26 | + |
| Bone sialoprotein | 12 | + |
| Cystatin | 7 | + |
| Mucofibrase | 3 | ND |
| Alpha 2-macroglobulin | 1 | ND |
| Procollagen | 1 | ND |
| Prostacylin synthase | 1 | ND |
| 28S RNA | 1 | NR |
| Osteocalcin | 1 | + |
| Clone 28 | 8 | NS |
| Clone 26 | 7 | NS |
| Clone 68 | 4 | ND |
| Clone 63 | 3 | ND |
| Clone 74 | 2 | NS |
| Clone 140 | 2 | NR |
| Clone 126 | 2 | NS |
| Clone 90 | 2 | ND |
| Single isolates | 38 | |

Results are indicated as follows: + = up regulated by DEX; NR = not regulated, NS = no signal detected; ND = not determined.

As an indicator of the efficiency of the subtraction, there was very little contamination with ribosomal RNA (1/153) or with mitochondrial genes (0/153). The identification of genes previously reported to be induced during osteoblast differentiation (Owen et al., J. of Cellular Physiology 143: 420–30, 1990) such as osteopontin, bone sialoprotein and osteocalcin, confirmed that the subtractive library contained osteoblast marker genes.

Plasmid DNA was isolated from hybridizing colonies and sequenced. Sequencing of purified DNA was performed on an ABI 373 automated sequencing apparatus with cycle sequencing using BigDye Terminator (BDT) Taq FS chemistry (PE Biosystems, Foster City, Calif.) according to the manufacturer's protocol with the following modifications: 1) half-reaction BDT reactions (50% BDT, 50% ABI 5×Buffer) contained 5% DMSO; 2) cycle sequencing thermal profile with hot start: 95° C. for 1 min for 1 cycle, 98° C. for 45 s, 50° C. for 10 s, 60° C. for 4 min for one cycle, followed by 98° C. for 15 s, 50° C. for 10 s, 60° C. for 4 m for a total of 30 cycles (MJ Tetrad Thermal Cycler, MJ Research, Watertown, Mass.). Sequencing reactions were purified over gel filtration cartridges (Edge Biosystems, Gaithersburg, Md.), and subjected to electrophoresis for 18 h at 2500 V, 40 mA on gels of 5.75% Page-Plus (Amresco Inc., Solon, Ohio)/ 6M Urea, 1×TBE, mobility file 4% and ABI 100 computerized base calling.

To clone a full length cDNA, a cDNA library was constructed from mRNA isolated from dexamethasone treated RBMC using the pSPORT1 vector system as described by the manufacturer (Gibco/BRL) (Wang and Brown, Proceedings of the National Academy of Sciences of the United States of America 88: 11505–9, 1991; Rivera-Gonzalez et al., J. of Steroid Biochemistry & Molecular Biology 64: 13–24, 1998). The CDNA library was plated, transferred to Hybond N membranes (Amersham, Arlington Heights, Ill.), denatured, crosslinked with a Stratalinker (Stratagene), and hybridized according to standard methods (Sambrook et al., *Molecular Cloning:A Laboratory Manual*, Cold Spring Harbor Laboratory Press, Cold Spring Harbor, N.Y., 1989). Hybridization probes were obtained by PCR using oligonucleotides:

195A (5'-GCCGCTCTAGAACTAGTGGATC-3') (SEQ ID NO: 9) and 195B (5'-AGGTCGACGGTATCGATAAGC-3') (SEQ ID NO: 10) to amplify the cDNA inserts from Bluescriptil SK+ (pBSSK+, Stratagene).

The amplified cDNA fragment was gel purified and labeled by random priming reaction using [$^{32}$P]-dCTP (Ready-to-Go Mix, Pharmacia, Piscataway, N.J.). Approximately one million colonies were screened by hybridization with 3 different [$^{32}$P]-labeled fragments from the subtractive cDNA library. Twenty eight positive dones were identified and sequenced.

The longest clone, 1664 bp named 51–35, hybridized to all 3 probes and was sequenced on both strands to confirm the sequence. The first nucleotide of the longest clone corresponds to base 17 in the full length SEQ ID NO: 1 shown in FIG. 1.

The 5'-end of the mRNA was determined by RNA ligase mediated rapid amplification of cDNA ends (RACE) as described previously (Frohman, *PCR Methods and Applications*, Vol. 4: S40–S58 (Cold Spring Harbor Laboratory Press, Cold Spring Harbor, N.Y., 1994). 50 µg total RNA from dexamethasone treated RBMC was dephosphorylated with calf intestinal alkaline phosphatase (Boehringer Mannheim, Indianapolis, Ind.) and the 5' cap was removed using tobacco acid pyrophosphatase (Epicentre Technologies, Madison, Wis.). The RNA linker generated from the plasmid pGbx-1 (Gift from Dr. Michael Frohman, Department of Pharmacology, SUNY, Stony Brook, N.Y.) was ligated to the decapped RNA using T4 RNA ligase (Epicentre Technologies, Madison, Wis.). The RNA was converted to cDNA by using Superscript II reverse transcriptase and poly dT(Robey, Connective Tissue Research 35: 131–6, 1996; Boskey, Connective Tissue Research 35: 357–63, 1996; Ducy et al., Nature 382: 448–52, 1996; Beresford, J. of Cell Science 102: 341–51, 1992; Herbertson and Aubin, Bone 21: 491–500, 1997; Rickard et al., J. of Bone & Mineral Research 11: 312–24, 1996; Maniatopoulos et al., Cell & Tissue Research 254: 317–30, 1988) primer (Gibco/BRL). PCR was used to amplify the 5'-end of the cDNA using primer pairs NRC-1-288A & 44A and NRC-1-288B & 44B in the first and second round, respectively. A single PCR product of ~420 bp was obtained in the second round PCR. A control sample in which the pyrophosphatase step was omitted did not yield a PCR product, indicating that the 420 bp product likely resulted from full length mRNA that had been 5'-capped. The second round PCR fragment was isolated and ligated using a TA Cloning Kit (Invitrogen, Carlsbad, Calif.). Insert containing plasmids were sequenced.

Gene specific primers:

44A: 5'-GTTAGGTAGTGCGTGCTTCG-3' (SEQ ID NO: 11)

44B: 5'-GGACATCTGTTGGAATTACGC-3' (SEQ ID NO: 12)

pGbx-1 RNA linker primers:

NRC-1-288A: 5'-CCAAGACTCACTGGGTACTGC-3' (SEQ ID NO: 13)

NRC-2-288B: 5'-CTAGAGGGGCCTGTTGAACC-3' (SEQ ID NO: 14)

2. Osteoregulin Characterization

Figures 7A, 7B:
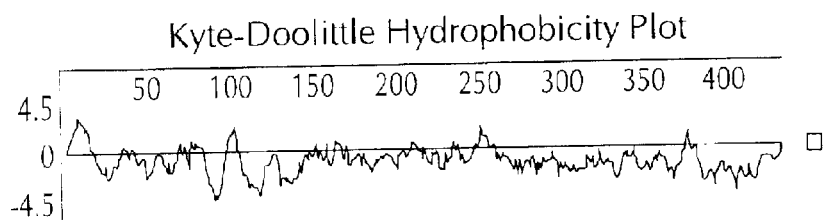
FIG. 7A is a hydrophathy plot of the rat osteoregulin polypeptide calculated according to Kyte-Doolittle algorithm, indicating a hydrophobic leader sequence at the amino terminus of the predicted amino acid sequence.
FIG. 7B describes the amino acid composition of the osteoregulin polypeptide, as predicted after proteolytic processing between Ala16 and Ala17.

A Kite-Doolittle hydrophobicity plot demonstrated that the sequence contained a hydrophobic leader sequence followed by a hydrophilic protein (FIG. 7A). Although the predicted amino acid sequence lacked the N-terminal positively-charged region (N-region) characteristic of a signal sequence for a secreted protein, it does contain an amino terminal hydrophobic region (H-region) characteristic of a signal sequence as described by von Hiejne (von Heijne, Nucleic Acids Research 14: 468–90, 1986). Analysis of the amino acid sequence with PSORTII, a program to predict the subcellular localization sites of proteins from their amino acid sequences indicates that this is likely to be an extracellular protein (Nakai and Kanehisa, Genomics 14: 897–911, 1992; McGeoch, Virus Research 3: 271–86, 1985). The predicted site of cleavage would be between Ala16 and Ala17. Assuming the actual cleavage occurs after Ala16, the secreted protein would be 419 amino acids in length with a calculated molecular weight of 44744.47 Da.

The predicted amino acid composition of the processed protein is shown in FIG. 7B. The sequence is rich in serine, glycine and charged residues. It would be a basic protein having a calculated pi of 8.67 with a net charge of +5.13 at neutral pH in the absence of post-translational modification. There are numerous potential phosphorylation sites including 9 consensus casein kinase II sites. Phosphorylation sites offer the potential for post-translational modification to increase the acidic character of the protein. Finally, sequence analysis reveals one consensus RGD integrin recognition motif characteristic of some extracellular matrix proteins (FIG. 1).

Comparison of the osteoregulin cDNA sequence to Genbank using the BLAST 1.4 algorithm (Altschul et al., J. of Molecular Biology 215: 403–10, 1990) showed little primary sequence homology to any known genes in the database. Weak homology was found to the protein DMP1 (also known as AG1) (George, J. of Biological Chemistry 268: 12624–30, 1993). The primary sequence homology is shown in the alignment in FIG. 8. Although the homology at the primary sequence level is relatively weak (22% identity, 37% similarity, Expect probability $3 \times 10^6$) there are general similarities that support the relatedness of these two proteins. Osteoregulin shares properties with DMP1 including the fact that both genes are highly charged, serine-rich, and contain a hydrophobic leader sequence. Osteoregulin is also analogous to DMP1 in that both genes exhibit a highly tissue restricted expression. DMP1 is most highly expressed in mature ondontoblasts, the tooth forming cells analogous to the bone forming osteoblasts that express osteoregulin mRNA (MacDougall et al., J. of Bone & Mineral Research 13: 422–31, 1998).

3. Expression Versus Other Osteoblast Markers

Northern blots analysis was used to detect gene expression changes over 21 days in culture in the differentiating RBMC (FIG. 9). RNA was isolated from cell culture with Trizol reagent (Gibco/BRL) according to a protocol modified for proteoglycan-rich sources (Chomczynski and Mackey, BioTechniques 19, 942–945,1995). Cells were homogenized in Trizol and extracted after the addition of chloroform. The aqueous phase was precipitated using 0.25 volume isopropanol and 0.25 volume 1.2 M NaCl / 0.8 M sodium citrate. The RNA was further purified by chloroform/sodium docecyl sulfate (SDS)/potassium acetate extraction as modified from Salvatori et al. (Salvatori et al., BioTechniques 13: 510–512, 1992). The RNA was resuspended in 0.6 ml of $H_2O$ and 0.07 ml of 20% SDS was added. Chloroform (0.3 ml) was added and mixed. Next, potassium acetate/glacial acetic acid (0.3 ml) was added, the sample was mixed and centrifuged 5 minutes 14,000×g. The aqueous layer was precipitated with 0.75 ml isopropanol, washed with 70% ethanol and resuspended in $H_2O$.

RNA was isolated from rat tissues using guanidine isothiocyanate extraction followed by a cesium chloride gradient (Sambrook et al., *Molecular Cloning:A Laboratory Manual*, Cold Spring Harbor Laboratory Press, Cold Spring Harbor, N.Y., 198925). Tissues were frozen in liquid nitrogen. Pools of tissues were homogenized in RNA extraction buffer (4 M guanidine isothiocyanate, 0.03 M sodium acetate, 0.4 gm/ml cesium chloride) and Sarkosyl was added to 0.5% (w/v). The homogenate was layered over a 3 ml pad of 5.7 M cesium chloride/03 M sodium acetate and centrifuged at 100,000×g for 14–16 hours. Total RNA was recovered and dissolved in $H_2O$.

For the Northern blots, 20 µg of total RNA was separated by electrophoresis through a 0.9% agarose-formaldehyde gel in 1×MOPS-acetate buffer (pH=7.0, transferred to Nytran membranes (Schleicher and Schuell, Keene, N.H.) and cross-linked. Filters were prehybridized at 42° C. in buffer containing 50% deionized formamide, 6×SSC (1×SSC=0.15 M NaCl, 0.015 M Na citrate pH 7), 7.5×Denhardts solution (1×Denhardts=0.02 gm/ml each of Ficoll, polyvinylpyrolidone and bovine serum albumin), 0.5% sodium dodecyl sulfate (SDS) and 100 µg/ml heat-denatured sonicated salmon sperm DNA. Hybridization was performed at 42° C. in fresh prehybridization buffer containing $1.5 \times 10^6$ cpm/ml cDNA probe labeled with [$^{32}$P]-dCTP using a random oligonucleotide priming kit (Pharmacia Biotech, Piscataway, N.J.). Following hybridization for 16–20 hours, the filters were washed 3 times in 0.3×SSC/0.1% SDS at room temperature followed by a 0.1×SSC/0.1% SDS wash at 55° C. for 30 minutes. Blots were exposed to a phosphoimaging screen and then filmed for varying times. Signals were quantified by phosphoimage analysis on a Fuji BAS 2000 (Fuji Medical Systems USA Inc., Stamford, Conn.). Different cDNA probes were used on the identical filters after stripping of the filters overnight in prehybridization buffer at 57° C. prior to adding the next radiolabeled cDNA probe.

Each cDNA probe was obtained by RT-PCR from either rat tibia or ROS 17/2.8 cell RNA. Specific probes regions are:

alkaline phosphatase: GenBank# J03572 309 bp; nucleotides 797–1106.

bone sialoprotein: GenBank# J04215 924 bp; nucleotides 116–1036.

osteocalcin: GenBank# X04141 290 bp; nucleotides 10–300.

osteonectin: GenBank# M99252 217 bp; nucleotides 757–974.

osteopontin: GenBank# M14656 766 bp; nucleotides 259–1025.

tartrate resistant acid phosphatase: GenBank# M76110 469 bp: nucleotides 218–687.

18S rRNA: GenBank# M29839 700 bp; nucleotides 377–1074.

As expected based on earlier literature, (Maniatopoulos et al., Cell & Tissue Research 254; 317–30, 1988; Rickard et al., Developmental Biology 161: 218–28, 1994; Leboy et al., J. of Cellular Physiology 146: 370–8, 1991) RBMC cultured in the absence of dexamethasone do not express mRNA of bone sialoprotein or osteocalcin, although they do express low levels of alkaline phosphatase, osteonecfin and osteopontin. Dexamethasone induced differentiation, as indicated by increased osteopontin, alkaline phosphatase, osteocalcin and bone sialoprotein mRNA expression. Osteoregulin mRNA was first detectable at 6 days and increased throughout the 21 days. Osteoregulin expression thus correlated with the increased differentiation toward the osteoblastic cell type. Temporally, osteoregulin expression was most similar to the expression of bone sialoprotein and osteocalcin in this culture system. These mRNAs are considered markers of mature osteoblasts, with expression occurring late in the differentiation program of osteoblasts (Aubin, Journal of Cellular Biochemistry 72: 396–410, 1999; Owen et al., J. of Cellular Physiology 143: 420–30, 1990; Rickard et al., Developmental Biology 161: 218–28, 1994).

4. Osteoregulin Tissue Distribution

Figure 9A:
FIG. 9A shows a multiple tissue Northern blot containing 2 µg poly A+RNA from, heart, lane 1; brain, lane 2; spleen, lane 3; lung, lane 4; liver, lane 5; skeletal muscle, lane 6; kidney, lane 7; and testis, lane 8. The blot was probed with a cDNA for osteoregulin followed by actin as a control.
Figure 9B:
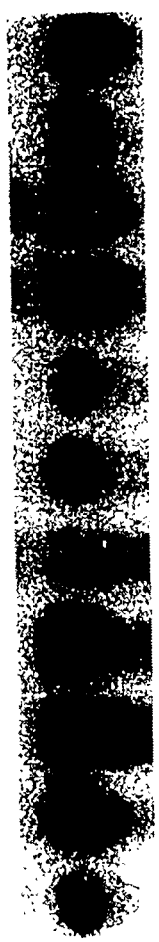
FIG. 9B shows a Northern blot analysis of 20 µg total RNA from pituitary, lane 9; tibial shaft, lane 10; uterus, lane 11; marrow, lane 12; tibial metaphysis, lane 13; intestine, lane 14; aorta, lane 15; RBMC +vehicle, lane 16; RBMC+dexamethasone, lane 17; brown fat, lane 18; and white fat, lane 19. The filter was probed for osteoregulin followed by an 18S control.

Osteoregulin was undetectable in polyA+ RNA from heart, brain, spleen, lung, liver, skeletal muscle, kidney and testis by Northern blot analysis (FIG. 9A). Hybridization of the identical filter with an actin probe demonstrated that the filter contained intact mRNA (FIG. 9A). In addition, 20 μg total RNA from pituitary, tibial shaft, uterus, marrow, tibial metaphysis, intestine, aorta, RBMC+/−dexamethasone, brown fat and white fat were probed for osteoregulin expression (FIG. 9B). Osteoregulin was expressed in tibial shaft and metaphysis as well as dexamethasone treated RBMC but was not detectable in other tissues. Based on these results, expression of osteoregulin was highly specific to bone.

Figure 10:
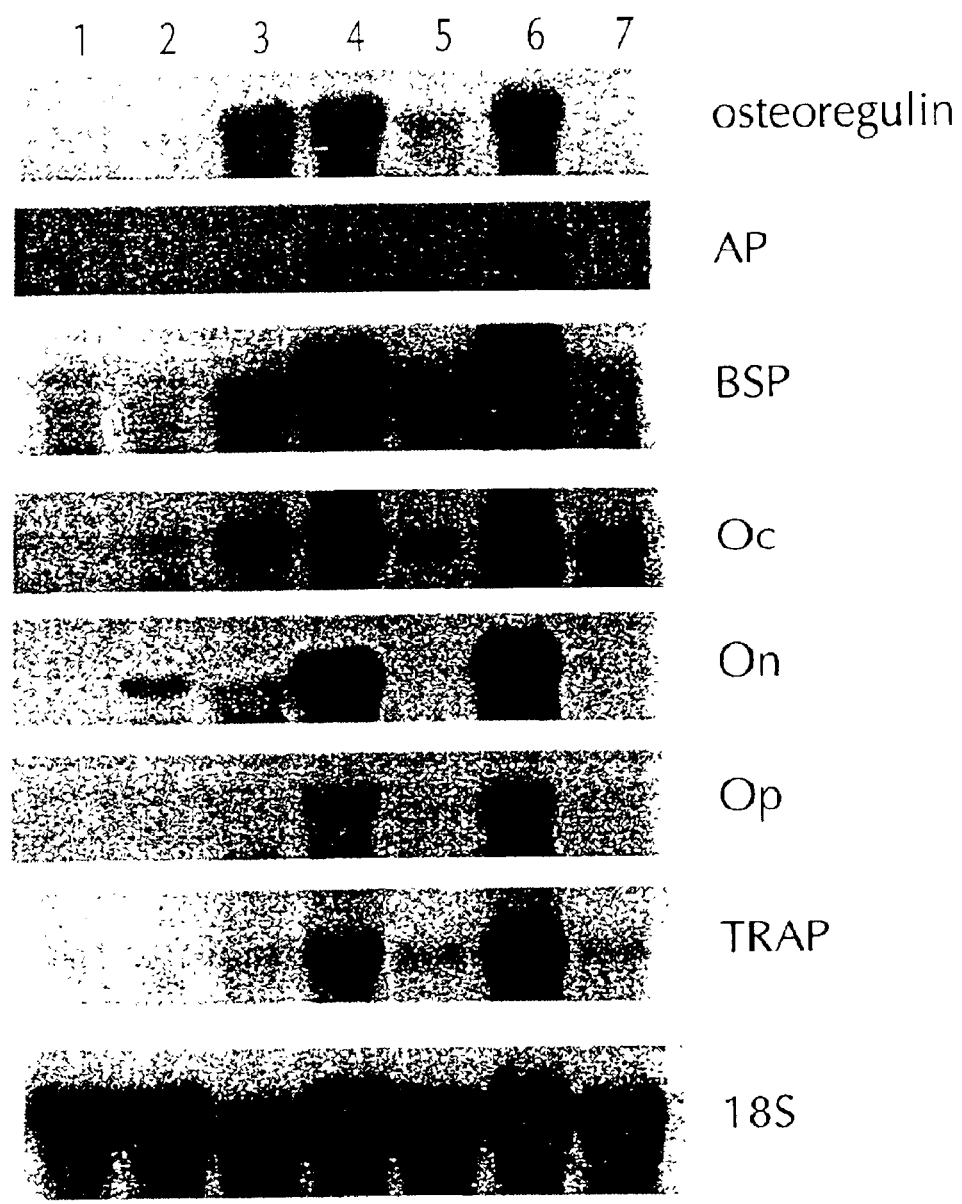
FIG. 10 depicts osteoregulin mRNA being highly expressed in rat tibial shaft, metaphysis and growth plate. Northern blot analysis of 20 µg of total RNA from marrow, lane 1; periosteum, lane 2; tibial shaft, lane 3; tibial metaphysis, lane 4; femoral neck, lane 5; tibial growth plate, lane 6; and calvaria, lane 7. The blot was probed sequentially for osteoregulin (OR), alkaline phosphatase (AP), bone sialoprotein (BSP), osteocalcin (Oc), osteonectin (On), osteopontin (Op), tartrate-resistant alkaline phosphatase (TRAP) and 18S rRNA (18S) as an internal control.

In order to further characterize the expression of osteoregulin in bone, total RNA from various bone compartments was subjected to Northern blot analysis (FIG. 10). Expression of osteoregulin was shown to be highest in tibial shaft, tibial metaphysis and tibial growth plate with lower expression seen in femoral neck and calvaria. Osteoregulin mRNA was not detectable in bone marrow or periosteum by this method. The expression of osteoregulin differed from that of other bone markers. Most notably, osteoregulin mRNA was expressed highly in the tibial midshaft. This sample represented primarily cortical bone. Other osteoblast markers such as alkaline phosphatase, osteopontin and osteonectin are expressed only at low levels in the cortical bone of tibial shaft. Similarly the osteoclast marker, tartrate-resistant alkaline phosphatase, is detectable only at low levels in the tibial shaft. Even in comparison to osteocalcin and bone sialoprotein, osteoregulin had a significantly different distribution. Osteoregulin has roughly equal expression in the tibial shaft versus tibial metaphysis and tibial growth plate, whereas osteocalcin and bone sialoprotein are less abundant in the tibial shaft versus the metaphysis or growth plate.

5. Expression in Osteoblastic Cell Lines

Although RBMC cultures consist predominantly of osteoblastic cells after dexamethasone treament, they did contain multiple cell types. The RNA derived from bone compartments was similarly derived from multiple cell types present in bone. In order to strengthen the evidence for osteoregulin expression in osteoblastic cells, we determined the expression pattern of osteoregulin in the well-characterized osteoblastic cell lines, UMR106 and ROS17/2.8 cells. UMR-106 cells were obtained from ATCC (American Type Culture Collection, Manassas, Va.) and maintained in DMEM/F12 media supplemented with 10% heat inactivated fetal bovine serum, and gentamycin 50 μg/ml (Gibco/BRL). Cells were plated in 10 cm bssue culture dishes and grown until 80% confluent. Cells were then switched into either control media containing 10 nM dexamethasone, or 10 nM dexamethasone and 50 μg/ml ascorbic acid. Cells were refed with fresh media 3 times per week and were extracted for RNA at either 24 h or 14 days using Trizol reagent as descibed below. ROS 17/2.8 cells were provided by Barbara Kream (The University of Connecticut Health Center, Division of Endocrinology and Metabolism, Farmington, Conn.) and were plated and treated in an identical manner as the UMR-106 cell cultures.

Figure 11:
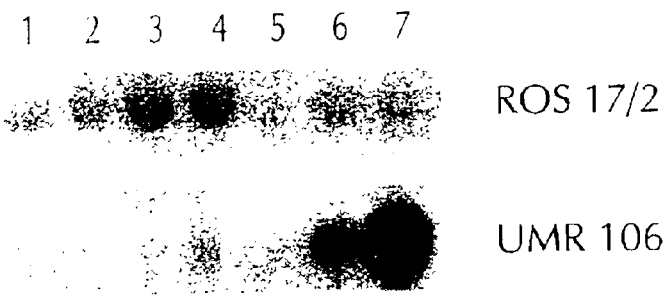
FIG. 11 is a Northern blot showing osteoregulin expression in immortalized osteoblastic cell lines. 20 µg of total RNA from UMR106 and ROS17/2.8 cells lane 1, time 0; lane 2, vehicle 1 day; lane 3, 10 nM dexamethasone 1 day; lane 4, 10 nM dexamethasone/50 µg/ml ascorbic acid 1 day; lane 5, vehicle 14 days; lane 6, 10 nM dexamethasone 14 days; lane 7, 10 nM dexamethasone/50 µg/ml ascorbic acid 14 days. The identical filter was sequentially probed for osteoregulin and 18S rRNA as an internal control.

Cells were cultured in the presence of dexamethasone or vehicle for either 1 or 14 days. Total RNA was extracted and Northern blot analysis was performed (FIG. 11). In UMR106 cells, osteoregulin mRNA was detectable at a low level on day 1 in the presence of dexamethasone or dexamethasone/ascorbic acid. By day 14, mRNA expression was increased in the presence of dexamethasone and was highest at day 14 in dexamethasone/lascorbic acid. ROS1712.8 cells cultured in the presence of dexamethasone or dexamethasone/ascorbic acid showed higher levels of expression at day 1 versus day 14. Clearly, osteoregulin mRNA was expressed in these osteoblastic cell lines.

Figure 12:
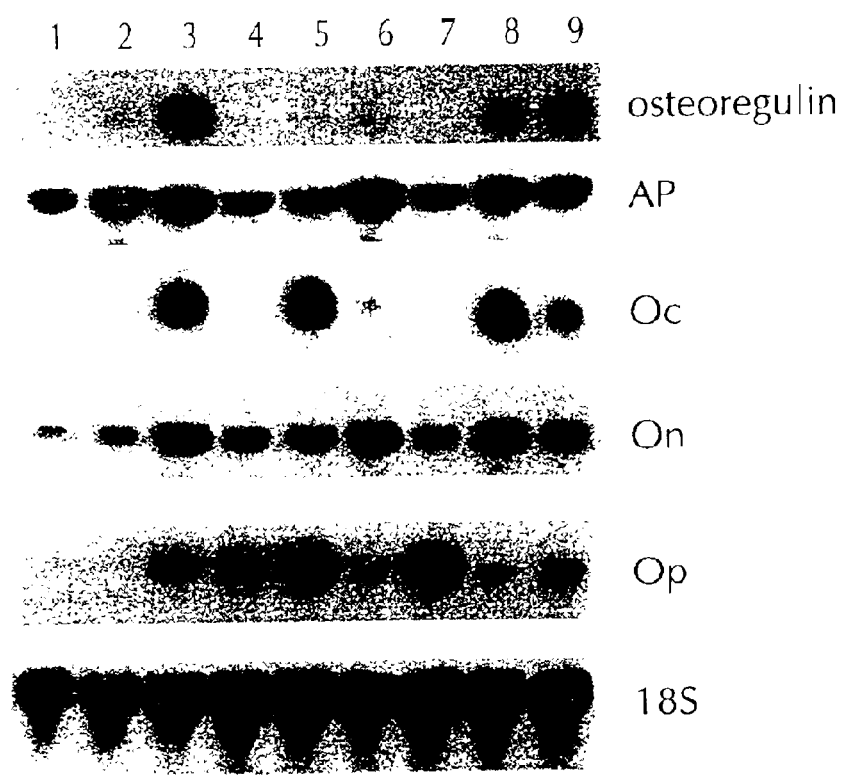
FIG. 12 is a Northern blot showing that the induction of osteoregulin mRNA differs from that of osteocalcin mRNA in UMR106 cells. Lane 1, 20 ug of total RNA from UMR106 cells treated with 10 nM dexamethasone for 2 days; lane 2, 10 nM dexamethasone for 3 days; lane 3, 10 nM dexamethasone for 10 days; lane 4, vehicle for 14 days; lane 5, 50 µg/ml ascorbic acid for 14 days; lane 6, 10 nM dexamethasone for 14 days; lane 7, 10 mM BGP for 14 days; lane 8, 10 nM dexamethasone and 50 µg/ml ascorbic acid for 14 days; lane 9, 10 nM dexamethasone, 10 mM BGP and 50 µg/ml ascorbic acid for 14 days was sequentially probed for the indicated messages. Alkaline phosphatase (AP), osteocalcin (Oc), osteonectin (On), osteopontin (Op), and 18S rRNA (18S) as an internal control.

The expression of osteoregulin mRNA in UMR106 cells under various differentiation conditions was compared to other osteoblast markers in UMR cells (FIG. 12). Consistent with FIG. 7, osteoregulin mRNA was induced by dexamethasone/ascorbic acid and to a lesser extent by dexamethasone alone. Osteocalcin and alkaline phosphatase were also induced by dexamethasone or dexamethasone/ascorbic acid. Although the pattern of osteoregulin induction resembled that observed for osteocalcin, differences were noted. That is, osteocalcin was induced over the length of culture even in the presence of ascorbic acid alone. In contrast, osteoregulin mRNA was not induced after 14 days with only ascorbic acid. Dexamethasone treatment was required for induction of osteoregulin.

6. Expression Vectors

A mammalian expression vector for rat osteoregulin was created by PCR amplification of the coding region (primer 36393.65E: 5'-AAGGTGAACGACACCAGAGAGC-3' (SEQ ID NO: 15) and 36392.65F: 5'-TGACCAAGTCTGGTACCTTGC-3') (SEQ ID NO: 16). The PCR fragment was cloned using a TA Cloning Kit (Invitrogen, Carlsbad, Calif.). The EcoRI digested insert from pCR2.1 was then subcloned in the correct orientation to the CMV mammalian expression vector pcDNA3 (Invitrogen, Carlsbad, Calif.).

For bacterial expression of osteoregulin protein, the complete coding region of osteoregulin was PCR amplified and subcloned to pCR2.1 using a TA Cloning Kit (Invitrogen, Carlsbad, Calif.) using primers (36318.170A
5'-GCCGGATCCATGCAGGCTGTGTCTGTTGGAC-3' (SEQ ID NO: 17) and 36318.170B 5'-GCCGMTTCCAGGACCAGAGCTGGGAAC-3' (SEQ ID NO: 18). The correct orientation insert in pCR2.1 (Invitrogen) was subcloned using the BamHI site incorporated into the PCR primer and the NotI site of pCR2.1 in-frame into the BamHI/NotI sites of the bacterial expression plasmid pET-28a (Novagen, Madison, Wis.). This construct created a fusion protein with a $(His)_6$-Tag and T7-Tag at the amino terminus. A GST-fusion protein was created by subcloning the BamHI/EcoRI fragment in the E. coli expression construct pGEX-2TK (Pharmacia, Piscataway, N.J.).

The GST fusion protein expression was induced by isopropyl-β-D-galactose (IPTG) in the bacterial strain BL-21 (DE3) (Novagen) as suggested by the vector manufacturer (Pharmacia, Piscataway, N.J.). The majority of the osteoregulin fusion protein was present in the insoluble inclusion bodies. The recombinant protein was solubilized from the inclusion bodies with 8 M urea/0.5 M Tris HCl (pH 8)10.5 M NaCl/1 mM EDTA/1 mM DTT.

The pET28a His-Tag osteoregulin fusion protein was expressed in the bacterial strain BL-21 (DE3) (Novagen, Madison, Wis.) and purified from inclusion bodies on Ni-NTA Superflow resin as described by the manufacturer (Qiagen, Valencia, Calif.). The protein was eluted from the NTA resin in 8 M urea/0.1 M NaPO$_4$/0.01 M Tris HCl pH 4.5.

7. Immunohistochemistry

Affinity purified anti-osteoregulin polyclonal antibodies were generated and used to localize osteoregulin protein expression in normal adult bone tissue by immunohistochemistry. High titer polyclonal antisera was generated by immunization of rabbits by Research Genetics (Huntsville, Ala.). A polyacrylamide gel slice containing about 20 mg of highly purified GST-osteoregulin fusion protein was used as the immunogen. This material was obtained by SDS-PAGE purification of GST-osteoregulin fusion protein that was solubilized from the Inclusion bodies.

The His-Tag osteoregulin fusion protein expressed in pET28a was renatured by exhaustively dialyzing versus 0.2 M NaHCO$_3$/0.5 M NaCl pH 8.3 at 4° C. The dialyzed protein was then coupled to cyanogen bromide activated Sepharose 4B at 4° C. overnight as suggested by the manufacturer (Pharmacia). Approximately 5 mg protein/ml of resin was coupled.

Osteoregulin antibody was affinity purified as described (Harlow and Lane, *Antibodies: A Laboratory Manual*, Cold Spring Harbor Laboratories Press, Cold Spring Harbor, N.Y., 1988). Briefly, 5 ml of antiserum was diluted in 10 mM Tris HCl (pH 7.5) and applied by batch to resin coupled to osteoregulin as above. The column was washed extensively with 10 mM Tris HCl (pH 7.5) and then with 500 mM NaCl, 10 mM Tris HCl (pH 7.5). Acid sensitive interactive antibodies were eluted with 100 mM glycine (pH 2.5) and collected in a tube containing one bed volume of 1 M Tris-HCl (pH 8). Base sensitive antibodies were eluted using 100 mM triethylamine (pH 11.5) collected into a tube containing 1 M Tris HCl (pH 8). The two fractions were dialyzed extensively against PBS (pH 8.0) containing 0.02% sodium azide and tested for reactivity by Western analysis.

The binding of the affinity purified antibody was characterized by Western blot analysis on protein extracts from cells that had been transfected with expression vectors expressing osteoregulin. Samples were separated by electrophoresis on Novex (San Diego, Calif.) 10% Bis-Tris gels and transferred using a semi-dry transfer system to nitrocellulose. Blots were blocked using 1% Western Blocking Reagent from Roche (Mannheim, Germany) for 1 hour and primary antibody diluted in 0.5% block was added for 1 hour. After washing, a goat anti-rabbit peroxidase secondary antibody (Roche) was diluted into 0.5% block and applied to the blot for 1 hour. After washing, signal was detected and quantitated using an ECL detection kit from Amersham (Buckinghamshire, England) following the manufacturer's instructions.

Adult rat tibias were fixed in 4% paraformaldehyde and decalcified in 10% EDTA. Bones were embedded using standard techniques into paraffin and 5 micron sections were placed onto silanated slides (Digene, Beltsville, Md.) and heated overnight at 50° C. Slides were rehydrated and endogenous peroxidase activity was blocked by incubating sections in 3% H$_2$O$_2$ in methanol. Antigenic sites were exposed by pepsin digestion at 20,000 units in 00.1 M HCl. Sections were blocked in 1% BSA/PBS and incubated overnight at 4° C. in a humidified chamber with primary antibody diluted at 1:500 in 0.1% BSA/PBS or rabbit IgG (Vector Laboratory Inc., Burlingame, Calif.) as a control. Secondary antibody, consisting of anti-rabbit IgG Fab fragments linked to horseradish peroxidase (Amersham Life Sciences), was diluted at 1:100 in 0.1% BSA/PBS and placed onto tibia sections for 1 hour at room temperature. Detection was performed using a DAB substrate chromagen system (Vector Laboratory Inc.) according to the manufacturer's instructions.

To assess the ability of the tibia and femur cells to mineralize, cultures were maintained in 50 µg/ml sodium ascorbate/10 nM dexamethasone/10 mM β-glycerophosphate and stained by Von Kossa staining to assess mineral deposition. Marrow was isolated from the tibia and femur of 3 month old Sprague Dawley female rats and placed into Minimum Essential Medium (MEM) culture medium supplemented with 15% fetal calf serum, 2 mM glutamine, 0.1 mg/ml gentamicin, 100 U/ml penicillin and 100 µg/ml streptomycin; Gibco/BRL, Gaithersburg, Md.). Isolated marrow cells were filtered through 100 µm mesh, washed 3x with culture medium and plated into 10 cm tissue culture dishes at a density of $1 \times 10^6$ cells/cm$^2$. Cells were allowed to attach for 4 days undisturbed at 37° C. with 5% CO$_2$. Cells were grown until 90% confluent at which time they were treated with 50 µg/ml sodium ascorbate and 10 nM dexamethasone in culture medium. Medium was changed 3 times per week after the initial attachment period.

Specific staining was detected in osteocytic cells within both trabecular and cortical surfaces indicating expression in highly differentiated osteoblasts. There was no specific staining detected in osteoclasts, chondrocytes or periosteal cells. Also, cells of the hematopoetic lineage contained in the marrow compartment were negative for osteoregulin.

Mouse Osteoregulin

1. Isolation and Characterization

A complete mouse cDNA with a high degree of homology to rat osteoregulin was cloned (SEQ ID NO: 3, FIG. 1) using low stringency hybridization and PCR. A 1255 bp probe encoding most of the rat osteoregulin cDNA sequence excluding the 3'-UTR was obtained by digestion of the rat osteoregulin cDNA library clone at a SalI site within plasmid pSPORT (Invitrogen) and the internal XhoI site within the cDNA. A mouse 129 genomic lamda library was plated and transferred to Hybond N+ filters according to standard protocols (Sambrook et al., *Molecular Cloning: A Laboratory Manual*, Cold Spring Harbor Laboratory Press, Cold Spring Harbor, N.Y., 1989). Filters were hybridized overnight at 65° C. with $1 \times 10^6$ cpm/ml in 5xSSC15x Denhardts15% dextran sulfate/0.5% SDS/500 µg/ml salmon sperm DNA. The filters were washed 2 times 20 minutes in 2xSSC/0.1% SDS at 25° C., 2 times 20 minutes in 2xSSC/0.1% SDS at 65° C. and a final 20 minutes wash in 1xSSC/0.1% SDS at 65° C. Positive plaques were purified by two additional rounds of hybridization screening. Efforts focused on an approximately 15 kB lambda clone that hybridized to the probe.

The 5'-end of the mRNA was determined by RNA ligase mediated RACE as described above. 50 µg total RNA from mouse Ubia was dephosphorylated with calf intestinal alkaline phosphatase (Boehringer Mannheim, Indianapolis, Ind.) and the 5' cap was removed using tobacco acid pyrophosphatase (Epicentre Technologies, Madison, Wis.). The RNA linker generated from the plasmid pGbx-1 (Gift from Dr.

Frohman, Department of Pharmacology, SUNY, Stony Brook, N.Y.) was ligated to the decapped RNA using T4 RNA ligase (Epicentre Technologies, Madison, Wis.). The RNA was converted to CDNA by using Superscript II reverse transcriptase and poly dT(Robey, Connective Tissue Research 35: 131–6, 1996; Boskey, Connective Tissue Research 35: 357–63, 1996; Ducy et al., Nature 382: 448–52, 1996; Beresford, J. of Cell Science 102:341–51, 1992; Herbertson and Aubin, Bone 21: 491–500, 1997; Rickard et al., J. of Bone & Mineral Research 11: 312–24, 1996; Maniatopoulos et al., Cell & Tissue Research 254: 317–30, 198812–18) primer (Gibco/BRL). PCR was used to amplify the 5'-end of the CDNA using primer pairs NRC-1-288A & 36387.233B and NRC-1-288B & 36387.233A in the first and second round, respectively. A single PCR product of approximately 550 bp was obtained in the second round PCR. A control sample in which the pyrophosphatase step was omitted did not yield a PCR product, indicating that the approximately 550 bp product likely resulted from full length mRNA that had been 5'-capped. The second round PCR fragment was isolated and ligated using a TA Cloning Kit (Invitrogen, Carlsbad, Calif.). Insert containing plasmids were sequenced.

The 3'-end of the mRNA was determined using a 3' RACE kit as suggested by the manufacturer (Gibco/BRL). 5 µg mouse tibia total RNA was reverse transcribed using the AP primer provided. The PCR reaction used primer 36387.233E and the AUAP primer provided. Two fragments close in size were doned with the TA Cloning Kit (Invitrogen) and sequenced. The sequence of the 2 fragments were identical except for a short stretch of additional sequence at the 3'-end.

Gene specific primers:
36387.233A: 5'-TGTGTCAGGTAGTGAGTGCTCC -3' (SEQ ID NO: 19)
36387.233B: 5'-ACTGCCACCATGTCCTTCTC -3' (SEQ ID NO: 20)
pGbx-1 RNA linker primers:
NRC-1-288A: 5'-CCAAGACTCACTGGGTACTGC-3' (SEQ ID NO: 21)
NRC-2-288B: 5'-CTAGAGGGGCCTGTTGAACC-3' (SEQ ID NO: 22)

The cDNA was 1741 bp in length, encoding a 441 amino acid protein. Alignment with the rat amino acid sequence demonstrated approximately 70% identity (FIG. 5). Importantly, key structural features were conserved. Both proteins were rich in serine, glycine and charged amino acids and included an amino terminal hydrophobic region that appears to be a signal sequence targeting the peptide for secretion. The RGD sequence, an element potentially involved in cell-matrix interactions through integrin binding and signaling, was also conserved (FIG. 1).

2. Tissue Distribution

Mouse osteoregulin mRNA was expressed in primary mouse calverial and bone marrow cell cultures stimulated to mineralize. Bone marrow was harvested by centrifugation from the femur and tibia. Cell pellets were triturated and passed through a 100 µm filter. Cells were counted and plated at a density of $4\times10^5$ cells/cm$^2$. Cells were grown in MEM alpha medium supplemented with 10% FBS and 50µg/ml gentamycin. The media was changed on day 7. On day 10, cells were either stimulated to form mineralized nodules with MEM-alpha media (+FBS and gentamycin) supplemented with β-glycerophosphate (10 mM) and L-ascorbic acid (50 µg/ml) or left unstimulated and fed the standard MEM-alpha media (+FBS and gentamycin) without added supplementation. Media was changed every 3 days, and aliquots of cells were harvested for RNA or Van Kossa staining at several timepoints.

Whole calvarium were dissected from postnatal day 3 mouse pups. Calveria were rinsed twice with cold PBS and digested in 10 ml enzyme cocktail. Cocktail included 0.2 mg/ml Collagenase P (Boehringer Mannheim, Indianapolis, Ind.) dissolved in serum-free MEM (Gibco BRL) and 0.25% trypsin solution (Gibco BRL, Cat. No. 15090) After 15 minutes, the cocktail was removed and discarded, the calveria rinsed with PBS and new cocktail added. After 30 minutes, cells were filtered through a 70 µm filter and 4 ml of FBS added to neutralize proteases. Cells were then washed in PBS twice, resuspended in MEM-alpha (10% FBS and 50 µg/ml gentamycin) and cell number counted. Calverial cells were plated at $2\times10^4$ cells /cm$^2$. Cells were fed every 3 days until nearly confluent. Calverial cultures were then stimulated to differentiate with MEM-alpha (10% FBS and 50 µg/ml gentamycin) supplemented with 50 µg/ml L-ascorbic acid and 10 mM β-glycerophosphate. Cells were harvested for RNA or Van Kossa staining at designated timepoints as described above.

Osteoregulin mRNA appeared at 7 days of ascorbic acid/β-glycerol phosphate treatrnent in calverial cultures and reached a plateau by 14 days. Osteoregulin expression was detected after 7 days in bone marrow cultures and reached a plateau by 21 days. This pattern of expression suggested osteoregulin was induced in the osteoblast lineage as the cells proceeded down their differentiation program. This pattern directly paralleled what has been observed previously for the rat mRNA.

Figure 13A:
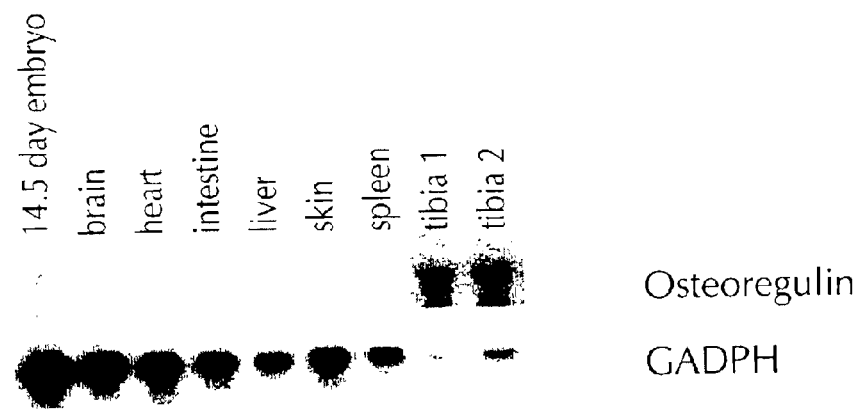
FIG. 13A is a Northern blot analysis of osteoregulin expression in various mouse tissues which indicates bone specific expression of the osteoregulin gene.
Figure 13B:
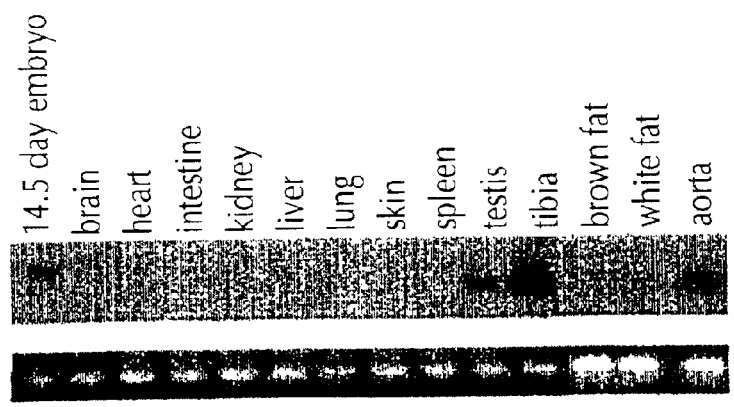
FIG. 13B (upper panel) shows a Southern hybridization blot of reverse transcription (RT)-PCR of assorted mouse tissues with primers specific for osteoregulin. In addition to bone, the osteoregulin message is detected at very low levels in the embryo, testes, brown and white fat, and the aorta. The lower panel represents actin primer RT-PCR product for each RNA sample.

The mRNA tissue distribution by Northern blot analysis indicated that osteoregulin was highly bone-specific in mouse (FIG. 13). A high level of osteoregulin message was detected in mRNA prepared from mouse tibia, but all other tissues are negative, even when polyA+ mRNA was probed. Using the very sensitive technique of Southern analysis of cDNA amplified by RT-PCR, low levels of osteoregulin mRNA were detected in brown fat, white fat, testes, and aorta. Expression of osteoregulin in the aorta appeared to be significant, especially under pathophysiological conditions where vascular calcification can occur (Schinke et al., Annals of Medicine 30: 538–41, 1998).

The predominant expression of osteoregulin in bone tissue was further confirmed by expression of a reporter gene under the regulatory control of osteoregulin gene promoter elements. Two murine fragments 450 bp and 4.5 Kb long, representing sequence adjacent to and upstream of the osteoregulin ATG start site, were cloned into the PGL3 basic vector (Promega) in operable linkage with a luciferase reporter gene sequence. Vectors encoding each of these upstream fragments were transfected into separate samples of the bone cell line UMR as well as a human embryonic kidney cell line HEK293. Both upstream fragments directed expression of luciferase in the bone cell line, and luciferase expression was increased following dexamethasone administration. By contrast, luciferase activity was not increased in the kidney cell line above control levels. Therefore, either the 450 bp or 4.5 kb fragment contains a functional expression element(s) that regulates expression in a physiologically relevant, tissue-specific pattern.

To clone the 450 bp upstream fragment, the following Hind III fragment of the mouse osteoregulin promoter was cloned into the Hind III site of the pGL3 vector (a potential CBFA site is underlined; a potential CCAAT box is highlighted in bold). AGCTTCTCTAATGTCCGCCCTAT-GGTAGGTGCTCAAAGCATCATTGGTGTCTGAATAA-GATTCAGATACAATTAAGGTTGTACATTCTCTAAAT- AAAACAACAAAACTACTTTTCACTTATAAATTTGT-
TGGTTTACAAATATTTCCTACTTACACGTATGCAAC-
CCATTCACCCAGTCCTAGTTAATAGTTCTAAAAATC-
AGTTCTAATTATTTTGCAACATAATGTCCAAACTG-
AGATATTTATATTTTTTTCTGTTTATTCTACTTTCTG-
GAACATTTGATAGCAGCTTTCCACCACAAAACATT-
TTTAGATTAAAATTACCATACCCCCTGTGGTCATCT-
GTGGGCATTTGTGACAGACTCCGTGCTGGTACTGA-
GTGAACCATGCTGATTGGACATCGGGGGCTCTCA-
CAAACTTTAAATTTCAGCAAATGCCCAGAGACTA-
AGCCCGAAGAAGCCAAGCT (SEQ ID NO: 43)

The 4.5 kb upstream fragment of the mouse osteoregulin promoter included SEQ ID NO: 44 as well as additional 4.1 kb sequence upstream of SEQ ID NO: 43. This 4.5 kb fragment was cloned into the pGL3 vector by partial digest of a 20 Kb Spe fragment suclored from the mouse BAC clone #17535.

3. Expression Vectors

For mammalian expression, sequence information obtained from the genomic lambda clone was used; 5'- and 3'-RACE primers were designed to amplify 1340 bp containing the coding region of the mouse osteoregulin cDNA. (36393.44C: TTTCCTGAAGGTGAATGACG-3' (SEQ ID NO: 23) & 36393.44H: 5'-CTAGTCACCATGACTCTCA-CTAG-3') (SEQ ID NO: 24). A 1340 bp fragment was generated by PCR, cloned to pCR2.1 using a TA Cloning Kit (Invitrogen, Carlsbad, Calif.) and sequenced. The EcoRI digested insert from pCR2.1 was then subcloned in the correct orientation to the CMV mammalian expression vector pcDNA3 (Invitrogen, Carlsbad, Calif.).

For bacterial expression of osteoregulin protein, the complete coding region of osteoregulin was PCR amplified and subcloned to pCR2.1 using a TA Cloning Kit (Invitrogen, Carlsbad, Calif.) using primers (41766.188A 5'-GCCGGATCCATGACGCCAGAGGGCC-3' (SEQ ID NO: 25) and 36393.44H 5'-CTAGTCACCATGACTCTC-ACTAG-3') (SEQ ID NO: 26). The insert in pCR2.1 was subcloned using the BamHI site incorporated into the PCR primer and the EcoRI site site of pCR2.1 in-frame into the BamHI/EcoRI sites of the bacterial expression pGEX-6P (Pharmacia). This construct created a fusion protein with GST at the amino terminus which can be cleaved with PreScission Protease (Pharmacia). The GST fusion protein expression was induced by IPTG in the bacterial strain BL-21 (DE3) (Novagen) as suggested by the vector manufacturer (Pharmacia). The majority of the osteoregulin fusion protein was present in the insoluble inclusion bodies. The fusion protein was solubilized from the inclusion bodies with 8 M ureal0.5 M TrisHCl (pH 8)10.5 M NaCl/1 mM EDTA/1 mM DTT. Approximately 16 mg of 8 M urea soluble protein was further purified by SDS-PAGE. The osteoregulin-GST protein was identified by staining with Coomassie Blue for five minutes; the gel band was excised.

In a preferred method to reduce the proteolytic degradation that occurred within the host bacteria, we also generated an E. coli expression construct that omitted the largely hydrophobic stretch of 26 amino acids present at the amino terminus. A region of osteoregulin cDNA was PCR amplified and subcloned to pCR2.1 using a TA Cloning Kit (Invitrogen, Carlsbad, Calif.) using primers (41766.252A 5'-GGATCCATGCCGAATGAAGACAGGA-3' (SEQ ID NO: 27) and 36393.44H 5'-CTAGTCACCATGACTCTC-ACTAG-3') (SEQ ID NO: 28). The pCR2.1 insert was further subdoned using the BamHI site incorporated into the PCR primer and the NotI site of pCR2.1 into the BamHI/NotI sites of the bacterial expression pGEX6P (Pharmacia). This expression construct was called m51-35delta-pGEX.

Mouse osteoregulin-GST fusion protein was expressed by induction with IPTG in the bacterial strain BL-21 (DE3) (Novagen). The bacterial pellet was lysed by freeze thawing and sonication in lysis buffer (50 mM Tris-HCl pH 7.5/100 mM NaCl/0.5% Triton X100/1 mM EDTA/5mM DTT plus 1 complete protease inhibitor tablet (Boehringer Mannheim) per 40 ml). The soluble protein was purified on GST-Sepharose and cleaved with PreScission™ Protease by the on-resin protocol as suggested by manufacturer (Pharmacia). The isolated protein was further purified by cation exchange chromatography on a HiTrap™ SP column (Pharmacia). Highly purified osteoregulin protein was eluted from the SP column at about 0.4 M NaCl.

4. Immunohistochemistry

High titer polyclonal antisera was generated by immunization of rabbits by Zymed Laboratories Inc. (South San Francisco, Calif.). The initial immunogen was an SDS PAGE gel slice containing full length osteoregulin fused to GST expressed from the pGEX6P vector. The immunogen for the final boost was the soluble, highly purified osteoregulin protein lacking the GST and amino terminal leader sequence that was obtained after purification on the HiTrap SP cation exchange column. The murine anti-osteoregulin antibodies were affinity purified as described for rat antibodies.

The expression of osteoregulin at the protein level was determined by immunohistochemical analysis of longitudinal tibia sections. Mouse osteoregulin protein was expressed in osteoblasts and osteocytes, again consistent with the rat osteoregulin expression pattern. There was no specific staining detected in osteoclasts, chondrocytes or periosteal cells. Also, cells of the hematopoetic lineage contained in the marrow compartment were negative for osteoregulin.

5. Genomic Organization and Targeting of the Osteoregulin Gene

The genomic DNA encoding mouse osteoregulin was cloned and mapped using a BAC done. A 124 bp probe for the 5'-end of the cDNA was generated by PCR with primers 36393.80A: 5'-TTTCAGCAAATGCCCAGAG-3' (SEQ ID NO: 29) and 36393.80B: 5'-CCAGGTCATACTGAAGAGGAGC3'. (SEQ ID NO: 30). Mouse tibia CDNA was used as a template. The 124 bp insert was isolated from low melting point agarose and sent to GenomeSystems Inc. (St. Louis, Mo.) for screening of a mouse ES-129/SVIII BAC library by hybridization screening. A single clone was identified and characterized.

The mouse osteoregulin gene was comprised of three exons, two small 76 and 78 bp exons separated from the third 1597 bp exon by 10.5 kb (FIG. 14). Fluorescence in situ hybridization (FISH) analysis was conducted by GenomeSystems Inc. according to their protocols and determined that the osteoregulin gene is located on mouse chromosome 5, region 5E3-E5. Briefly, DNA from the mouse BAC clone was labeled with digoxigenin dUTP by nick translation. Labeled probe was combined with sheared mouse DNA and hybridized to normal metaphase chromosomes derived from mouse embryo fibroblast cells in a solution containing 50% formamide, 10% dextran sulfate and 2xSSC. Specific hybridization signals were detected by incubating the hybridized slides in flouresceinated anti-digoxigenin antibodies followed by counter staining with DAPI.

The initial FISH experiment resulted in specific labeling of a medium sized chromosome which was believed to be chromosome 5 on the basis of DAPI staining. A second experiment was conducted in which a probe which is specific for the centromeric region of chromosome 5 was cohybridized with the mouse BAC clone. This experiment resulted in the specific labeling of the centromere and the middle portion of chromosome 5. Measurements of 10 specifically labeled chromosomes 5 demonstrated that the osteoregulin gene is located at a position which is 62% of the distance from the heterochromatic-euchromatic boundary to the telomere of chromosome 5, an area that corresponds to band 5E3-E5. A total of 80 metaphase cells were analyzed with 72 exhibiting specific labeling.

A targeting vector was constructed to delete the third and largest exon of osteoregulin and replace it with the neomycin selectable marker gene (FIG. 14). Standard gene mapping and sublconing methods were used to map the genomic locus of osteoregulin and construct a targeting vector (Sambrook et al., *Molecular Cloning:A Laboratory Manual*, Cold Spring Harbor Laboratory Press, Cold Spring Harbor, N.Y., 1989). The following restriction enzymes were used for mapping and generating a targeting construct of the osteoregulin locus: Not I, Xba I, Spe I, Bam HI, and Xho I (New England Biolabs, Beverly, Mass.). Restriction mapping, Southern hybridization and sequence data confirmed the localization of the third exon of osteoregulin within a 3 kb Xba/Spe genomic restriction fragment. Genomic DNA fragments from the osteoregulin locus were cloned into the JNS2 targeting plasmid (Dombrowicz et al., Cell 75: 969–76, 1993). A 1.8 kb Not I/Xba1 genomic fragment of 5' homology was cloned into the NotI and Xba1 sites of pBluescript (Stratagene) and then removed with NotI and XhoI to clone into the NotI and XhoI sites of JNS2, 5' of the neomycin selectable marker gene. An 8 kb SpeI/XbaI fragment of 3' homology was cloned into the Xba I site of JNS2 in a position 3' to the neo cassette. Successful recombination of this targeting vector with the osteoregulin locus results in the replacement of a 3.0 kb fragment region of the osteoregulin gene with the neomycin selectable marker gene. Recombination of this targeting vector with the osteoregulin locus results in the introduction of a Bam HI site to the locus via the neomycin gene insertion. Targeting events in embryonic stem cells were detected by Southern blot hybridization using a 500 bp Xba I/Bam HI probe homologous to a region 3' of the targeting homology. Following Bam HI digestion of ES cell DNA, a 15 kb hybridizing band was detected in the untargeted allele, and an 8 kb hybridizing band was detected in the targeted allele. This deletion removed the DNA encoding Met27 through the end of the translated sequence including the final Asp441 of SEQ ID NO: 4.

The E14Tg2a embryonic stem (ES) cell line derived from the 129sj mouse strain was used for gene targeting of the osteoregulin locus (Hooper et al., Nature 326: 292–5, 1987). Pluripotent ES cells were maintained in culture on a mitomyocin C treated primary embryonic fibroblast (PEF) feeder layer in stem cell medium (SCML) which consisted of D-MEM (Life Technologies, Inc., Gaithersburg, Md, Catalog No. LTI #10829-018) supplemented with 15% ES cell qualified fetal calf serum (Life Technologies, Inc., Catalog No. LTI #10439-024), 0.1 mM 2-mercaptoethanol (Sigma, St. Louis, Mo., #M-7522), 0.2 mM L-glutamine (Life Technologies, Inc., Catalog No. LTI #25030-081), 0.1 mM MEM non-essential amino acids (Life Technologies, Inc., Catalog No. LTI # 11140-050), 1000 u/ml recombinant murine leukemia inhibitory factor (ESGRO, Life Technologies, Inc., Catalog No. LTI#13275-029) and penicillin/streptomycin (Life Technologies, Inc., Catalog No. LTI #15140-122).

Electroporation of $1\times10^7$ cells in SCML and 25 $\mu$g linearized targeting vector was carried out using a BTX Electro Cell Manipulator 600 (BTX, Inc., San Diego, Calif.) at a voltage of 280 v, a capacitance of 50 $\mu$f and a resistance of 360 ohms. Positive/negative selection began 24 hours after electroporation in SCML which contained 200 $\mu$g/ml G418 (positive) and 2 $\mu$M gancyclovir (negative). Resistant colonies were picked with a micropipette following 8–10 days of selection. Expansion and screening of resistant ES cell colonies was performed as described in Mohn and Koller (Mohn, *DNA Cloning* 4 (ed. Hames), 143–184 Oxford University Press, New York, 1995). Out of 70 neomycin and gancyclovir resistant clones, four were positive for the desired recombination event, resulting in a targeting frequency of 1 in 17.

Preparation of cells for injection was performed as described in Mohn and Koller (Mohn, *DNA Cloning* 4 (ed. Hames), 143–184 Oxford University Press, New York, 1995). Ten to fifteen targeted ES cells were introduced into the blastocoel of C57BL/6 embryos and the embryos were allowed to continue development by reintroducing them into a pseudopregnant foster mother. Chimeras showing greater than 90% contribution of ES cells based on the coat color were mated with C57BL/6 mice. A 850 bp Spe I/Msc I probe, homologous to a region directly 3' of the targeted mutation was used to genotype agouti offspring by Southern blot analysis. Digestion of tail DNA with Bam HI/BgI I double digest resulted in a 10 kb hybridizing band in the wild type allele and a 9 kb hybridizing band in the targeted allele.

RNA was prepared from the following mouse tissues: aorta, tibia (wild type, knockout, and heterozygous), 14.5 day embryo, brain, heart, intestine, kidney, liver, lung, skin, spleen, and testes. The RNA was converted to cDNA by using Superscript II reverse transcriptase and poly dT(12–18) primer (Gibco/BRL). PCR was used to amplify an internal 483 bp cDNA using primer pairs:

36499-143A: 5'-ACTATCCACAAGTGGCCTCG-3' (SEQ ID NO: 31) and 36499-143B:5'-CTGTTGGCTTGCTCAGTTCC-3'. (SEQ ID NO: 32). Eight $\mu$l of the PCR reaction product was electrophoresed on a 1% TAE agarose gel. The DNA was transferred to a Nytran filter by standard Southern blot methods and Stratalinked. The blot was then hybridized with a 861 bp radiolabeled cDNA probe as described above for Northern blots.

Figure 15A:
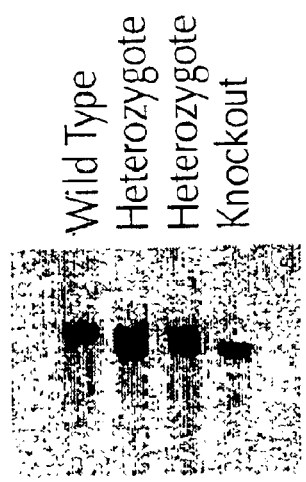
FIG. 15A is a Southern blot analysis of tail DNAs to assess the targeted disruption of the osteoregulin locus in mice. Tail DNA was digested with Bam HI and BgI I and hybridized with Probe 2. A 10 kb band is detected at the wild type allele and a 9 kb band is detected at the targeted allele.
Figure 15B:
FIG. 15B is a Southern hybridization blot of RT-PCR of RNA prepared from bone of wild type, heterozygous, and knockout animals. Note the reduced message in the heterozygote lane and the absence of message in the knockout lane.
Figure 16A:
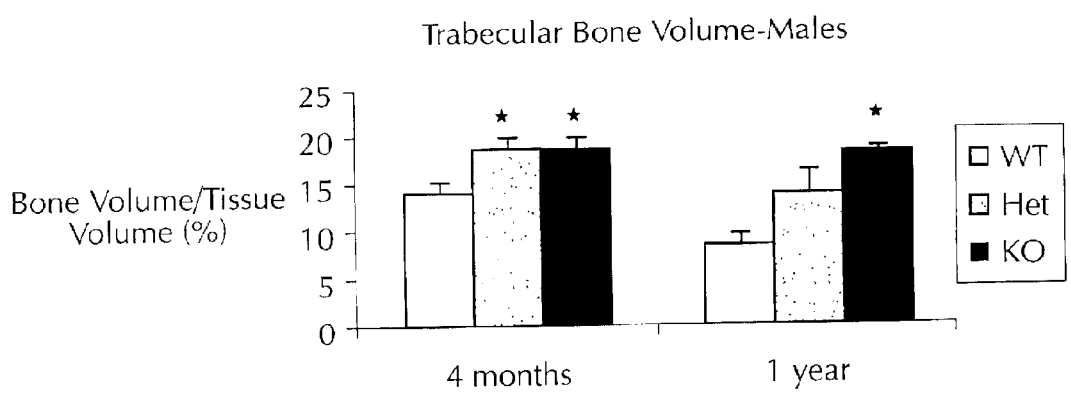
FIG. 16 is a chart showing the effects of osteoregulin gene disruption on bone phenotype on mice aged 4 months and 1 year, as determined by quantitative histomorphometry (*=p<0.05). Wild type (WT); heterozygote (Het); knockout (KO) (i.e., homozygote).
Figure 16B:
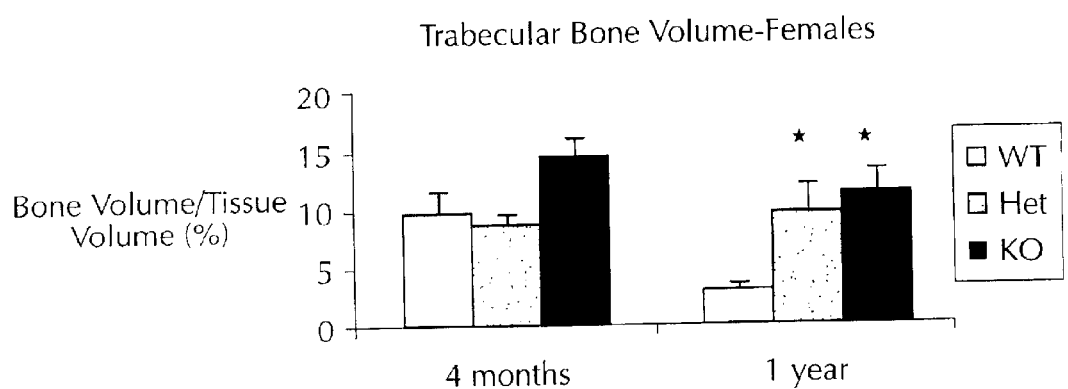
Figure 16C:
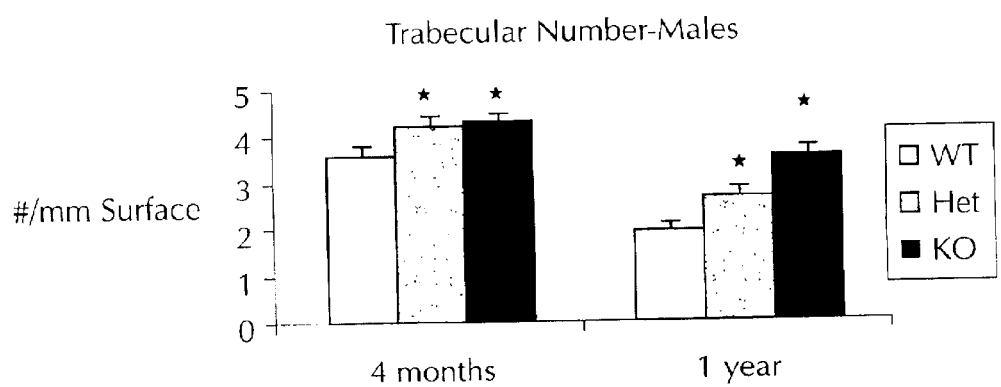
Figure 16D:
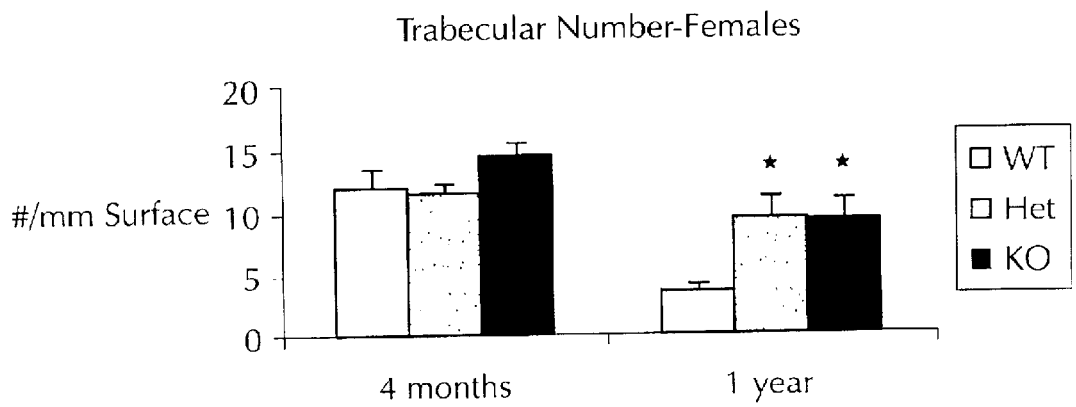
Figure 16E:
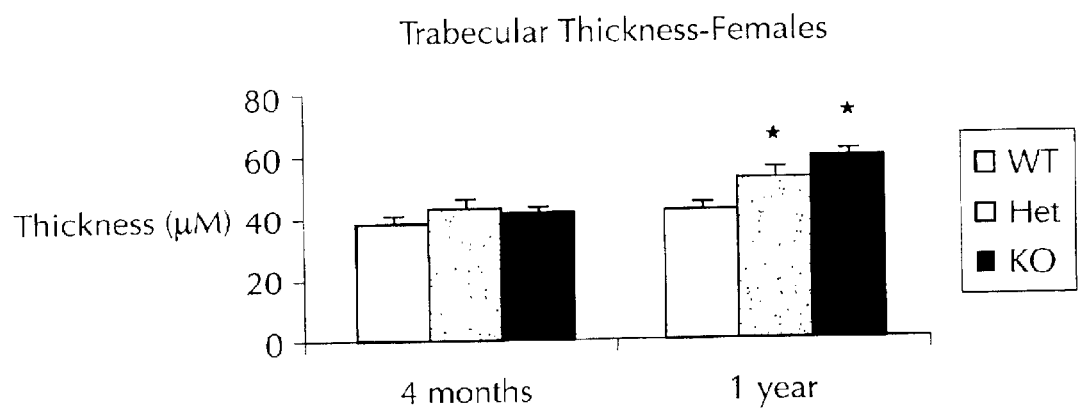
Figure 16F:
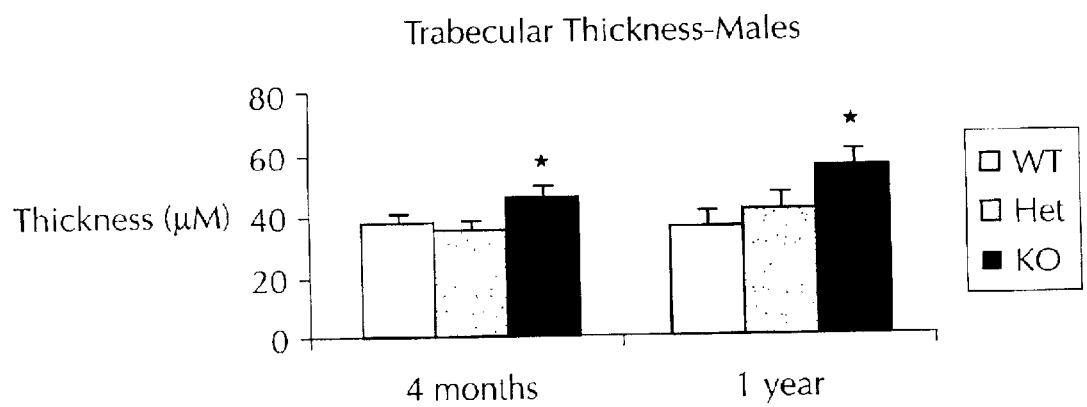

Heterozygote intercrosses produced litters with Mendelian ratios of wild type, heterozygous and homozygous mutant pups. Northern analysis of mRNA prepared from tibia of wild type, heterozygous and knockout animals revealed no osteoregulin message in knockout animals, and reduced expression in heterozygous animals. Southern analysis confirmed the disruption of the osteoregulin gene (FIG. 15). Immunohistochemistry of tibia sections revealed osteoregulin protein in osteocytes in wild type animals. These bone sections were negative for osteoregulin protein in homozygous mutant animals.

6. Phenotypic Analysis of Genetically-Modified Mice

Mice heterozygous and homozygous for the osteoregulin mutations appeared fertile and, in general, suffer from no obvious, severe pathology. In order to determine if osteoregulin mutation has an effect on the bone physiology of mice, we examined groups of at least twelve animals from each sex and genotype at four months and 1 year of age and analyzed bone parameters by DEXA, pQCT, and histomorphometry.

Animals were maintained on a 12-hr lightil 2-hr dark cycle and were provided food and water ad libitum. Ten and two days prior to sacrifice, mice were given subcutaneous injection of the fluorochrome calcein at 10 mg/kg (Sigma Chemical). On the day of sacrifice, animals were anesthetized and scanned by Dual Energy X-Ray Absorptiometry (DEXA). Animals were then euthanized by cervical dislocation and the hindlimbs removed and placed in 70% ethanol, for later peripheral Quatitative Computed Tomography (pQCT) and histomorphometric analysis as described below.

DEXA analysis involves the quantitation of an X-ray image of a live animal to estimate bone, fat, and lean mass. Animals were anesthetized and scanned for whole body bone area, mineral content and bone density measurements by DEXA (Hologic 4500, Hologic, Bedford, Mass.) equipped with rodent whole body scan software (Hagiwara et al., Bone & Mineral 22: 57–68, 1993). The scan field size was 15×8 cm, resolution was 0.0254×0.0127 cm and scan speed was 7.25 mm/sec.

The comparison of whole body bone area, bone mineral content, and bone mineral density in wild type versus heterozygous and homozygous (knockouts) mutant animals indicates that disruption of the osteoregulin gene leads to increased bone in heterozygous and homozygous mutant animals (Table 2). In female mice, there is an 11% increase in bone area in heterozygotes and 15% in homozygotes. The increase in bone mineral content is 14% and 18%, respectively. In males, there is also a significant increase in these parameters. An even more pronounced increase in trabecular bone was seen in heterozygote and knockout animals at one year of age.

In addition to examining bone parameters of osteoregulin knockout mice, we also used DEXA analysis to measure body fat. In female knockout and heterozygous animals, there were significant increases in total body weight, fat content, and percent body fat (Table 3). In addition, mesenteric, gonadal and kidney fat pads were removed and weighed independently (Table 4). Knockout and heterozygote females had significantly heavier white fat pads. These data may indicate a mild obesity phenotype associated with osteoregulin mutation in female mice.

TABLE 2

Dual X-ray absorptiometry (DEXA) analysis. *Difference between mutant and wild type is statistically significant ($p < 0.05$)

| Sex/ Genotype | Bone Area | | Bone Mineral Content | | Bone Mineral Density | |
| --- | --- | --- | --- | --- | --- | --- |
| | Mean | SD | Mean | SD | Mean | SD |
| Female | | | | | | |
| Wild type | 8.1106 | 1.283 | 0.6652 | 0.1041 | 0.0821 | 0.0032 |
| Heterozygote | 9.0227* | 1.0282 | 0.7556* | 0.0974 | 0.0836 | 0.0028 |
| Knockout | 9.3294* | 1.2293 | 0.7860* | 0.1183 | 0.0842 | 0.0041 |
| Male | | | | | | |
| Wild type | 9.7497 | .9368 | 0.7819 | 0.0846 | 0.0816 | 0.0033 |
| Heterozygote | 10.3789* | .8695 | 0.8397* | 0.0964 | 0.0808 | 0.0043 |
| Knockout | 10.0141 | 1.1489 | 0.8340 | 0.1019 | 0.0833* | 0.003 |

TABLE 3

Body Mass Parameters by Dual X-ray absorptiometry (DEXA) analysis. *Difference between mutant and wild type is statistically significant ($p < 0.05$)

| Sex/Genotype | Bone Mineral Content | | Fat Content | | Fat % | | Lean | | Total Weight (g) | |
| --- | --- | --- | --- | --- | --- | --- | --- | --- | --- | --- |
| | Mean | SD | Mean | SD | Mean | SD | Mean | SD | Mean | SD |
| Female | | | | | | | | | | |
| WildType | 0.6652 | 0.1041 | 3.308 | 1.723 | 11.7 | 5.23 | 22.6 | 3.38 | 26.5 | 4.84 |
| Heterozygote | 0.7556* | 0.0974 | 5.7* | 3.06 | 18.5* | 8.2 | 23.3 | 1.7 | 29.8* | 3.14 |
| Knockout | 0.7860* | 0.1183 | 5.87* | 3.29 | 18.7* | 8.7 | 23.4 | 2.4 | 30.1* | 4.27 |
| Male | | | | | | | | | | |
| Wild Type | 0.7819 | 0.0846 | 5.96 | 4.11 | 16.8 | 9.21 | 27.2 | 2.4 | 33.9 | 3.87 |
| Heterozygote | 0.8397* | 0.0964 | 6.73 | 3.05 | 17.81 | 7 | 29.6* | 2.8 | 37.2* | 3.36 |
| Knockout | 0.8340 | 0.1019 | 5.62 | 2.9 | 15.7 | 6.97 | 28.4 | 2.11 | 34.9 | 3.27 |

TABLE 4

Fat Pat Mass (in grams). *Difference between mutant and wild type is statistically significant ($p < 0.05$)

| Sex/Genotype | Mesenteric Fat Pad | | Gonadal Fat Pad | | Kidney Fat Pad | | Scapular Brown Fat | |
| --- | --- | --- | --- | --- | --- | --- | --- | --- |
| | Mean | SD | Mean | SD | Mean | SD | Mean | SD |
| Female | | | | | | | | |
| Wild Type | 0.28 | 0.12 | 0.2675 | 0.165 | 0.0992 | 0.0623 | 0.091 | 0.022 |
| Heterozygote | 0.41* | 0.13 | 0.473* | 0.215 | 0.17* | 0.074 | 0.100 | 0.018 |
| Knockout | 0.36 | 0.18 | 0.475* | 0.275 | 0.164* | 0.097 | 0.105 | 0.019 |
| Male | | | | | | | | |
| Wild Type | 0.295 | 0.122 | 0.287 | 0.207 | 0.0635 | 0.0578 | 0.086 | 0.0547 |
| Heterozygote | 0.279 | 0.101 | 0.326 | 0.163 | 0.0738 | 0.0541 | 0.086 | 0.035 |
| Knockout | 0.344 | 0.144 | 0.318 | 0.147 | 0.075 | 0.054 | 0.0836 | 0.0342 |

Higher resolution morphology of the proximal tibia of wild type, heterozygous, and knockout mice was measured in transverse plane by pQCT. Bone density was determined with a Stratec XCT 960 M (Norland Medical Systems, Fort Atkinson, Wis.) as described previously (Ballica et al., J. of Bone & Mineral Research 14: 1067–74, 1999). One millimeter thick slices located 3 mm proximal to the distal end of distal femoral metaphyses were scanned. Analysis was performed using XMICE version 5.1 software (Norland Medical Systems, Fort Atkinson, Wis.).

There was significant higher trabecular content and trabecular density in both male and female homozygous mutant mice compared to wild type. In addition, heterozygous males had significantly greater trabecular bone content and density. Male heterozygous and homozygous mice also demonstrated significantly increased cortical bone area, total bone content and total bone area compared to wild type (Table 5).

The effect of the osteoregulin gene disruption was more pronounced at 1 year, with 2-fold to 3fold more trabecular bone volume in male and female knockouts, respectively, as compared to wild types. The increased trabecular bone volume was reflective of both increased trabecular number and increased trabecular thickness (FIG. 16).

It was highly noteworthy that heterozygous animals exhibited the phenotypic effect of increased bone. It indicates that the loss of one allele and the resulting reduced gene expression caused significant phenotypic effects in bones. Of additional note, both the heterozygous and knockout mice apparently exhibited less aging associated bone loss than wild type animals. The male and female 1 year old groups possessed approximately 40% and 70%, respectively, less trabecular bone volume versus the matched 4 month old groups. By contrast, the knockout males exhibited no trabecular bone loss at 1 year; knockout female bone volume was reduced by only 15% in the 1 year

TABLE 5 pQCT analysis of proximal tibia. *Difference between mutant and wild type is statistically significant ($p < 0.05$).

| Sex/Genotype | Total Bone Content | | Total Bone Area | | Trabecular Content | | Trabecular Density | | Trabecular Area | |
|---|---|---|---|---|---|---|---|---|---|---|
| | Mean | SD | Mean | SD | Mean | SD | Mean | SD | Mean | SD |
| Female | | | | | | | | | | |
| Wild type | 1.817 | 0.26 | 3.27 | .32 | 0.3067 | 0.0711 | 176.1 | 35.3 | 1.737 | 0.15 |
| Heterozygote | 1.859 | 0.19 | 3.35 | .30 | 0.3380 | 0.0659 | 189.6 | 32.0 | 1.778 | 0.19 |
| Knockout | 1.883 | 0.29 | 3.47 | .42 | 0.3969 | 0.0782 | 211.6* | 35.3 | 1.881 | 0.24 |
| Male | | | | | | | | | | |
| Wild type | 1.559 | 0.21 | 3.88 | .46 | 0.2922 | 0.0669 | 216.8 | 28.04 | 1.338 | 0.18 |
| Heterozygote | 1.816* | 0.27 | 4.32* | .56 | 0.359* | 0.0717 | 242.1* | 29.8 | 1.477 | 0.20 |
| Knockout | 1.71* | 0.21 | 4.18* | .36 | 0.362* | 0.0636 | 251.3* | 30.9 | 1.437 | 0.15 |

To further characterize the increase in trabecular bone in osteoregulin mutant animals, trabecular morphology of bone sections was examined by bone histomorphometry as previously reported. (Simmons et al., J. of Pharmacology & Experimental Therapeutics 286: 341–4, 1998). Histomorphometric analysis of calcein double-labeled sections of the tibial metaphysis allows the measurement of bone composition at the cellular/microscopic level, and the calcein double label allows for the quantitation of bone growth within a two-week period. Following pOCT analysis, proximal tibiae were dehydrated and embedded in methyl methacrylate and 4 and 10 μm longitudinal sections prepared with a Reichert-Jung Polycut S microtome (Leica, Deerfield, Ill.). The 4 μm sections were stained with modified Masson's Trichrome stain and static histologic methaphyseal bone parameters were quantified using a computer-aided image analysis system (Bioquant II, M Biometrics, Nashville, Tenn.). Bone parameters, including trabecular bone volume, trabecular number and thickness, and osteoclast number were determined by standard procedures (Parfitt et al., J. of Bone & Mineral Research 2: 595–610, 1987). Percent labeled perimeter, mineral apposition and bone formation rates/bone volume were determined on unstained 10 μm sections via quantitation of calcein fluorochrome signal.

At 4 months of age, a 50% increase was observed in trabecular bone volume in female homozygotes compared to wild type (FIG. 16). In males, there is 32% greater trabecular bone volume in homozygotes. Male heterozygotes also demonstrated a significantly higher trabecular bone volume.

old mice (FIG. 16). Thus, the reduction in osteoregulin expression and, therefore, activity, protects against age-related bone loss.

The net increase in trabecular bone volume observed in the heterozygous and knockout animals could theoretically arise from either 1) decreased osteoclastic bone resorption, 2) increased osteoblast mediated bone formation or 3) a combination of osteoblast and osteoclast effects. Histomorphometric quantitation revealed no significant differences in osteoclast number or osteoclast surface. Dynamic histomorphometry measurements utilizing calcein double-labeled bones to quantitate the bone formation rate within a 10 day labeling interval demonstrated no difference in mineral apposition rate. A statistically significant increase in bone formation rate per bone volume referent was observed in both male and female mice at 1 year. However, when normalized to the greater amount of trabecular bone present in the mutant animals, there was no difference in bone formation rate per bone surface. Therefore, histomorphometric analysis did not indicate whether osteoregulin ablation increased bone through an osteoblast effect, an osteoclast effect or some combination.

7. Ex Vivo Culture

Figure 17A:
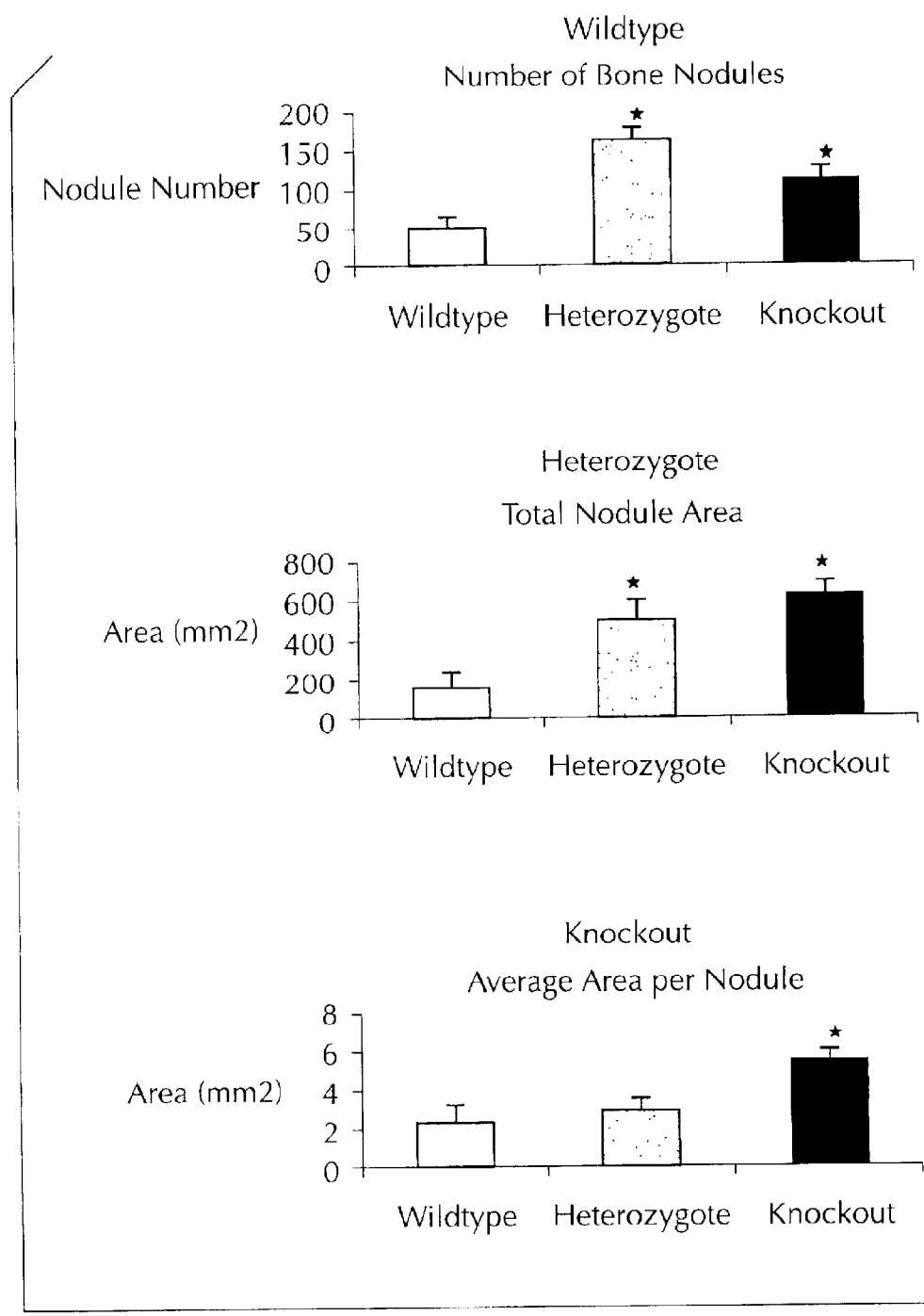
FIG. 17A is a graph quantitating mineralized nodules by Von Kossa staining of primary bone marrow cultures.
Figure 17B:
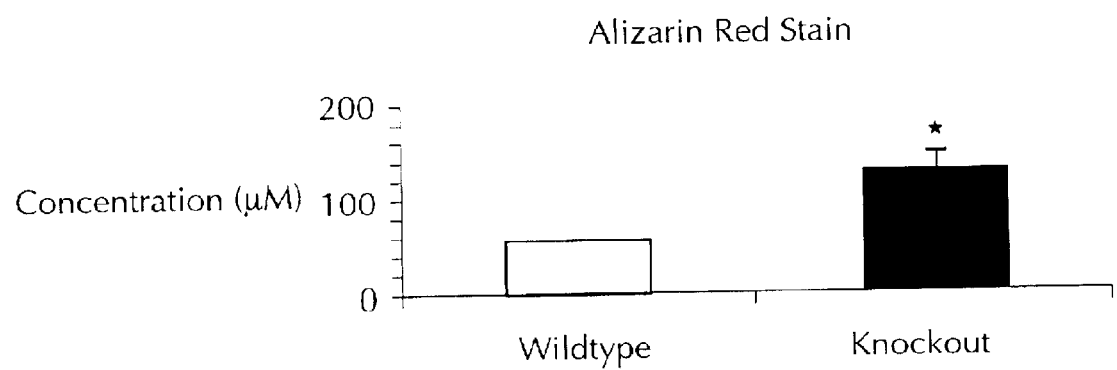
FIG. 17B is a graph depicting Alizarin Red staining of primary calvarial cultures.

In order to further examine the cellular mechanisms behind the increased trabecular bone volume in heterozygote and knockout animals, we examined the in vitro mineralization and osteoclastogenesis potential of cultures derived from wild type and mutant animals. Primary cultures of bone marrow cells from all three genotypes were grown in the presence of sodium ascorbate and β-glycerophosphate to induce osteoblast differentiation and promote bone nodule formation. After three weeks of growth, mineralization was detected by Von Kossa stain and quantitated by image analysis. Heterozygote- and knockout-derived cultures gave rise to significantly more bone nodules than those from wild type bone marrow, suggesting the presence of more osteoblastic precursor cells in the marrow analysis. In addition, the mineralized area per nodule was increased in knockout cultures (FIG. 17A). A second culture system derived from mouse calvarial bone of 3-day-old mice produced analogous results. In this more highly osteoblast enriched system, knockout calvarial cultures produced 60% more mineralized matrix as assayed by quantitation of solubilized Alizarin Red stain (FIG. 17B). In addition, this experiment indicated that the osteoblastic cells from knockout mice exhibited increased mineralization potential even at only 3 days after birth.

Figure 17C:
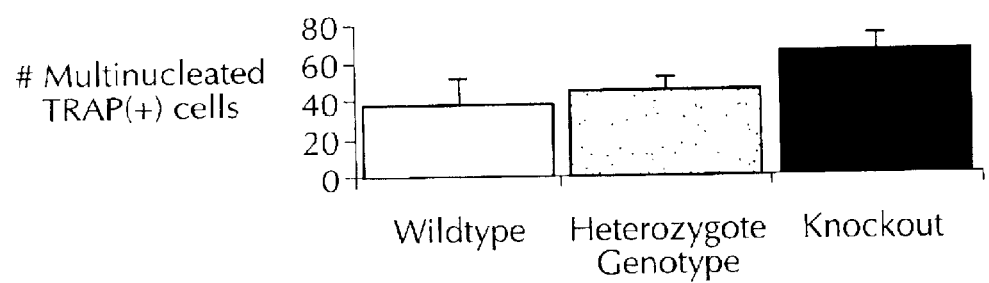
FIG. 17C is a graph quantitating osteoclastogenesis, as determined by tartrate resistant acid phosphatase (TRAP) cytochemical stain of bone marrow cultures. TRAP positive cells with three or more discrete nuclei were counted (*=p<0.05).

In order to determine if a deficiency in the formation or activity of osteoclasts contributed to the increased bone phenotype, bone marrow cultures from wild type, heterozygous and knockout animals were established under osteoclast promoting conditions. The ability of marrow cultures to form multinucleated tartrate-resistent alkaline phosphatase (TRAP) positive cells was unimpaired (FIG. 17C). In fact, knockout and heterozygote bone marrow cultures exhibited a trend toward higher numbers of TRAP positive multinudeated cells than wild type derived cultures.

No differences were seen in mineral apposition rate or bone formation rate during the two-week labeling period. This may indicate that the events leading to the increased bone volume in the mutant animals preceded the labeling period.

8. Statistical Methods

Statistical significance of in vivo parameters was determined by two-tailed student's t-test.

Human Osteoregulin

1. Isolation

Figure 18:
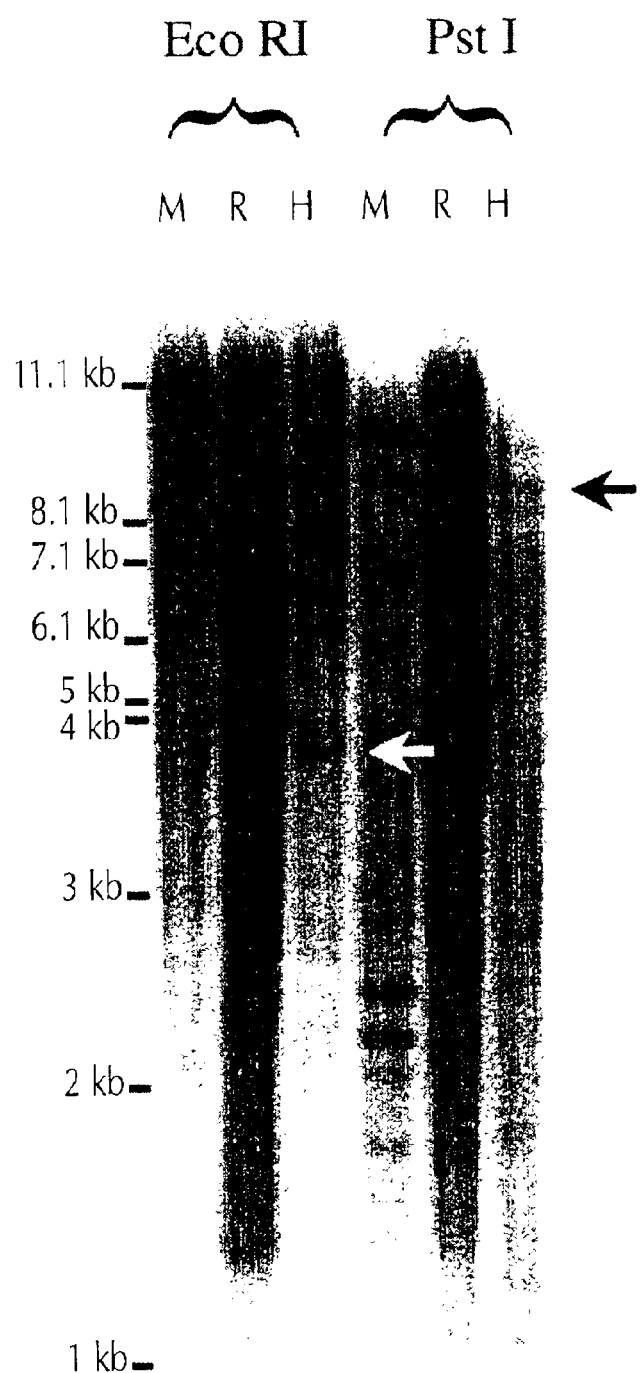
FIG. 18 is a Southern blot indicating hybridization of a rat osteoregulin probe to human genomic DNA. Mouse (M); Rat (R); Human (H).

We have identified two splice variants of human osteoregulin. The nucleic acid and amino acid sequences of one variant are shown in FIG. 3A (SEQ ID NO: 5) and FIG. 3B (SEQ ID NO: 6), respectively. The nucleic acid and amino acid sequences of the second human splice variant are shown in FIG. 4A (SEQ ID NO: 7) and 4B (SEQ ID NO: 8), respectively. These two polypeptide variants lacking an N-terminal signal sequence are shown in FIG. 21A (SEQ ID NO: 34) and in FIG. 21B (SEQ ID NO: 46) and are encoded by the nucleic acid sequences of SEQ ID NO: 33 and 45, respectively. The initial steps in identifying the human osteoregulins involved hybridizing a rat cDNA probe of SEQ ID NO: 1 to human genomic DNA. This rat CDNA probe was $^{32}$P-CTP labeled (Prime-It® II Random Primer Labeling Kit, Cat. No. 300385, Stratagene, La Jolla, Calif.). Human, rat, and mouse genomic DNAs (10µg) (Cat Nos. 6550-1, 6750-1, and 6650-1, respectively, Clontech, Palo Alto, Calif.) were digested with either EcoR1 or PST1 restriction enzymes (New England Biolabs, Beverly, Mass.) overnight at 37° C. The samples of digested DNA were then separated by electrophoresis on a 0.8% agarose/1% TAE gel overnight at 35 V. The gel was denatured by two 30 min washes in "Solution A" (1.5 M NaCl, 500 mM NaOH) and then neutralized in "Solution B" (1M ammonium acetate, 200 mM NaOH). The DNA in the gel was then transferred to a Hybond N nylon membrane (Cat. No. RPN303N, Amersham Pharmacia Biotech, Buckhamshire, England) by capillary transfer using Solution B overnight. The DNA was then crosslinked to the membrane using a Stratalinker ("Autocrosslink" setting, Stratagene). Hybridization was performed in 10 ml of a standard solution (Quickhybe® solution, Cat. No. 201221, Stratagene) in roller bottles at 60° C. for one hour. The membrane was wrapped in plastic wrap and exposed to X-ray film for two days. The film revealed a single human gene that hybridized to the rat probe (FIG. 18).

Figure 19:
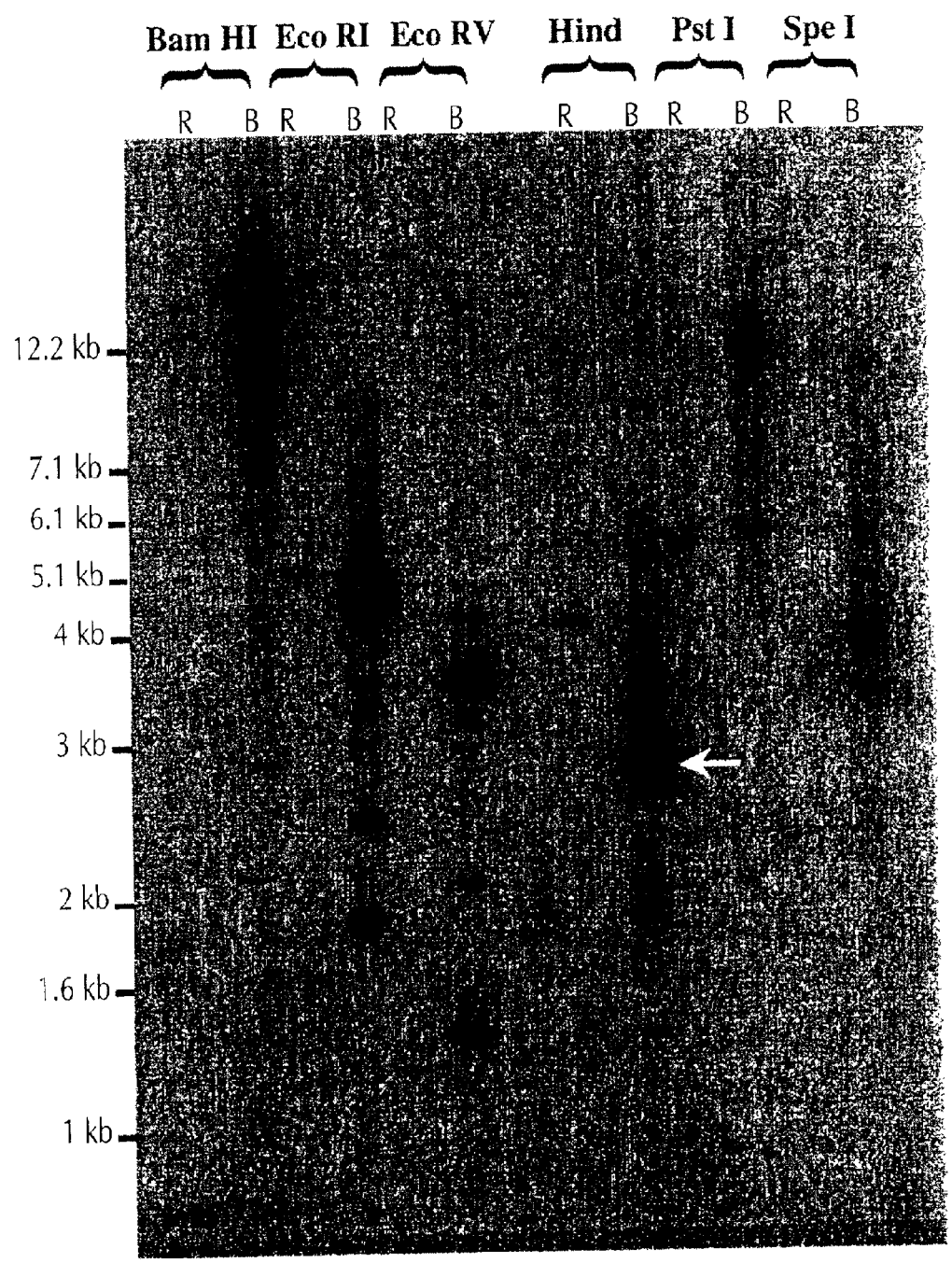
FIG. 19 shows Southern blot hybridization of rat cDNA to human BAC clone 33735(B).

A human genomic BAC library was then screened (Genome Systems, Inc., Palo Alto, Calif.) using the rat osteoregulin CDNA probe. BAC clone DNA (2.5 µg) and rat genomic DNA (10 µg) samples were digested with Bam HI, Eco RI, Eco RV, Hind III, Pst I, and Spe I, and the samples were then subjected to electrophoresis and probe hybridization as described above. The hybridization results are shown in FIG. 19. The hybridizing fragment of the Hind III human BAC clone library was the same size as the hybridizing fragment in the human genomic DNA sample.

Figure 20:
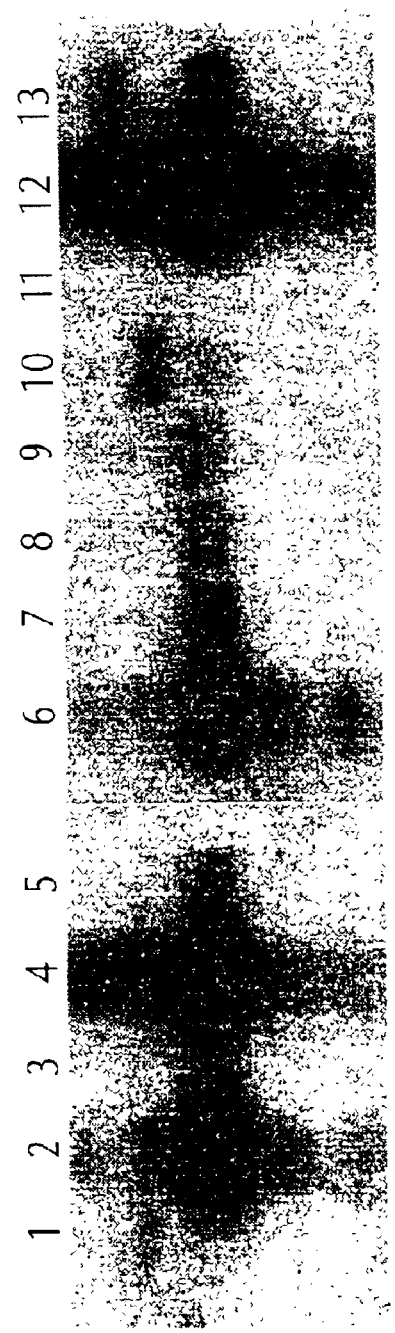
FIG. 20 is a Southern blot detailing the subcloning of hybridizing HindIII fragment from human BAC clone 22725. Clones 2, 4, 6, and 12 were considered to have the insert of interest and were subjected to sequence analysis.

The Hind III fragment of the BAC clone 22725 was electrophoresed using a 1.5% Low Melt Agarose/TAE gel, and fragments between 2–3 kb were isolated by LiCl purification. The insert DNA was cloned into pBluescript (Cat No. 212205, Stratagene), digested with Hind III and phosphatase treated. Following overnight T4 DNA ligase treatment (Clontech), 1 µl of ligation reaction sample was used to transform Dh5-alpha competent E. coli cells (Gibco BRL). Tranformed colonies were white and AMP-resistant. These colonies were selected, cultured in 5 ml overnight, and DNA from these cells was purified (Qiagen Robot® miniprep, Qiagen, Valencia, Calif.). Clones were then Hind III digested, electrophoresed in 1% agarose/TAE gel, transferred to nylon and hybridized to the full length rat cDNA probe as previously described. The results of this hybridization are shown in FIG. 20. Clones 2, 4, 6, and 12 were selected for subsequent sequence analysis (Genome Systems, Inc.), which revealed the osteoregulin cDNA fragment of SEQ ID NO:33 (FIG. 21A) encoding an osteoregulin polypeptide of SEQ ID NO: 34 (FIG. 21B, identical to amino acids 38–526 of SEQ ID NO: 6) which lacks the secretory signal sequence.

Determinations of the full length human osteoregulin sequences of SEQ ID NOs 5 and 7 were achieved by electronic analysis of a Celera database by conducting a BLAST search using the human sequence of the BAC done (SEQ ID NO: 9). The identified human sequence (Celera clone Contig|41787504) was compared to the mouse osteoregulin sequence (SEQ ID NO: 3) using a Genewise program. This comparison confirmed that the identified genomic sequence encoded the same human sequence as the BAC clone and also contained additional upstream coding exons.

Alignment of the reverse complement of the Celera genomic sequence with the mouse osteoregulin cDNA sequence (SEQ ID NO: 3) using the MEGALIGN™ program (DNASTAR, Inc., Madison, Wis.) revealed homology in the 5' untranslated region of the sequences. Based upon sequence alignment between the mouse cDNA sequence and the human genomic sequence, PCR primers were designed to amplify the 5' end of the human cDNA sequence. 3' primers were designed based on the 3' terminal exon of the BAC clone. Total RNA from human osteoblast SaOS cells was reverse transcribed using SuperScript® according to manufacturer's recommended protocol (Gibco BRL, Gaithersburg, Md.). High fidelity first round PCR (Boehringer Mannheim) was performed with primer pair CAAACTTTAATTTCAGCAAA (SEQ ID NO: 35)/GCGCCATATTCTTCTTGGTC (SEQ ID NO: 36). First round PCR product (0.001 µl) was used as a template for second round PCR using primer pair CTTTAAATTTCAG-CAAAATGCCC (SEQ ID NO: 37)/CATCCTCAGGCCATTGTGAG (SEQ ID NO: 38). The resultant 433 bp product was subcloned into a TA cloning vector (Clontech) and then sequenced. The sequence was found to overlap from exon 4, allowing compilation of complete sequences (SEQ ID NOs 5 and 7). The coding region of the sequence was confirmed by PCR amplification using primer pair GCCATGCGAGTTTCTGTGTGGG (SEQ ID NO: 39)/TGGTGGACTAGTCACCATCG (SEQ ID NO: 40). Sequence analysis revealed the two splice variants cDNAs (SEQ ID NOs: 5 and 7) and the two polypeptides encoded by these nucleic acid sequences (SEQ ID NOs: 6 and 8) as shown in FIGS. 3A–3B and 4A–4B. The hydrophobic leader sequence for the osteoregulin polypeptides shown in SEQ ID NOs: 6 and 8 lack amino acids 1–37. The amino acid sequences for the osteoregulin polypeptides lacking these leader sequences are shown in SEQ ID NO: 34 and SEQ ID NO: 46 (encoded by SEQ ID NO: 33 and SEQ ID NO: 45, respectively.

2. Characterization

The human osteoregulin sequence of SEQ ID NO: 6 was aligned to rat and mouse sequences using MegAlign (DNASTAR) using either Clustal or One pair analysis. The sequences were then analyzed manually as shown in FIG. 5. By Clustal analysis, the human SEQ ID NO: 6 was 44.6% identical to mouse and 44.7% identical to rat. Homology was conserved throughout the length of the polypeptides. As with rat and mouse, the RGD motif and the serine-rich tails were conserved in human osteoregulin.

The genomic structure of the human osteoregulin gene is shown in Table 6.

TABLE 6

Genomic Structure of Human Osteoregulin

| | base pairs | Celera Clone position | hOR cDNA position | amino acid position |
|---|---|---|---|---|
| Exon 1: | 82 | 7760–7842 | 1–83 | |
| Intron 1: | 1689 | | | |
| Exon 2: | 65 | 9531–9596 | 84–149 | 1–18 |
| Intron 2: | 3866 | | | |
| Exon 3: | 53 | 13462–13515 | 150–203 | 19–37 |
| Intron 3: | 6291 | | | |
| Exon 4: | 1815 | 19807–21622 | 204–2019 | 38–526 |
| Exon 3A* | 93 | 14514–14607 | | 38–68 |

*Additional splice variant exon 3A can be included between exons 3 and 4, creating a polypeptide of 557 amino acids.

Chromosomal localization of the human osteoregulin gene was determined by FISH analysis of BAC clone 22725 (Genome Systems), demonstrating colocalization to 4q22.

Purified DNA from clone 22725 was labeled with digoxigenin dUTP by nick translation. Labeled probe was combined with sheared human DNA and hybridized to metaphase chromosomes derived from PHA stimulated peripheral blood lymphocytes in a solution containing 50% formamide, 10% dextran sulfate and 2×SSC. Specific hybridization signals were detected by incubating the hybridized slides in fluoresceinated antidigoxigenin antibodies followed by counterstaining with DAPI for one-color experiments. Probe detection for two color experiments was accomplished by incubating the slides in fluoresceinated antidigoxigenin antibodies as well as avidin Texas red followed by counterstaining with DAPI. The initial experiment resulted in the specific labeling of the long arm of a group B chromosome, which was believed to be chromosome 4 on the basis of size, morphology and banding pattern. A second experiment was conducted in which a biotin labeled probe, which is specific for the centromere of chromosome 4, was co-hybridized with clone 22725. This experiment resulted in the specific labeling of the centromere in red and the long arm in green of chromosome 4. Measurements of 10 specifically labeled chromosomes 4 demonstrated that clone 22725 is located at a position which is 28% of the distance from the centromere to the telomere of chromosome arm 4q, an area which corresponds to band 4q22 (Cytogenet. Cell Genet. 65:206–219, 1994). A total of 80 metaphase cells were analyzed with 73 exhibiting specific labeling.

3. Tissue Distribution

Northern blot analysis of expression revealed expression in brain, bone marrow, and placenta, as demonstrated in FIG. 22. Tissues that demonstrated no osteoregulin mRNA included prostate, testes, and ovary. Human MTN northern blots were obtained commercially (Cat. Nos. 7780-1, 7759-1, 7757-1, Clontech, Palo Alto, Calif.). Membranes were hybridized with Quikhybe® (Stratagene, La Jolla, Calif.) as described above for Southern blots using a probe to exon 4 of human osteoregulin amplified from SAOS cell line cDNA at 68° C. for one hour. Blots were washed with 2×SSC/0.1% SDS at room temerature and at 60° C., then exposed to film for one week.

Reverse transcription PCR and subsequent Southern analysis of PCR products revealed human osteoregulin expression in brain, the human bone cell line SaOS, placenta, adrenal gland, ovary, peripheral blood lymphocytes, bone marrow, and fetal brain, as shown in FIG. 23. 24 human tissues were screened for osteoregulin expression by rtPCR using cDNAs included in the Origene Rapid-Scan® Human CDNA panel (cat no. HSCA-101, Origene Technologies, Rockville, Md.) and cDNA prepared from the human SAOS bone cell line. Primers (5'-AGATGCTGTTGATGTCAGCC-3') (SEQ ID NO 41) and (5'-AAGACCACGAGAAGGAATGG-3') (SEQ ID NO: 42) were used to amplify a 115 bp product. 20 μl of PCR product was electrophoresed on a 1% agarose/TAE gel, transferred to membrane, and hybridized as described above with a probe generated by the same primer pair from the human SaOS bone cell line.

What is claimed is:

1. An isolated or purified polynucleotide comprising:
   (a) a nucleic acid sequence encoding a polypeptide of SEQ ID NO:8; or
   (b) the coding sequence shown in SEQ ID NO:7.

2. An isolated or purified polynucleotide having at least 95% identity to a nucleic acid sequence encoding a polypeptide SEQ ID NO: 8, wherein said polynucleotide encodes a polypeptide having osteoregulin activity.

3. A vector comprising a polynucleotide according to claim 1.

4. A vector comprising a polynucleotide according to claim 2.

5. A method for producing a heterologous polypeptide comprising the amino acid sequence of SEQ ID NO:8 or a heterologous polypeptide comprising the amino acid sequence encoded by a nucleic acid sequence having at least 95% identity to the entire length of the nucleic acid encoding SEQ ID NO: 8, wherein said polypeptide has osteoregulin activity, said method comprising:
   (a) culturing a cell under conditions suitable for expression of the polypeptide, wherein said cell comprises a polynucleotide that encodes the heterologous polypeptide and the polynucleotide is operably linked to a promoter sequence; and
   (b) recovering said polypeptide.

6. The method of claim 5, wherein said polynucleotide comprises SEQ ID NO:7.

* * * * *

SEQUENCE LISTING

<160> NUMBER OF SEQ ID NOS: 46

<210> SEQ ID NO 1
<211> LENGTH: 1655
<212> TYPE: DNA
<213> ORGANISM: Rattus norvegicus

<400> SEQUENCE: 1

```
tgctaaaccc gaagaagcca agcttccctg aaggtgaacg acaccagaga gccgtgtgac      60
gatgcaggct gtgtctgttg gactgttcct cttcagtatg acctgggcgg caccaaagct     120
gaatgaagat ggcagcagcg gcggtaacca aggcaacatc cacttagcat ctgtgaagcc     180
tgagcccatg gtgggtaaag aacagagggt tgggcgagat gctccccttc acctgcttga     240
ccagaacagg cagggtgcca ccctcctcag aaatatcact cagcctgtaa agagtctggt     300
gacgggggact gaagtacaga gcgacagaaa caaagagaag aaacctcaga gtgttctaag     360
cgtaattcca acagatgtcc acaatactaa cgactactca gaagatacag agaaccaaca     420
gagggatcta ctactccaga acagcccagg acaaagcaaa cacacccctc gggcccgacg     480
aagcacgcac tacctaacac atctccccca aatcagaaag attctcagtg acttcgagga     540
cagtgcttcc ccagaccttc tagtgagggg ggataatgat gtccctcctt tcagtggaga     600
tggacaacat tttatgcaca ctcccgacag aggaggtgct gttggatctg atcctgaaag     660
ctcagctggt caccctgtgt caggctccag caatgtcgag attgttgacc cacacacgaa     720
tggactgggc tctaatgaga tcccaggag agaaggtcac ataggcggtg cctatgcaac     780
cagaggaaaa actgcgcagg gggcaggttc cgcggatgtg agccttgtgg agggcagcaa     840
tgaaatcacg ggcagtacca aatttaggga gctccctgga aaagaaggaa acagagtcga     900
tgccagcagc caaaatgctc atcaaggaaa agtagaattt cactacccac aagcgccctc     960
aaaagagaag gtaaaagggg gcagcaggga gcacacaggg aaagccggtt acaatgaaat    1020
ccccaagagc agcaagggcg cgctagcaa ggatgcggaa gaatctaaag ggaaccaagt    1080
aaccttgact gaaagccaaa ggttcccagg caaaggcaaa ggccagtctt ctcacagtct    1140
tggtaatgag gttaaaagtg aagaagactc ttctaatagt ctcagtagag aggggattgc    1200
aatagcacac aggagaacaa gccaccctac acggaatagg gggatgtcac agcggagagg    1260
ctcctgggcc tcgagaagac cccatcccca ccggcgcgta agcacccgcc aaagagacag    1320
tagtgagtca tcatccagtg ggagttctag cgagagcagt ggtgactaga ccccgggggtt   1380
gaaccagttc ccagctctgg tcctggagaa agagaggacg cagcagggac tgagcaaggt    1440
accagacttg gtcacctcca ggacactgtg ctgttttagt ggttgtaata agaatcccta    1500
ctcaaagttc taatgctttc tgaataaaaa ctttcgtaag aatttatata ataggtaata    1560
tttgactagg cggcccatta aatagtctg tggatgtcac aggtgccttg atatgtgatt    1620
tgctcttcag acatgaaaat aaagaggctt tctct                              1655
```

<210> SEQ ID NO 2
<211> LENGTH: 435
<212> TYPE: PRT
<213> ORGANISM: Rattus norvegicus

<400> SEQUENCE: 2

```
Met Gln Ala Val Ser Val Gly Leu Phe Leu Phe Ser Met Thr Trp Ala
  1               5                  10                  15

Ala Pro Lys Leu Asn Glu Asp Gly Ser Ser Gly Gly Asn Gln Gly Asn
             20                  25                  30

Ile His Leu Ala Ser Val Lys Pro Glu Pro Met Val Gly Lys Gly Thr
         35                  40                  45

Glu Gly Gly Arg Asp Ala Pro Leu His Leu Leu Asp Gln Asn Arg Gln
     50                  55                  60
```

-continued

```
Gly Ala Thr Leu Leu Arg Asn Ile Thr Gln Pro Val Lys Ser Leu Val
 65                  70                  75                  80

Thr Gly Thr Glu Val Gln Ser Asp Arg Asn Lys Glu Lys Lys Pro Gln
                 85                  90                  95

Ser Val Leu Ser Val Ile Pro Thr Asp Val His Asn Thr Asn Asp Tyr
            100                 105                 110

Ser Glu Asp Thr Glu Asn Gln Gln Arg Asp Leu Leu Leu Gln Asn Ser
        115                 120                 125

Pro Gly Gln Ser Lys His Thr Pro Arg Ala Arg Arg Ser Thr His Tyr
    130                 135                 140

Leu Thr His Leu Pro Gln Ile Arg Lys Ile Leu Ser Asp Phe Glu Asp
145                 150                 155                 160

Ser Ala Ser Pro Asp Leu Leu Val Arg Gly Asp Asn Asp Val Pro Pro
                165                 170                 175

Phe Ser Gly Asp Gly Gln His Phe Met His Thr Pro Asp Arg Gly Gly
            180                 185                 190

Ala Val Gly Ser Asp Pro Glu Ser Ser Ala Gly His Pro Val Ser Gly
        195                 200                 205

Ser Ser Asn Val Glu Ile Val Asp Pro His Thr Asn Gly Leu Gly Ser
    210                 215                 220

Asn Glu Ile Pro Gly Arg Glu His Ile Gly Gly Ala Tyr Ala Thr
225                 230                 235                 240

Arg Gly Lys Thr Ala Gln Gly Ala Gly Ser Ala Asp Val Ser Leu Val
                245                 250                 255

Glu Gly Ser Asn Glu Ile Thr Gly Ser Thr Lys Phe Arg Glu Leu Pro
            260                 265                 270

Gly Lys Glu Gly Asn Arg Val Asp Ala Ser Ser Gln Asn Ala His Gln
        275                 280                 285

Gly Lys Val Glu Phe His Tyr Pro Gln Ala Pro Ser Lys Glu Lys Val
    290                 295                 300

Lys Gly Gly Ser Arg Glu His Thr Gly Lys Ala Gly Tyr Asn Glu Ile
305                 310                 315                 320

Pro Lys Ser Ser Lys Gly Gly Ala Ser Lys Asp Ala Glu Glu Ser Lys
                325                 330                 335

Gly Asn Gln Val Thr Leu Thr Glu Ser Gln Arg Phe Pro Gly Lys Gly
            340                 345                 350

Lys Gly Gln Ser Ser His Ser Leu Gly Asn Glu Val Lys Ser Glu Glu
        355                 360                 365

Asp Ser Ser Asn Ser Leu Ser Arg Glu Gly Ile Ala Ile Ala His Arg
    370                 375                 380

Arg Thr Ser His Pro Thr Arg Asn Arg Gly Met Ser Gln Arg Arg Gly
385                 390                 395                 400

Ser Trp Ala Ser Arg Arg Pro His Pro His Arg Arg Val Ser Thr Arg
                405                 410                 415

Gln Arg Asp Ser Ser Glu Ser Ser Ser Gly Ser Ser Ser Glu Ser
            420                 425                 430

Ser Gly Asp
        435

<210> SEQ ID NO 3
<211> LENGTH: 1682
<212> TYPE: DNA
<213> ORGANISM: Mus musculus
```

```
<400> SEQUENCE: 3
caaactttaa atttcagcaa atgcccagag actaagcccg aagaagccaa gctttcctga      60
aggtgaatga cgccagaggg cctcatgaag atgcaggctg tgtctgttgg actgctcctc     120
ttcagtatga cctgggcggc accaatgccg aatgaagaca ggagcagctg cggcaatcaa     180
gacagcattc acaaggactt ggcagcatct gtgtatcctg atcccacggt ggatgaaggc     240
acagaggatg ggcaaggtgc tctccttcac ccgcctggcc aggacaggta tggtgctgcc     300
ctcctcagaa atatcacgca gcctgtaaag agtctagtga ctggggccga actacggagg     360
gaaggaaacc aggagaagag acctcagagt gttctaagcg taattccagc agatgtcaat     420
gatgctaaag tctccttaaa agacataaag aatcaagaga gttatctgct aacccagagc     480
agcccggtca aaagcaaaca caccaaacac acccgccaga cccgacggag cactcactac     540
ctgacacatc tcccacagat caagaagact cccagtgacc ttgaaggcag tggctcccca     600
gatcttctag tgaggggaga taatgatgtc ccccctttca gtggagatgg gcaacatttt     660
atgcacattc ctggcaaagg aggtgctggg tctggtcctg aaagctcaac tagtcgcccc     720
ctctcaggct ccagcaaagc tgaagttatt gacccacata tgagtggact aggctctaat     780
gagatcccgg ggagagaagg acatggtggc agtgcctatg caaccagaga caaagctgca     840
caggggcag gctctgcagg tgggagcctt gtgggggca gcaatgaaat cacaggcagc      900
accaatttca gggaactccc cggaaaagaa ggaaacagaa ttaatgccgg cagccaaaat     960
gctcatcaag ggaaagtaga atttcactat ccacaagtgg cctcgagaga aaaggtaaag    1020
gggggcgtgg agcatgcagg gagagctggt tacaacgaaa tccccaagag cagcaaaggt    1080
agctctagca aagatgcaga agagtccaaa gggaaccaat taaccttgac tgcaagccaa    1140
agatttccag gtaaaggcaa aagccagggc cctgctctgc cctctcacag tcttagtaat    1200
gaggttaaaa gtgaagaaaa ccattatgtg ttccatggac aaaataatct atacccgaat    1260
aaagggatgt cacagcggag aggctcctgg ccttcgagaa gacccaattc ccacaggcgc    1320
gctagcaccc gccaaagaga cagcagcgag tcgtcatcca gtgggagttc tagtgagagt    1380
catggtgact agtccctggg attgaaccag tcccctgctc tagtcctgga ggaagagagg    1440
gcacagcagg aactgagcaa gccaacagac ctggtcccct ccaggacatt gtgctatttt    1500
aatggtggtt ataagaattt ctactcaaag ttctaatgct tttttcaata aaaactttca    1560
taagaatttg tataataggt aatatttgga caggcgacac attaaaatag tctgtgaatg    1620
tcacaagtgc cttgatacgt catcatttgc tcttcagaca tgaaaataaa tatgcttgct    1680
ct                                                                   1682

<210> SEQ ID NO 4
<211> LENGTH: 441
<212> TYPE: PRT
<213> ORGANISM: Mus musculus

<400> SEQUENCE: 4

Met Thr Pro Glu Gly Leu Met Lys Met Gln Ala Val Ser Val Gly Leu
  1               5                  10                  15

Leu Leu Phe Ser Met Thr Trp Ala Ala Pro Met Pro Asn Glu Asp Arg
             20                  25                  30

Ser Ser Cys Gly Asn Gln Asp Ser Ile His Lys Asp Leu Ala Ala Ser
         35                  40                  45

Val Tyr Pro Asp Pro Thr Val Asp Glu Gly Thr Glu Asp Gly Gln Gly
     50                  55                  60
```

```
Ala Leu Leu His Pro Pro Gly Gln Asp Arg Tyr Gly Ala Ala Leu Leu
 65                  70                  75                  80

Arg Asn Ile Thr Gln Pro Val Lys Ser Leu Val Thr Gly Ala Glu Leu
                 85                  90                  95

Arg Arg Glu Gly Asn Gln Glu Lys Arg Pro Gln Ser Val Leu Ser Val
            100                 105                 110

Ile Pro Ala Asp Val Asn Asp Ala Lys Val Ser Leu Lys Asp Ile Lys
            115                 120                 125

Asn Gln Glu Ser Tyr Leu Leu Thr Gln Ser Ser Pro Val Lys Ser Lys
130                 135                 140

His Thr Lys His Thr Arg Gln Thr Arg Arg Ser Thr His Tyr Leu Thr
145                 150                 155                 160

His Leu Pro Gln Ile Lys Lys Thr Pro Ser Asp Leu Glu Gly Ser Gly
                165                 170                 175

Ser Pro Asp Leu Leu Val Arg Gly Asp Asn Asp Val Pro Pro Phe Ser
            180                 185                 190

Gly Asp Gly Gln His Phe Met His Ile Pro Gly Lys Gly Gly Ala Gly
            195                 200                 205

Ser Gly Pro Glu Ser Ser Thr Ser Arg Pro Leu Ser Gly Ser Ser Lys
210                 215                 220

Ala Glu Val Ile Asp Pro His Met Ser Gly Leu Gly Ser Asn Glu Ile
225                 230                 235                 240

Pro Gly Arg Glu Gly His Gly Gly Ser Ala Tyr Ala Thr Arg Asp Lys
                245                 250                 255

Ala Ala Gln Gly Ala Gly Ser Ala Gly Gly Ser Leu Val Gly Gly Ser
            260                 265                 270

Asn Glu Ile Thr Gly Ser Thr Asn Phe Arg Glu Leu Pro Gly Lys Glu
            275                 280                 285

Gly Asn Arg Ile Asn Ala Gly Ser Gln Asn Ala His Gln Gly Lys Val
290                 295                 300

Glu Phe His Tyr Pro Gln Val Ala Ser Arg Glu Lys Val Lys Gly Gly
305                 310                 315                 320

Val Glu His Ala Gly Arg Ala Gly Tyr Asn Glu Ile Pro Lys Ser Ser
                325                 330                 335

Lys Gly Ser Ser Ser Lys Asp Ala Glu Glu Ser Lys Gly Asn Gln Leu
            340                 345                 350

Thr Leu Thr Ala Ser Gln Arg Phe Pro Gly Lys Gly Lys Ser Gln Gly
            355                 360                 365

Pro Ala Leu Pro Ser His Ser Leu Ser Asn Glu Val Lys Ser Glu Glu
370                 375                 380

Asn His Tyr Val Phe His Gly Gln Asn Asn Leu Thr Pro Asn Lys Gly
385                 390                 395                 400

Met Ser Gln Arg Arg Gly Ser Trp Pro Ser Arg Arg Pro Asn Ser His
                405                 410                 415

Arg Arg Ala Ser Thr Arg Gln Arg Asp Ser Ser Glu Ser Ser Ser Ser
            420                 425                 430

Gly Ser Ser Ser Glu Ser His Gly Asp
            435                 440

<210> SEQ ID NO 5
<211> LENGTH: 2019
<212> TYPE: DNA
<213> ORGANISM: Homo sapiens
```

<400> SEQUENCE: 5

```
caaactttaa atttcagcaa aatgcccaga gacttctaat cctgcaacaa gaagccaggt        60
attctgaagg tgaaagatac cagagattct caaagatgcg agttttctgt gtgggactac       120
tccttttcag tgtgacctgg gcagcaccaa catttcaacc acagactgag aaaactaagc       180
aaagctgtgt ggaagagcag aggcaggaag aaaaaaacaa agacaatatt ggttttcacc       240
atttgggcaa gagaataaat caagagctat catctaaaga aaatattgtc caggaaagaa       300
agaaagattt gtccctttct gaagccagtg agaataaggg aagtagtaaa tctcaaaatt       360
atttcacaaa tagacagaga ctgaataaag aatatagtat cagtaacaaa gagaatactc       420
acaatggcct gaggatgtca atttatccta agtcaactgg gaataaaggg tttgaggatg       480
gagatgatgc tatcagcaaa ctacatgacc aagaagaata tggcgcagct ctcatcagaa       540
ataacatgca acatataatg gggccagtga ctgcgattaa actcctgggg gaagaaaaca       600
aagagaacac acctaggaat gttctaaaca taatcccagc aagtatgaat tatgctaaag       660
cacactcgaa ggataaaaag aagcctcaaa gagattccca agcccagaaa agtccagtaa       720
aaagcaaaag cacccatcgt attcaacaca acattgacta cctaaaacat ctctcaaaag       780
tcaaaaaaat ccccagtgat tttgaaggca gcggttatac agatcttcaa gagagagggg       840
acaatgatat atctcctttc agtggggacg gccaaccttt taaggacatt cctggtaaag       900
gagaagctac tggtcctgac ctagaaggca agatattca aacagggttt gcaggcccaa       960
gtgaagctga gagtactcat cttgacacaa aaaagccagg ttataatgag atcccagaga      1020
gagaagaaaa tggtggaaat accattggaa ctagggatga aactgcgaaa gaggcagatg      1080
ctgttgatgt cagccttgta gagggcagca acgatatcat gggtagtacc aatttttaagg     1140
agctccctgg aagagaagga aacagagtgg atgctggcag ccaaaatgct caccaaggga      1200
aggttgagtt tcattaccct cctgcaccct caaaagagaa aagaaaagaa ggcagtagtg      1260
atgcagctga agtaccaac tataatgaaa ttcctaaaaa tggcaaaggc agtaccagaa       1320
agggtgtaga tcattctaat aggaaccaag caaccttaaa tgaaaaacaa aggtttccta      1380
gtaagggcaa aagtcagggc ctgcccattc cttctcgtgg tcttgataat gaaatcaaaa      1440
acgaaatgga ttcctttaat ggccccagtc atgagaatat aataacacat ggcagaaaat      1500
atcattatgt accccacaga caaaataatt ctacacggaa taagggtatg ccacaaggga      1560
aaggctcctg gggtagacaa ccccattcca acaggaggtt tagttcccgt agaagggatg      1620
acagtagtga gtcatctgac agtggcagtt caagtgagag cgatggtgac tagtccacca      1680
ggagttccca gcggggtgac agtctgaaga cctcgtcacc tgtgagttga tgtagaggag      1740
agccacctga cagctgacca ggtgaagaga ggatagagtg aagaactgag tgagccaaga      1800
atcctggtct ccttggggga attttttgcta tcttaatagt cacagtataa aattctatta     1860
aaggctataa tgttttttaag caaaaaaaaa tcattacaga tctatgaaat aggtaacatt      1920
tgagtaggtg tcatttaaaa atagttggtg aatgtcacaa atgccttcta tgttgtttgc      1980
tctgtagaca tgaaaataaa caatatctct cgatgataa                              2019
```

<210> SEQ ID NO 6
<211> LENGTH: 525
<212> TYPE: PRT
<213> ORGANISM: Homo sapiens

<400> SEQUENCE: 6

| | | | | | | | | | | | | | | |
|---|---|---|---|---|---|---|---|---|---|---|---|---|---|---|
|Met|Arg|Val|Phe|Cys|Val|Gly|Leu|Leu|Leu|Phe|Ser|Val|Thr|Trp|Ala|
|1| | | |5| | | | |10| | | | |15| |

Ala Pro Thr Phe Gln Pro Gln Thr Glu Lys Thr Lys Gln Ser Cys Val
     20      25      30

Glu Glu Gln Arg Gln Glu Lys Asn Lys Asp Asn Ile Gly Phe His
    35      40      45

His Leu Gly Lys Arg Ile Asn Gln Glu Leu Ser Ser Lys Glu Asn Ile
   50      55      60

Val Gln Glu Arg Lys Lys Asp Leu Ser Leu Ser Glu Ala Ser Glu Asn
65      70      75      80

Lys Gly Ser Ser Lys Ser Gln Asn Tyr Phe Thr Asn Arg Gln Arg Leu
    85      90      95

Asn Lys Glu Tyr Ser Ile Ser Asn Lys Glu Asn Thr His Asn Gly Leu
    100     105     110

Arg Met Ser Ile Tyr Pro Lys Ser Thr Gly Asn Lys Gly Phe Glu Asp
   115     120     125

Gly Asp Asp Ala Ile Ser Lys Leu His Asp Gln Glu Glu Tyr Gly Ala
130     135     140

Ala Leu Ile Arg Asn Asn Met Gln His Ile Met Gly Pro Val Thr Ala
145     150     155     160

Ile Lys Leu Leu Gly Glu Glu Asn Lys Glu Asn Thr Pro Arg Asn Val
    165     170     175

Leu Asn Ile Ile Pro Ala Ser Met Asn Tyr Ala Lys Ala His Ser Lys
   180     185     190

Asp Lys Lys Lys Pro Gln Arg Asp Ser Gln Ala Gln Lys Ser Pro Val
   195     200     205

Lys Ser Lys Ser Thr His Arg Ile Gln His Asn Ile Asp Tyr Leu Lys
    210     215     220

His Leu Ser Lys Val Lys Ile Pro Ser Asp Phe Glu Gly Ser Gly
225     230     235     240

Tyr Thr Asp Leu Gln Glu Arg Gly Asp Asn Asp Ile Ser Pro Phe Ser
    245     250     255

Gly Asp Gly Gln Pro Phe Lys Asp Ile Pro Gly Lys Gly Glu Ala Thr
   260     265     270

Gly Pro Asp Leu Glu Gly Lys Asp Ile Gln Thr Gly Phe Ala Gly Pro
   275     280     285

Ser Glu Ala Glu Ser Thr His Leu Asp Thr Lys Lys Pro Gly Tyr Asn
   290     295     300

Glu Ile Pro Glu Arg Glu Glu Asn Gly Gly Asn Thr Ile Gly Thr Arg
305     310     315     320

Asp Glu Thr Ala Lys Glu Ala Asp Ala Val Asp Val Ser Leu Val Glu
    325     330     335

Gly Ser Asn Asp Ile Met Gly Ser Thr Asn Phe Lys Glu Leu Pro Gly
   340     345     350

Arg Glu Gly Asn Arg Val Asp Ala Gly Ser Gln Asn Ala His Gln Gly
   355     360     365

Lys Val Glu Phe His Tyr Pro Pro Ala Pro Ser Lys Glu Lys Arg Lys
 370     375     380

Glu Gly Ser Ser Asp Ala Ala Glu Ser Thr Asn Tyr Asn Glu Ile Pro
385     390     395     400

Lys Asn Gly Lys Gly Ser Thr Arg Lys Gly Val Asp His Ser Asn Arg
    405     410     415

```
Asn Gln Ala Thr Leu Asn Glu Lys Gln Arg Phe Pro Ser Lys Gly Lys
                420                 425                 430

Ser Gln Gly Leu Pro Ile Pro Ser Arg Gly Leu Asp Asn Glu Ile Lys
        435                 440                 445

Asn Glu Met Asp Ser Phe Asn Gly Pro Ser His Glu Asn Ile Ile Thr
    450                 455                 460

His Gly Arg Lys Tyr His Tyr Val Pro His Arg Gln Asn Asn Ser Thr
465                 470                 475                 480

Arg Asn Lys Gly Met Pro Gln Gly Lys Gly Ser Trp Gly Arg Gln Pro
                485                 490                 495

His Ser Asn Arg Arg Phe Ser Ser Arg Arg Asp Asp Ser Ser Glu
                500                 505                 510

Ser Ser Asp Ser Gly Ser Ser Glu Ser Asp Gly Asp
        515                 520                 525

<210> SEQ ID NO 7
<211> LENGTH: 2112
<212> TYPE: DNA
<213> ORGANISM: Homo sapiens

<400> SEQUENCE: 7
caaactttaa atttcagcaa aatgcccaga gacttctaat cctgcaacaa gaagccaggt      60
attctgaagg tgaaagatac cagagattct caaagatgcg agttttctgt gtgggactac     120
tcctttcag tgtgacctgg gcagcaccaa catttcaacc acagactgag aaaactaagc      180
aaagctgtgt ggaagagcag aggataacat acaagggtca ctatgagaaa catgggcatt     240
atgttttaa gtgtgtttac atgtcacctg agaagaaaaa tcaaactgat gtaaagcagg      300
aagaaaaaa caaagacaat attggttttc accatttggg caagagaata aatcaagagc      360
tatcatctaa agaaatatt gtccaggaaa gaaagaaaga tttgtccctt tctgaagcca      420
gtgagaataa gggaagtagt aaatctcaaa attatttcac aaatagacag agactgaata      480
aagaatatag tatcagtaac aaagagaata ctcacaatgg cctgaggatg tcaatttatc     540
ctaagtcaac tggaataaaa gggtttgagg atggagatga tgctatcagc aaactacatg     600
accaagaaga atatggcgca gctctcatca gaaataacat gcaacatata atgggccag      660
tgactgcgat taaactcctg ggggaagaaa acaaagagaa cacacctagg aatgttctaa     720
acataatccc agcaagtatg aattatgcta agcacactc gaaggataaa aagaagcctc      780
aaagagattc ccaagcccag aaaagtccag taaaaagcaa aagcacccat cgtattcaac      840
acaacattga ctacctaaaa catctctcaa aagtcaaaaa aatccccagt gattttgaag      900
gcagcggtta tacagatctt caagagagag gggacaatga tatatctcct ttcagtgggg     960
acggccaacc ttttaaggac attcctggta aaggagaagc tactggtcct gacctagaag    1020
gcaaagatat tcaaacaggg tttgcaggcc caagtgaagc tgagagtact catcttgaca     1080
caaaaaagcc aggttataat gagatcccag agagagaaga aaatggtgga ataccattg      1140
gaactaggga tgaaactgcg aaagaggcag atgctgttga tgtcagcctt gtagagggca     1200
gcaacgatat catgggtagt accaatttta aggagctccc tggaagagaa ggaaacagag     1260
tggatgctgg cagccaaaat gctcaccaag ggaaggttga gttcattac cctcctgcac      1320
cctcaaaaga gaaagaaaaa gaaggcagta gtgatgcagc tgaaagtacc aactataatg     1380
aaattcctaa aaatgcaaa ggcagtacca gaaagggtgt agatcattct aataggaacc      1440
aagcaacctt aaatgaaaaa caaaggtttc ctagtaaggg caaaagtcag ggcctgccca     1500
```

-continued

```
ttccttctcg tggtcttgat aatgaaatca aaaacgaaat ggattccttt aatggcccca      1560
gtcatgagaa tataataaca catggcagaa aatatcatta tgtacccccac agacaaaata    1620 attctacacg gaataagggt atgccacaag ggaaaggctc ctggggtaga caaccccatt     1680
ccaacaggag gtttagttcc cgtagaaggg atgacagtag tgagtcatct gacagtggca     1740
gttcaagtga gagcgatggt gactagtcca ccaggagttc ccagcggggt gacagtctga     1800
agacctcgtc acctgtgagt tgatgtagag gagagccacc tgacagctga ccaggtgaag     1860
agaggataga gtgaagaact gagtgagcca agaatcctgg tctccttggg ggaattttg     1920 ctatcttaat agtcacagta taaaattcta ttaaaggcta taatgttttt aagcaaaaaa     1980
aaatcattac agatctatga aataggtaac atttgagtag gtgtcattta aaaatagttg     2040
gtgaatgtca caaatgcctt ctatgttgtt tgctctgtag acatgaaaat aaacaatatc     2100
tctcgatgat aa                                                         2112
```

<210> SEQ ID NO 8
<211> LENGTH: 556
<212> TYPE: PRT
<213> ORGANISM: Homo sapiens

<400> SEQUENCE: 8

```
Met Arg Val Phe Cys Val Gly Leu Leu Leu Phe Ser Val Thr Trp Ala
 1               5                  10                  15

Ala Pro Thr Phe Gln Pro Gln Thr Glu Lys Thr Lys Gln Ser Cys Val
                20                  25                  30

Glu Glu Gln Arg Ile Thr Tyr Lys Gly His Tyr Glu Lys His Gly His
            35                  40                  45

Tyr Val Phe Lys Cys Val Tyr Met Pro Pro Glu Lys Lys Asn Gln Thr
        50                  55                  60

Asp Val Lys Gln Glu Glu Lys Asn Lys Asp Asn Ile Gly Phe His His
65                  70                  75                  80

Leu Gly Lys Arg Ile Asn Gln Glu Leu Ser Ser Lys Glu Asn Ile Val
                85                  90                  95

Gln Glu Arg Lys Lys Asp Leu Ser Leu Ser Glu Ala Ser Glu Asn Lys
            100                 105                 110

Gly Ser Ser Lys Ser Gln Asn Tyr Phe Thr Asn Arg Gln Arg Leu Asn
        115                 120                 125

Lys Glu Tyr Ser Ile Ser Asn Lys Glu Asn Thr His Asn Gly Leu Arg
    130                 135                 140

Met Ser Ile Tyr Pro Lys Ser Thr Gly Asn Lys Gly Phe Glu Asp Gly
145                 150                 155                 160

Asp Asp Ala Ile Ser Lys Leu His Asp Gln Glu Tyr Gly Ala Ala
                165                 170                 175

Leu Ile Arg Asn Asn Met Gln His Ile Met Gly Pro Val Thr Ala Ile
            180                 185                 190

Lys Leu Leu Gly Glu Glu Asn Lys Glu Asn Thr Pro Arg Asn Val Leu
        195                 200                 205

Asn Ile Ile Pro Ala Ser Met Asn Tyr Ala Lys Ala His Ser Lys Asp
    210                 215                 220

Lys Lys Pro Gln Arg Asp Ser Gln Ala Gln Lys Ser Pro Val Lys
225                 230                 235                 240

Ser Lys Ser Thr His Arg Ile Gln His Asn Ile Asp Tyr Leu Lys His
                245                 250                 255
```

```
Leu Ser Lys Val Lys Lys Ile Pro Ser Asp Phe Glu Gly Ser Gly Tyr
            260                 265                 270
Thr Asp Leu Gln Glu Arg Gly Asp Asn Asp Ile Ser Pro Phe Ser Gly
            275                 280                 285
Asp Gly Gln Pro Phe Lys Asp Ile Pro Gly Lys Gly Glu Ala Thr Gly
            290                 295                 300
Pro Asp Leu Glu Gly Lys Asp Ile Gln Thr Gly Phe Ala Gly Pro Ser
305                 310                 315                 320
Glu Ala Glu Ser Thr His Leu Asp Thr Lys Lys Pro Gly Tyr Asn Glu
                325                 330                 335
Ile Pro Glu Arg Glu Glu Asn Gly Gly Asn Thr Ile Gly Thr Arg Asp
            340                 345                 350
Glu Thr Ala Lys Glu Ala Asp Ala Val Asp Val Ser Leu Val Glu Gly
            355                 360                 365
Ser Asn Asp Ile Met Gly Ser Thr Asn Phe Lys Glu Leu Pro Gly Arg
            370                 375                 380
Glu Gly Asn Arg Val Asp Ala Gly Ser Gln Asn Ala His Gln Gly Lys
385                 390                 395                 400
Val Glu Phe His Tyr Pro Pro Ala Pro Ser Lys Glu Lys Arg Lys Glu
                405                 410                 415
Gly Ser Ser Asp Ala Ala Glu Ser Thr Asn Tyr Asn Glu Ile Pro Lys
            420                 425                 430
Asn Gly Lys Gly Ser Thr Arg Lys Gly Val Asp His Ser Asn Arg Asn
            435                 440                 445
Gln Ala Thr Leu Asn Glu Lys Gln Arg Phe Pro Ser Lys Gly Lys Ser
            450                 455                 460
Gln Gly Leu Pro Ile Pro Ser Arg Gly Leu Asp Asn Glu Ile Lys Asn
465                 470                 475                 480
Glu Met Asp Ser Phe Asn Gly Pro Ser His Glu Asn Ile Ile Thr His
                485                 490                 495
Gly Arg Lys Tyr His Tyr Val Pro His Arg Gln Asn Asn Ser Thr Arg
            500                 505                 510
Asn Lys Gly Met Pro Gln Gly Lys Gly Ser Trp Gly Arg Gln Pro His
            515                 520                 525
Ser Asn Arg Arg Phe Ser Ser Arg Arg Arg Asp Asp Ser Ser Glu Ser
            530                 535                 540
Ser Asp Ser Gly Ser Ser Ser Glu Ser Asp Gly Asp
545                 550                 555

<210> SEQ ID NO 9
<211> LENGTH: 22
<212> TYPE: DNA
<213> ORGANISM: Rattus norvegicus

<400> SEQUENCE: 9
gccgctctag aactagtgga tc                                         22

<210> SEQ ID NO 10
<211> LENGTH: 21
<212> TYPE: DNA
<213> ORGANISM: Rattus norvegicus

<400> SEQUENCE: 10
aggtcgacgg tatcgataag c                                          21
```

```
<210> SEQ ID NO 11
<211> LENGTH: 20
<212> TYPE: DNA
<213> ORGANISM: Rattus norvegicus

<400> SEQUENCE: 11
gttaggtagt gcgtgcttcg                                              20

<210> SEQ ID NO 12
<211> LENGTH: 21
<212> TYPE: DNA
<213> ORGANISM: Rattus norvegicus

<400> SEQUENCE: 12
ggacatctgt tggaattacg c                                            21

<210> SEQ ID NO 13
<211> LENGTH: 21
<212> TYPE: DNA
<213> ORGANISM: Rattus norvegicus

<400> SEQUENCE: 13
ccaagactca ctgggtacgt c                                            21

<210> SEQ ID NO 14
<211> LENGTH: 20
<212> TYPE: DNA
<213> ORGANISM: Rattus norvegicus

<400> SEQUENCE: 14
ctagaggggc ctgttgaacc                                              20

<210> SEQ ID NO 15
<211> LENGTH: 22
<212> TYPE: DNA
<213> ORGANISM: Rattus norvegicus

<400> SEQUENCE: 15
aaggtgaacg acaccagaga gc                                           22

<210> SEQ ID NO 16
<211> LENGTH: 21
<212> TYPE: DNA
<213> ORGANISM: Rattus norvegicus

<400> SEQUENCE: 16
tgaccaagtc tggtaccttg c                                            21

<210> SEQ ID NO 17
<211> LENGTH: 31
<212> TYPE: DNA
<213> ORGANISM: Rattus norvegicus

<400> SEQUENCE: 17
gccggatcca tgcaggctgt gtctgttgga c                                 31

<210> SEQ ID NO 18
<211> LENGTH: 28
<212> TYPE: DNA
<213> ORGANISM: Rattus norvegicus

<400> SEQUENCE: 18
gccgaattcc aggaccagag ctgggaac                                     28
```

<210> SEQ ID NO 19
<211> LENGTH: 22
<212> TYPE: DNA
<213> ORGANISM: Mus musculus

<400> SEQUENCE: 19
tgtgtcaggt agtgagtgct cc                                        22

<210> SEQ ID NO 20
<211> LENGTH: 20
<212> TYPE: DNA
<213> ORGANISM: Mus musculus

<400> SEQUENCE: 20
actgccacca tgtccttctc                                           20

<210> SEQ ID NO 21
<211> LENGTH: 21
<212> TYPE: DNA
<213> ORGANISM: Mus musculus

<400> SEQUENCE: 21
ccaagactca ctgggtactg c                                         21

<210> SEQ ID NO 22
<211> LENGTH: 20
<212> TYPE: DNA
<213> ORGANISM: Mus musculus

<400> SEQUENCE: 22
ctagaggggc ctgttgaacc                                           20

<210> SEQ ID NO 23
<211> LENGTH: 20
<212> TYPE: DNA
<213> ORGANISM: Mus musculus

<400> SEQUENCE: 23
tttcctgaag gtgaatgacg                                           20

<210> SEQ ID NO 24
<211> LENGTH: 23
<212> TYPE: DNA
<213> ORGANISM: Mus musculus

<400> SEQUENCE: 24
ctagtcacca tgactctcac tag                                       23

<210> SEQ ID NO 25
<211> LENGTH: 25
<212> TYPE: DNA
<213> ORGANISM: Mus musculus

<400> SEQUENCE: 25
gccggatcca tgacgccaga gggcc                                     25

<210> SEQ ID NO 26
<211> LENGTH: 23
<212> TYPE: DNA
<213> ORGANISM: Mus musculus

<400> SEQUENCE: 26
ctagtcacca tgactctcac tag                                       23

<210> SEQ ID NO 27
<211> LENGTH: 25
<212> TYPE: DNA
<213> ORGANISM: Mus musculus

<400> SEQUENCE: 27
ggatccatgc cgaatgaaga cagga                                    25

<210> SEQ ID NO 28
<211> LENGTH: 23
<212> TYPE: DNA
<213> ORGANISM: Mus musculus

<400> SEQUENCE: 28
ctagtcacca tgactctcac tag                                      23

<210> SEQ ID NO 29
<211> LENGTH: 19
<212> TYPE: DNA
<213> ORGANISM: Mus musculus

<400> SEQUENCE: 29
tttcagcaaa tgcccagag                                           19

<210> SEQ ID NO 30
<211> LENGTH: 22
<212> TYPE: DNA
<213> ORGANISM: Mus musculus

<400> SEQUENCE: 30
ccaggtcata ctgaagagga gc                                       22

<210> SEQ ID NO 31
<211> LENGTH: 20
<212> TYPE: DNA
<213> ORGANISM: Mus musculus

<400> SEQUENCE: 31
actatccaca agtggcctcg                                          20

<210> SEQ ID NO 32
<211> LENGTH: 20
<212> TYPE: DNA
<213> ORGANISM: Mus musculus

<400> SEQUENCE: 32
ctgttggctt gctcagttcc                                          20

<210> SEQ ID NO 33
<211> LENGTH: 1876
<212> TYPE: DNA
<213> ORGANISM: Homo sapiens

<400> SEQUENCE: 33
gcaccaacat ttcaaccaca gactgagaaa actaagcaaa gctgtgtgga agagcagagg    60
caggaagaaa aaacaaaga caatattggt tttcaccatt tgggcaagag aataaatcaa    120
gagctatcat ctaaagaaaa tattgtccag gaaagaaaga aagatttgtc cctttctgaa    180
gccagtgaga ataagggaag tagtaaatct caaaattatt tcacaaatag acagagactg    240
aataaagaat atagtatcag taacaaagag aatactcaca atggcctgag gatgtcaatt    300
tatcctaagt caactgggaa taagggtttt gaggatggag atgatgctat cagcaaacta    360

-continued

```
catgaccaag aagaatatgg cgcagctctc atcagaaata acatgcaaca tataatgggg      420
ccagtgactg cgattaaact cctgggggaa gaaaacaaag agaacacacc taggaatgtt      480
ctaaacataa tcccagcaag tatgaattat gctaaagcac actcgaagga taaaaagaag      540
cctcaaagag attcccaagc ccagaaaagt ccagtaaaaa gcaaaagcac ccatcgtatt      600
caacacaaca ttgactacct aaaacatctc tcaaaagtca aaaaaatccc cagtgatttt      660
gaaggcagcg gttatacaga tcttcaagag agagggggaca atgatatatc tcctttcagt      720
ggggacggcc aacctttttaa ggacattcct ggtaaaggag aagctactgg tcctgaccta      780
gaaggcaaag atattcaaac agggtttgca ggcccaagtg aagctgagag tactcatctt      840
gacacaaaaa agccaggtta taatgagatc ccagagagag aagaaaatgg tggaaatacc      900
attggaacta gggatgaaac tgcgaaagag gcagatgctg ttgatgtcag ccttgtagag      960
ggcagcaacg atatcatggg tagtaccaat tttaaggagc tccctggaag agaaggaaac     1020
agagtggatc tggcagcca aatgctcac caagggaagt tgagtttca ttaccctcct     1080
gcaccctcaa aagagaaaag aaaagaaggc agtagtgatg cagctgaaag taccaactat     1140
aatgaaattc ctaaaaatgg caaaggcagt accagaaagg gtgtagatca ttctaatagg     1200
aaccaagcaa ccttaaatga aaaacaaagg tttcctagta agggcaaaag tcagggcctg     1260
cccattcctt ctcgtggtct tgataatgaa atcaaaaacg aaatggattc ctttaatggc     1320
cccagtcatg agaatataat aacacatggc agaaaatatc attatgtacc ccacagacaa     1380
aataattcta cacggaataa gggtatgcca caagggaaag ctcctgggg tagacaaccc     1440
cattccaaca ggaggtttag ttcccgtaga agggatgaca gtagtgagtc atctgacagt     1500
ggcagttcaa gtgagagcga tggtgactag tccaccagga gttcccagcg ggtgacagt     1560
ctgaagacct cgtcacctgt gagttgatgt agaggagagc cacctgacag ctgaccaggt     1620
gaagagagga tagagtgaag aactgagtga gccaagaatc ctggtctcct tgggggaatt     1680
tttgctatct taatagtcac agtataaaat tctattaaag gctataatgt ttttaagcaa     1740
aaaaaaatca ttacagatct atgaaatagg taacatttga gtaggtgtca tttaaaaata     1800
gttggtgaat gtcacaaatg ccttctatgt tgtttgctct gtagacatga aaataaacaa     1860
tatctctcga tgataa                                                     1876
```

<210> SEQ ID NO 34
<211> LENGTH: 509
<212> TYPE: PRT
<213> ORGANISM: Homo sapiens

<400> SEQUENCE: 34

```
Ala Pro Thr Phe Gln Pro Gln Thr Glu Lys Thr Lys Gln Ser Cys Val
 1               5                  10                  15

Glu Glu Gln Arg Gln Glu Glu Lys Asn Lys Asp Asn Ile Gly Phe His
            20                  25                  30

His Leu Gly Lys Arg Ile Asn Gln Glu Leu Ser Ser Lys Glu Asn Ile
        35                  40                  45

Val Gln Glu Arg Lys Lys Asp Leu Ser Leu Ser Glu Ala Ser Glu Asn
    50                  55                  60

Lys Gly Ser Ser Lys Ser Gln Asn Tyr Phe Thr Asn Arg Gln Arg Leu
65                  70                  75                  80

Asn Lys Glu Tyr Ser Ile Ser Asn Lys Glu Asn Thr His Asn Gly Leu
                85                  90                  95
```

-continued

```
Arg Met Ser Ile Tyr Pro Lys Ser Thr Gly Asn Lys Gly Phe Glu Asp
            100                 105                 110
Gly Asp Asp Ala Ile Ser Lys Leu His Asp Gln Glu Glu Tyr Gly Ala
            115                 120                 125
Ala Leu Ile Arg Asn Asn Met Gln His Ile Met Gly Pro Val Thr Ala
    130                 135                 140
Ile Lys Leu Leu Gly Glu Glu Asn Lys Glu Asn Thr Pro Arg Asn Val
145                 150                 155                 160
Leu Asn Ile Ile Pro Ala Ser Met Asn Tyr Ala Lys Ala His Ser Lys
                165                 170                 175
Asp Lys Lys Lys Pro Gln Arg Asp Ser Gln Ala Gln Lys Ser Pro Val
            180                 185                 190
Lys Ser Lys Ser Thr His Arg Ile Gln His Asn Ile Asp Tyr Leu Lys
            195                 200                 205
His Leu Ser Lys Val Lys Lys Ile Pro Ser Asp Phe Glu Gly Ser Gly
    210                 215                 220
Tyr Thr Asp Leu Gln Glu Arg Gly Asp Asn Asp Ile Ser Pro Phe Ser
225                 230                 235                 240
Gly Asp Gly Gln Pro Phe Lys Asp Ile Pro Gly Lys Gly Glu Ala Thr
                245                 250                 255
Gly Pro Asp Leu Glu Gly Lys Asp Ile Gln Thr Gly Phe Ala Gly Pro
            260                 265                 270
Ser Glu Ala Glu Ser Thr His Leu Asp Thr Lys Lys Pro Gly Tyr Asn
            275                 280                 285
Glu Ile Pro Glu Arg Glu Glu Asn Gly Gly Asn Thr Ile Gly Thr Arg
    290                 295                 300
Asp Glu Thr Ala Lys Glu Ala Asp Ala Val Asp Val Ser Leu Val Glu
305                 310                 315                 320
Gly Ser Asn Asp Ile Met Gly Ser Thr Asn Phe Lys Glu Leu Pro Gly
                325                 330                 335
Arg Glu Gly Asn Arg Val Asp Ala Gly Ser Gln Asn Ala His Gln Gly
            340                 345                 350
Lys Val Glu Phe His Tyr Pro Pro Ala Pro Ser Lys Glu Lys Arg Lys
            355                 360                 365
Glu Gly Ser Ser Asp Ala Ala Glu Ser Thr Asn Tyr Asn Glu Ile Pro
    370                 375                 380
Lys Asn Gly Lys Gly Ser Thr Arg Lys Gly Val Asp His Ser Asn Arg
385                 390                 395                 400
Asn Gln Ala Thr Leu Asn Glu Lys Gln Arg Phe Pro Ser Lys Gly Lys
                405                 410                 415
Ser Gln Gly Leu Pro Ile Pro Ser Arg Gly Leu Asp Asn Glu Ile Lys
            420                 425                 430
Asn Glu Met Asp Ser Phe Asn Gly Pro Ser His Glu Asn Ile Ile Thr
            435                 440                 445
His Gly Arg Lys Tyr His Tyr Val Pro His Arg Gln Asn Asn Ser Thr
    450                 455                 460
Arg Asn Lys Gly Met Pro Gln Gly Lys Gly Ser Trp Gly Arg Gln Pro
465                 470                 475                 480
His Ser Asn Arg Arg Phe Ser Arg Arg Asp Asp Ser Glu
                485                 490                 495
Ser Ser Asp Ser Gly Ser Ser Glu Ser Asp Gly Asp
            500                 505
```

```
<210> SEQ ID NO 35
<211> LENGTH: 20
<212> TYPE: DNA
<213> ORGANISM: Homo sapiens

<400> SEQUENCE: 35
caaactttaa tttcagcaaa                                               20

<210> SEQ ID NO 36
<211> LENGTH: 20
<212> TYPE: DNA
<213> ORGANISM: Homo sapiens

<400> SEQUENCE: 36
gcgccatatt cttcttggtc                                               20

<210> SEQ ID NO 37
<211> LENGTH: 23
<212> TYPE: DNA
<213> ORGANISM: Homo sapiens

<400> SEQUENCE: 37
ctttaaattt cagcaaaatg ccc                                           23

<210> SEQ ID NO 38
<211> LENGTH: 20
<212> TYPE: DNA
<213> ORGANISM: Homo sapiens

<400> SEQUENCE: 38
catcctcagg ccattgtgag                                               20

<210> SEQ ID NO 39
<211> LENGTH: 23
<212> TYPE: DNA
<213> ORGANISM: Homo sapiens

<400> SEQUENCE: 39
gccatgcgag ttttctgtgt ggg                                           23

<210> SEQ ID NO 40
<211> LENGTH: 20
<212> TYPE: DNA
<213> ORGANISM: Homo sapiens

<400> SEQUENCE: 40
tggtggacta gtcaccatcg                                               20

<210> SEQ ID NO 41
<211> LENGTH: 20
<212> TYPE: DNA
<213> ORGANISM: Homo sapiens

<400> SEQUENCE: 41
agatgctgtt gatgtcagcc                                               20

<210> SEQ ID NO 42
<211> LENGTH: 20
<212> TYPE: DNA
<213> ORGANISM: Homo sapiens

<400> SEQUENCE: 42
aagaccacga gaaggaatgg                                               20
```

```
<210> SEQ ID NO 43
<211> LENGTH: 467
<212> TYPE: DNA
<213> ORGANISM: Mus musculus

<400> SEQUENCE: 43
agcttctcta atgtccgccc tatggtaggt gctcaaagca tcattggtgt ctgaataaga      60
ttcagataca attaaggttg tacattctct aaataaaaca acaaaactac ttttcactta     120
taaatttgtt ggtttacaaa tatttcctac ttacacgtat gcaacccatt cacccagtcc     180
tagttaatag ttctaaaaat cagttctaat tattttgcaa cataatgtcc aaactgagat     240
atttatattt ttttctgtt tattctactt tctggaacat ttgatagcag ctttccacca      300
caaaacattt ttagattaaa attaccatac ccctgtggt catctgtggg catttgtgac      360
agactccgtg ctggtactga gtgaaccatg ctgattggac atcggggct ctcacaaact      420 ttaaatttca gcaaatgccc agagactaag cccgaagaag ccaagct                   467

<210> SEQ ID NO 44
<211> LENGTH: 447
<212> TYPE: PRT
<213> ORGANISM: Homo sapiens

<400> SEQUENCE: 44

Met Lys Thr Val Ile Leu Leu Thr Phe Leu Trp Gly Leu Ser Cys Ala
  1               5                  10                  15

Leu Pro Val Ala Arg Tyr Gln Asn Thr Glu Ser Glu Ser Ser Glu Glu
                 20                  25                  30

Arg Thr Gly Asn Leu Ala Gln Ser Pro Pro Pro Met Ala Asn Ser
             35                  40                  45

Asp His Thr Asp Ser Ser Glu Ser Gly Glu Glu Leu Gly Ser Asp Arg
     50                  55                  60

Ser Gln Tyr Arg Pro Ala Gly Gly Leu Ser Lys Ser Ala Gly Met Asp
 65                  70                  75                  80

Ala Asp Lys Glu Glu Asp Glu Asp Ser Gly Asp Asp Thr Phe Gly
                 85                  90                  95

Asp Glu Asp Asn Gly Pro Gly Pro Glu Glu Arg Gln Trp Gly Gly Pro
            100                 105                 110

Ser Arg Leu Asp Ser Asp Glu Asp Ser Ala Asp Thr Thr Gln Ser Ser
            115                 120                 125

Glu Asp Ser Thr Ser Gln Glu Asn Ser Ala Gln Asp Thr Pro Ser Asp
        130                 135                 140

Ser Lys Asp His His Ser Asp Glu Ala Asp Ser Arg Pro Glu Ala Gly
145                 150                 155                 160

Asp Ser Thr Gln Asp Ser Glu Ser Glu Glu Tyr Arg Val Gly Gly Gly
                165                 170                 175

Ser Glu Gly Glu Ser Ser His Gly Asp Gly Ser Glu Phe Asp Asp Glu
            180                 185                 190

Gly Met Gln Ser Asp Asp Pro Gly Ser Thr Arg Ser Asp Arg Gly His
            195                 200                 205

Thr Arg Met Ser Ser Ala Gly Ile Arg Ser Glu Glu Ser Lys Gly Asp
        210                 215                 220

His Glu Pro Thr Thr Gln Asp Ser Asp Ser Gln Asp Val Glu
225                 230                 235                 240

Phe Ser Ser Arg Lys Ser Phe Arg Arg Ser Arg Val Ser Glu Glu Asp
                245                 250                 255
```

| | | | | | | | | | | | |
|---|---|---|---|---|---|---|---|---|---|---|---|
|Asp|Arg|Gly|Glu|Leu|Ala|Asp|Ser|Asn|Ser|Arg|Glu|Thr|Gln|Ser|Val|
| | | |260| | | |265| | | |270|
|Ser|Thr|Glu|Asp|Phe|Arg|Ser|Lys|Glu|Glu|Ser|Arg|Ser|Glu|Thr|Gln|
| | |275| | | |280| | | |285| |
|Glu|Asp|Thr|Ala|Glu|Thr|Gln|Ser|Gln|Glu|Asp|Ser|Pro|Glu|Gly|Gln|
| |290| | | |295| | | |300| | |
|Asp|Pro|Ser|Ser|Glu|Ser|Ser|Glu|Glu|Ala|Gly|Glu|Pro|Ser|Gln|Glu|
|305| | | |310| | | |315| | | |320|
|Ser|Ser|Ser|Glu|Ser|Gln|Glu|Gly|Val|Ala|Ser|Glu|Ser|Arg|Gly|Asp|
| | | |325| | | |330| | | |335|
|Asn|Pro|Asp|Asn|Thr|Ser|Gln|Thr|Gly|Asp|Gln|Arg|Asp|Ser|Glu|Ser|
| | |340| | | |345| | | |350| |
|Ser|Glu|Glu|Asp|Arg|Leu|Asn|Thr|Phe|Ser|Ser|Glu|Ser|Gln|Ser|
| |355| | | |360| | | |365| |
|Thr|Glu|Glu|Gln|Gly|Asp|Ser|Glu|Ser|Asn|Glu|Ser|Leu|Ser|Leu|Ser|
| |370| | | |375| | | |380| | |
|Glu|Glu|Ser|Gln|Glu|Ser|Ala|Gln|Asp|Glu|Asp|Ser|Ser|Gln|Glu|
|385| | | |390| | | |395| | | |400|
|Gly|Leu|Gln|Ser|Gln|Ser|Ala|Ser|Arg|Glu|Ser|Arg|Ser|Gln|Glu|Ser|
| | | |405| | | |410| | | |415|
|Gln|Ser|Glu|Gln|Asp|Ser|Arg|Ser|Glu|Glu|Asn|Arg|Asp|Ser|Asp|Ser|
| | |420| | | |425| | | |430| |
|Gln|Asp|Ser|Ser|Arg|Ser|Lys|Glu|Glu|Ser|Asn|Ser|Thr|Gly|Ser|
| | |435| | | |440| | | |445|

<210> SEQ ID NO 45
<211> LENGTH: 1969
<212> TYPE: DNA
<213> ORGANISM: Homo sapiens

<400> SEQUENCE: 45

```
gcaccaacat tcaaccaca gactgagaaa actaagcaaa gctgtgtgga agagcagagg      60
ataacataca agggtcacta tgagaaacat gggcattatg tttttaagtg tgtttacatg    120
tcacctgaga agaaaaatca aactgatgta aagcaggaag aaaaaaacaa agacaatatt    180
ggttttcacc atttgggcaa gagaataaat caagagctat catctaaaga aaatattgtc    240
caggaaagaa agaaagattt gtcccttct gaagccagtg agaataaggg aagtagtaaa     300
tctcaaaatt atttcacaaa tagacagaga ctgaataaag aatatagtat cagtaacaaa    360
gagaatactc acaatggcct gaggatgtca atttatccta agtcaactgg gaataaaggg    420
tttgaggatg gagatgatgc tatcagcaaa ctacatgacc aagaagaata tggcgcagct    480
ctcatcagaa ataacatgca acatataatg gggccagtga ctgcgattaa actcctgggg    540
gaagaaaaca agagaacac acctaggaat gttctaaaca taatcccagc aagtatgaat    600
tatgctaaag cacactcgaa ggataaaaag aagcctcaaa gagattccca agcccagaaa    660
agtccagtaa aaagcaaaag cacccatcgt attcaacaca acattgacta cctaaaacat    720
ctctcaaaag tcaaaaaaat ccccagtgat tttgaaggca gcggttatac agatcttcaa    780
gagagagggg acaatgatat atctcctttc agtggggacg ccaacctttt taaggacatt    840
cctggtaaag gagaagctac tggtcctgac ctagaaggca agatattca acagggttt     900
gcaggcccaa gtgaagctga gagtactcat cttgacacaa aaagccagg ttataatgag    960
atcccagaga gagaagaaaa tggtggaaat accattggaa ctagggatga aactgcgaaa   1020
gaggcagatg ctgttgatgt cagccttgta gagggcagca acgatatcat gggtagtacc   1080
```

```
aattttaagg agctccctgg aagagaagga aacagagtgg atgctggcag ccaaaatgct   1140
caccaaggga aggttgagtt tcattaccct cctgcaccct caaaagagaa aagaaaagaa   1200
ggcagtagtg atgcagctga agtaccaac tataatgaaa ttcctaaaaa tggcaaaggc    1260
agtaccagaa agggtgtaga tcattctaat aggaaccaag caaccttaaa tgaaaaacaa   1320
aggtttccta gtaagggcaa aagtcagggc ctgcccattc cttctcgtgg tcttgataat   1380
gaaatcaaaa acgaaatgga ttcctttaat ggccccagtc atgagaatat aataacacat   1440
ggcagaaaat atcattatgt accccacaga caaaataatt ctacacggaa taagggtatg   1500
ccacaaggga aaggctcctg gggtagacaa ccccattcca acaggaggtt tagttcccgt   1560
agaagggatg acagtagtga gtcatctgac agtggcagtt caagtgagag cgatggtgac   1620
tagtccacca ggagttccca gcggggtgac agtctgaaga cctcgtcacc tgtgagttga   1680
tgtagaggag agccacctga cagctgacca ggtgaagaga ggatagagtg aagaactgag   1740
tgagccaaga atcctggtct ccttggggga atttttgcta tcttaatagt cacagtataa   1800
aattctatta aaggctataa tgttttttaag caaaaaaaaa tcattacaga tctatgaaat   1860
aggtaacatt tgagtaggtg tcatttaaaa atagttggtg aatgtcacaa atgccttcta   1920
tgttgtttgc tctgtagaca tgaaaataaa caatatctct cgatgataa                1969

<210> SEQ ID NO 46
<211> LENGTH: 540
<212> TYPE: PRT
<213> ORGANISM: Homo sapiens

<400> SEQUENCE: 46

Ala Pro Thr Phe Gln Pro Gln Thr Glu Lys Thr Lys Gln Ser Cys Val
  1               5                  10                  15

Glu Glu Gln Arg Ile Thr Tyr Lys Gly His Tyr Glu Lys His Gly His
             20                  25                  30

Tyr Val Phe Lys Cys Val Tyr Met Ser Pro Glu Lys Lys Asn Gln Thr
         35                  40                  45

Asp Val Lys Gln Glu Glu Lys Asn Lys Asp Asn Ile Gly Phe His His
     50                  55                  60

Leu Gly Lys Arg Ile Asn Gln Glu Leu Ser Ser Lys Glu Asn Ile Val
 65                  70                  75                  80

Gln Glu Arg Lys Lys Asp Leu Ser Leu Ser Glu Ala Ser Glu Asn Lys
                 85                  90                  95

Gly Ser Ser Lys Ser Gln Asn Tyr Phe Thr Asn Arg Gln Arg Leu Asn
            100                 105                 110

Lys Glu Tyr Ser Ile Ser Asn Lys Glu Asn Thr His Asn Gly Leu Arg
        115                 120                 125

Met Ser Ile Tyr Pro Lys Ser Thr Gly Asn Lys Gly Phe Glu Asp Gly
    130                 135                 140

Asp Asp Ala Ile Ser Lys Leu His Asp Gln Glu Tyr Gly Ala Ala
145                 150                 155                 160

Leu Ile Arg Asn Asn Met Gln His Ile Met Gly Pro Val Thr Ala Ile
                165                 170                 175

Lys Leu Leu Gly Glu Glu Asn Lys Glu Asn Thr Pro Arg Asn Val Leu
            180                 185                 190

Asn Ile Ile Pro Ala Ser Met Asn Tyr Ala Lys Ala His Ser Lys Asp
        195                 200                 205

Lys Lys Lys Pro Gln Arg Asp Ser Gln Ala Gln Lys Ser Pro Val Lys
    210                 215                 220
```

-continued

```
Ser Lys Ser Thr His Arg Ile Gln His Asn Ile Asp Tyr Leu Lys His
225                 230                 235                 240

Leu Ser Lys Val Lys Lys Ile Pro Ser Asp Phe Glu Gly Ser Gly Tyr
            245                 250                 255

Thr Asp Leu Gln Glu Arg Gly Asp Asn Asp Ile Ser Pro Phe Ser Gly
            260                 265                 270

Asp Gly Gln Pro Phe Lys Asp Ile Pro Gly Lys Gly Glu Ala Thr Gly
        275                 280                 285

Pro Asp Leu Glu Gly Lys Asp Ile Gln Thr Gly Phe Ala Gly Pro Ser
        290                 295                 300

Glu Ala Glu Ser Thr His Leu Asp Thr Lys Lys Pro Gly Tyr Asn Glu
305                 310                 315                 320

Ile Pro Glu Arg Glu Glu Asn Gly Gly Asn Thr Ile Gly Thr Arg Asp
                325                 330                 335

Glu Thr Ala Lys Glu Ala Asp Ala Val Asp Val Ser Leu Val Glu Gly
            340                 345                 350

Ser Asn Asp Ile Met Gly Ser Thr Asn Phe Lys Glu Leu Pro Gly Arg
        355                 360                 365

Glu Gly Asn Arg Val Asp Ala Gly Ser Gln Asn Ala His Gln Gly Lys
    370                 375                 380

Val Glu Phe His Tyr Pro Pro Ala Pro Ser Lys Glu Lys Arg Lys Glu
385                 390                 395                 400

Gly Ser Ser Asp Ala Ala Glu Ser Thr Asn Tyr Asn Glu Ile Pro Lys
                405                 410                 415

Asn Gly Lys Gly Ser Thr Arg Lys Gly Val Asp His Ser Asn Arg Asn
            420                 425                 430

Gln Ala Thr Leu Asn Glu Lys Gln Arg Phe Pro Ser Lys Gly Lys Ser
        435                 440                 445

Gln Gly Leu Pro Ile Pro Ser Arg Gly Leu Asp Asn Glu Ile Lys Asn
    450                 455                 460

Glu Met Asp Ser Phe Asn Gly Pro Ser His Glu Asn Ile Ile Thr His
465                 470                 475                 480

Gly Arg Lys Tyr His Tyr Val Pro His Arg Gln Asn Asn Ser Thr Arg
                485                 490                 495

Asn Lys Gly Met Pro Gln Gly Lys Gly Ser Trp Gly Arg Gln Pro His
            500                 505                 510

Ser Asn Arg Arg Phe Ser Ser Arg Arg Arg Asp Asp Ser Ser Glu Ser
        515                 520                 525

Ser Asp Ser Gly Ser Ser Ser Glu Ser Asp Gly Asp
    530                 535                 540
```